(12) United States Patent
Kamatani et al.

(10) Patent No.: US 9,315,460 B2
(45) Date of Patent: *Apr. 19, 2016

(54) ORGANIC COMPOUND, LIGHT-EMITTING DEVICE, AND IMAGE DISPLAY APPARATUS

(71) Applicant: CANON KABUSHIKI KAISHA, Tokyo (JP)

(72) Inventors: Jun Kamatani, Tokyo (JP); Takayuki Horiuchi, Tokyo (JP); Naoki Yamada, Inagi (JP); Akihito Saitoh, Gotemba (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/485,481

(22) Filed: Sep. 12, 2014

(65) Prior Publication Data

US 2014/0374738 A1    Dec. 25, 2014

Related U.S. Application Data

(63) Continuation of application No. 13/260,890, filed as application No. PCT/JP2010/057642 on Apr. 22, 2010, now Pat. No. 8,940,413.

(30) Foreign Application Priority Data

Apr. 23, 2009 (JP) ................................ 2009-105356
Jan. 27, 2010 (JP) ................................ 2010-015851

(51) Int. Cl.

| H01L 27/32 | (2006.01) |
|---|---|
| C07D 213/16 | (2006.01) |
| C07D 401/10 | (2006.01) |
| C07C 211/61 | (2006.01) |
| C07D 209/86 | (2006.01) |
| C07D 221/10 | (2006.01) |
| C07D 403/10 | (2006.01) |
| C07D 409/10 | (2006.01) |
| C07F 7/08 | (2006.01) |
| C07C 25/22 | (2006.01) |
| C07C 43/285 | (2006.01) |
| C07C 49/792 | (2006.01) |
| C07D 221/16 | (2006.01) |
| C07C 13/62 | (2006.01) |
| C07C 43/275 | (2006.01) |
| C07F 9/50 | (2006.01) |
| H01L 51/00 | (2006.01) |
| C09K 11/06 | (2006.01) |
| H05B 33/10 | (2006.01) |
| H01L 51/50 | (2006.01) |

(52) U.S. Cl.
CPC .............. *C07D 213/16* (2013.01); *C07C 13/62* (2013.01); *C07C 25/22* (2013.01); *C07C 43/275* (2013.01); *C07C 49/792* (2013.01); *C07C 211/61* (2013.01); *C07F 7/0809* (2013.01); *C07F 9/5022* (2013.01); *C09K 11/06* (2013.01); *H01L 51/006* (2013.01); *H01L 51/0052* (2013.01); *H01L 51/0056* (2013.01); *H01L 51/0058* (2013.01); *H01L 51/0067* (2013.01); *H01L 51/0068* (2013.01); *H01L 51/0072* (2013.01); *H01L 51/0094* (2013.01); *H05B 33/10* (2013.01); *C07C 2101/14* (2013.01); *C07C 2102/42* (2013.01); *C07C 2103/18* (2013.01); *C07C 2103/24* (2013.01); *C07C 2103/40* (2013.01); *C07C 2103/50* (2013.01); *C07C 2103/52* (2013.01); *C07C 2103/54* (2013.01); *C09K 2211/1007* (2013.01); *C09K 2211/1011* (2013.01); *C09K 2211/1014* (2013.01); *C09K 2211/1029* (2013.01); *C09K 2211/1059* (2013.01); *C09K 2211/1092* (2013.01); *H01L 51/5012* (2013.01); *Y10S 428/917* (2013.01)

(58) Field of Classification Search
None
See application file for complete search history.

(56) References Cited

U.S. PATENT DOCUMENTS 8,293,384 B2 * 10/2012 Kamatani ............... C07C 13/62
                                                                                    313/504
8,940,413 B2 *  1/2015 Kamatani ............... C07C 13/62
                                                                                    313/504

*Primary Examiner* — Andrew K Bohaty
(74) *Attorney, Agent, or Firm* — Canon USA Inc. IP Division

(57) ABSTRACT

Provided is an acenaphtho[1,2-k]benzo[e]acephenanthrene derivative represented by general formula (1):

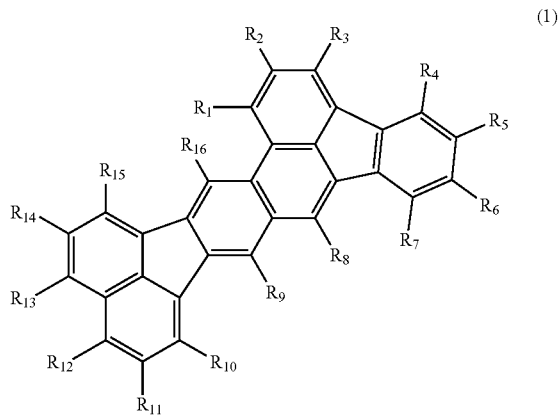

wherein $R_1$ to $R_{16}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group; and at least one of $R_1$ to $R_8$ and $R_{10}$ to $R_{15}$ is selected from a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

5 Claims, 4 Drawing Sheets

ORGANIC COMPOUND, LIGHT-EMITTING DEVICE, AND IMAGE DISPLAY APPARATUS

CROSS REFERENCE TO RELATED APPLICATIONS

This application is a Continuation of U.S. patent application Ser. No. 13/260,890 filed Sep. 28, 2011, which was a 371 national stage entry of International Application No. PCT/JP2010/057642, filed Apr. 22, 2010 and claims priority to Japanese Patent Application No. 2010-015851 filed Jan. 27, 2010, and Japanese Patent Application No. 2009-105356 filed Apr. 23, 2009, each of which are hereby incorporated by reference herein in their entireties.

TECHNICAL FIELD

The present invention relates to a novel organic compound. The present invention also relates to an organic light-emitting device and image display apparatus that include the organic compound.

BACKGROUND ART

Organic light-emitting devices include an anode, cathode, and a thin film containing a fluorescent organic compound and disposed between the anode and the cathode. Excitons of the fluorescent organic compound are generated by injecting electrons and holes from the electrodes, and the organic light-emitting devices utilize light emitted when the excitons are returned to the ground state. Such organic light-emitting devices are also referred to as "organic electroluminescent devices" or "organic EL devices".

Recently, organic light-emitting devices have become markedly advanced and the possibility of a wide variety of applications has been suggested therefor because of the high luminance achieved by a low applied voltage, a variety of emission wavelengths, a high-speed responsiveness, and the possibility of realization of a thin, lightweight light-emitting devices. Heretofore, novel compounds have been actively developed. This is because creation of novel compounds is important to provide high-performance organic light-emitting devices. For example, Patent Literatures 1 to 3 describe examples of organic compounds used as the materials for a light-emitting layer.

However, from the standpoint of practical application, there is still a room for improvement in the organic compounds described in Patent Literatures 1 to 3 and organic light-emitting devices including the same. Specifically, for practical application, an optical output with higher luminance and higher conversion efficiency are necessary. Furthermore, improvements are necessary in terms of durability, for example, a change with time due to long-term use and degradation due to an atmospheric gas containing oxygen, moisture, or the like.

Furthermore, considering an application to a full-color display or the like, a blue-light emission having good color purity and high luminous efficiency is necessary. However, technologies related to these issues have not yet satisfactorily been developed. Accordingly, in particular, an organic light-emitting device having high color purity, high luminous efficiency, and high durability and a material that realizes such an organic light-emitting device have been desired.

CITATION LIST

Patent Literature

PTL 1 Japanese Patent Laid-Open No. 2-247278
PTL 2 Japanese Patent Laid-Open No. 8-113576
PTL 3 Japanese Patent Laid-Open No. 11-12205

SUMMARY OF INVENTION

The present invention has been made to solve the above-described problems in the related art. More specifically, the present invention provides a novel organic compound that is suitably used mainly in a blue-light-emitting device and an organic light-emitting device including the same.

Solution to Problem

The present invention provides an acenaphtho[1,2-k]benzo[e]acephenanthrene derivative represented by general formula (1) below.

[Chem. 1]

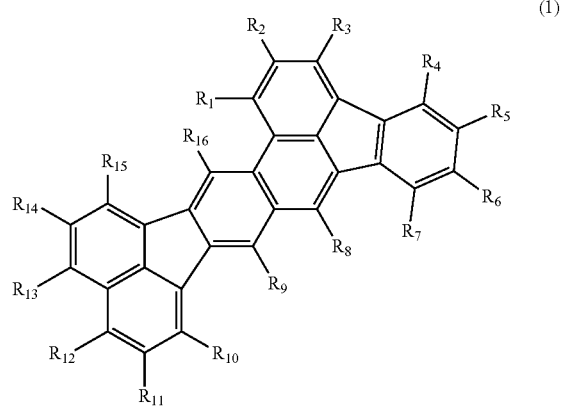

In general formula (1), $R_1$ to $R_{16}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group. In addition, at least one of $R_1$ to $R_8$ and $R_{10}$ to $R_{15}$ is selected from a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

An organic light-emitting device including the novel compound of the present invention can realize a light emission with high efficiency and high luminance.

DESCRIPTION OF EMBODIMENTS

Figure 1:
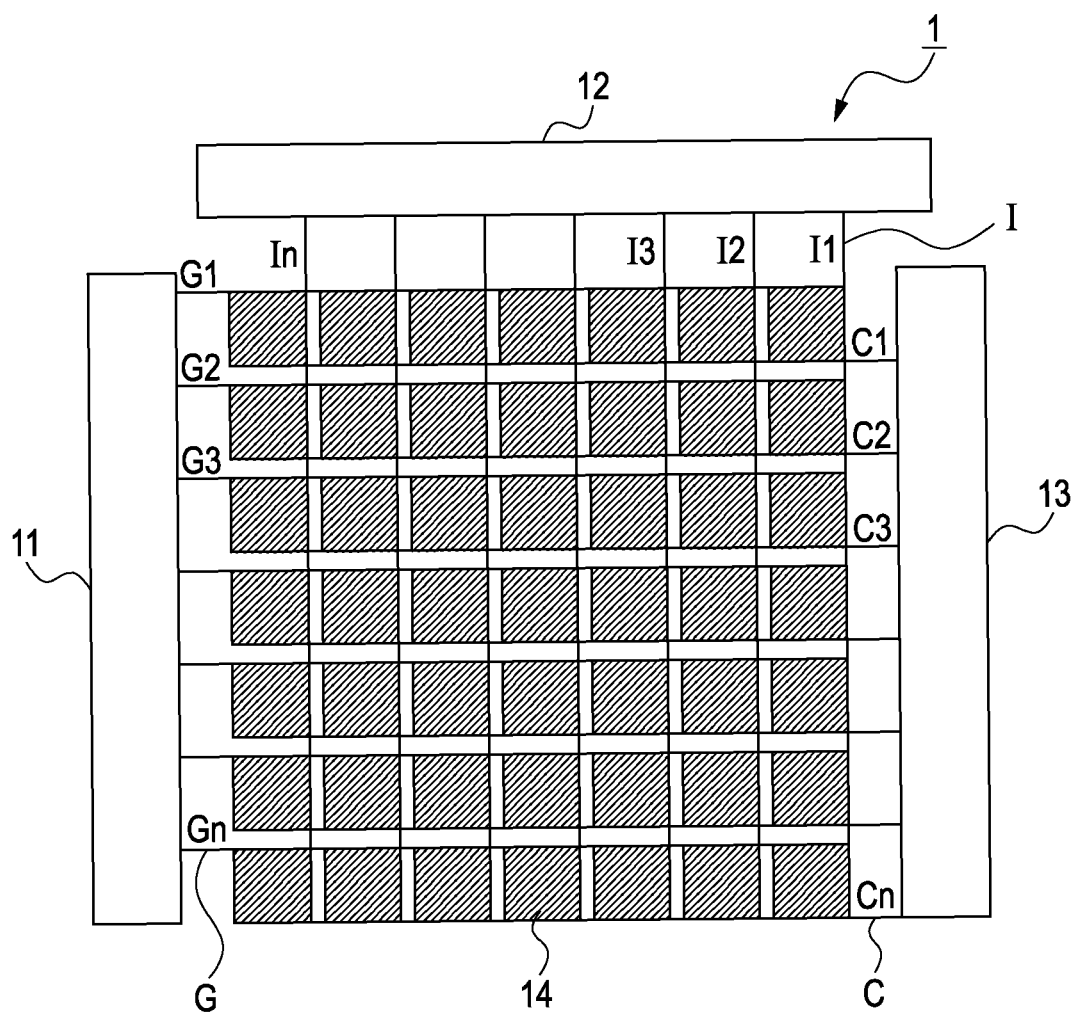
FIG. 1 is a schematic view showing organic light-emitting devices according to the present invention and units configured to supply the organic light-emitting devices according to the present invention with electrical signals.

Compounds of the present invention will now be described in detail. An organic compound according to the present invention is an acenaphtho[1,2-k]benzo[e]acephenanthrene derivative represented by general formula (1).

[Chem. 1]

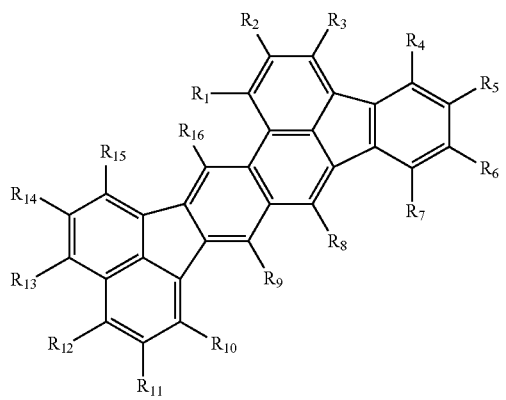

(1)

In general formula (1), $R_1$ to $R_{16}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group. In addition, at least one of $R_1$ to $R_8$ and $R_{10}$ to $R_{15}$ is selected from a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

In general formula (1), examples of the alkyl group in the substituted or unsubstituted alkyl group include, but are not limited to, a methyl group, an ethyl group, a n-propyl group, an isopropyl group, a n-butyl group, a tert-butyl group, a sec-butyl group, an octyl group, a 1-adamantyl group, and a 2-adamantyl group.

In general formula (1), examples of the alkoxy group in the substituted or unsubstituted alkoxy group include, but are not limited to, a methoxy group, an ethoxy group, a propoxy group, a 2-ethyl-octyloxy group, a phenoxy group, a 4-tert-butylphenoxy group, a benzyloxy group, and a thienyloxy group.

In general formula (1), examples of the amino group in the substituted or unsubstituted amino group include, but are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

In general formula (1), examples of the aryl group in the substituted or unsubstituted aryl group include, but are not limited to, a phenyl group, a naphthyl group, an indenyl group, a biphenyl group, a terphenyl group, and a fluorenyl group.

In general formula (1), examples of the heterocyclic group in the substituted or unsubstituted heterocyclic group include, but are not limited to, a pyridyl group, an oxazolyl group, an oxadiazolyl group, a thiazolyl group, a thiadiazolyl group, a carbazolyl group, an acridinyl group, and a phenanthrolyl group.

In general formula (1), examples of the substituent that may be included in the substituents $R_1$ to $R_{16}$, namely, the alkyl, alkoxy, amino, aryl, and heterocyclic groups include, but are not limited to, alkyl groups such as a methyl group, an ethyl group, and a propyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, a propoxyl group, and a phenoxyl group; a cyano group; and halogen atoms such as fluorine, chlorine, bromine, and iodine.

Specific examples of the compound represented by general formula (1) are shown below. However, the present invention is not limited thereto.

[Chem. 2]

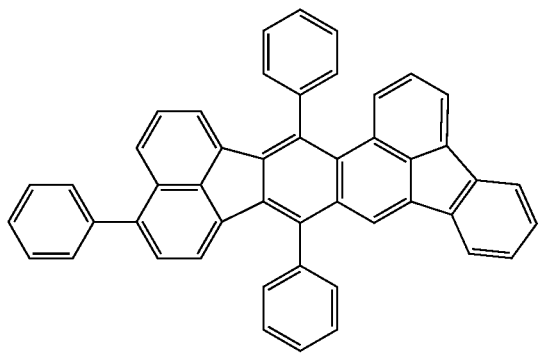

A1

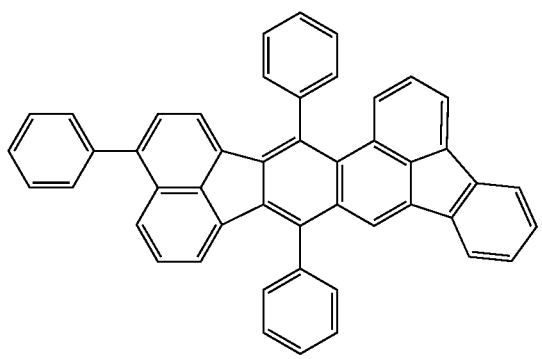

A2

-continued
A3
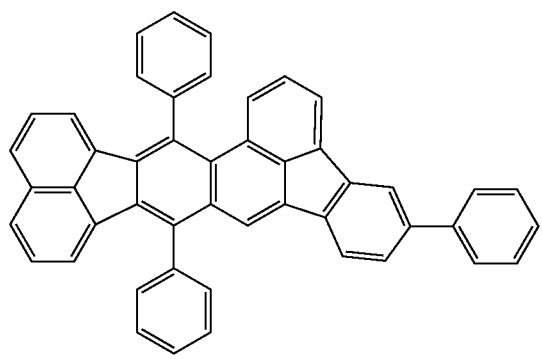
A4
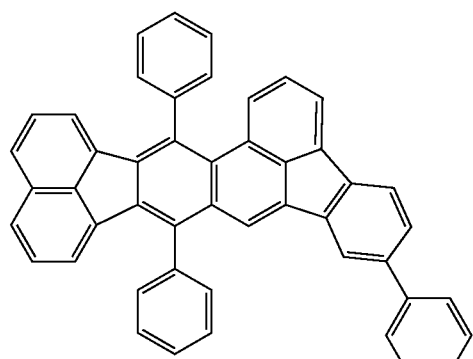
A5
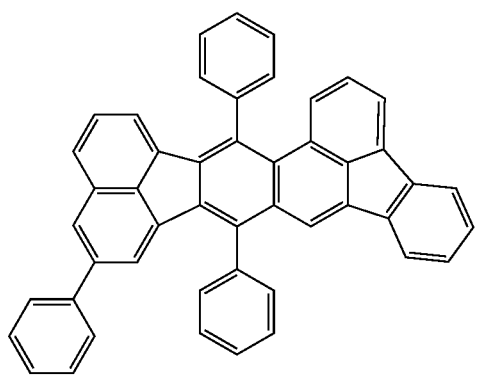
A6
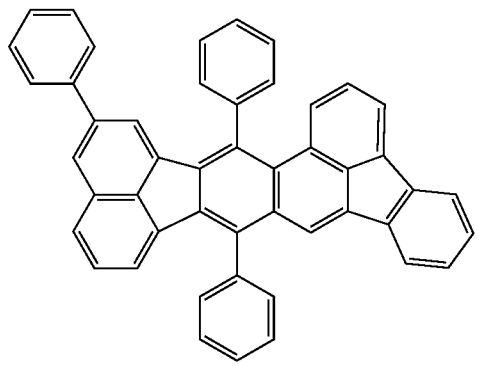
-continued
A7
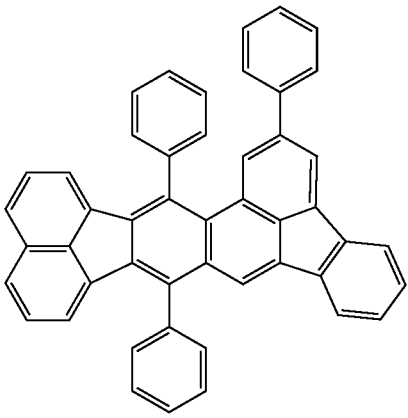
A8
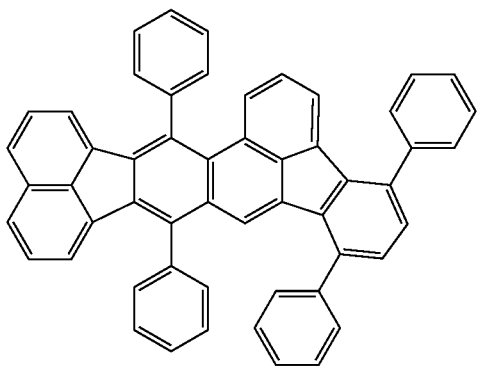
A9
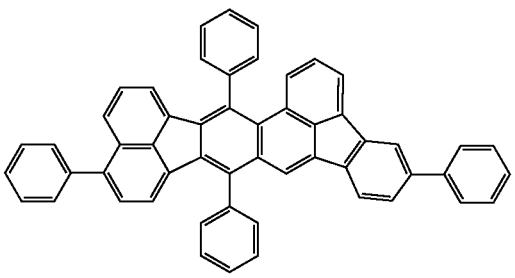
A10
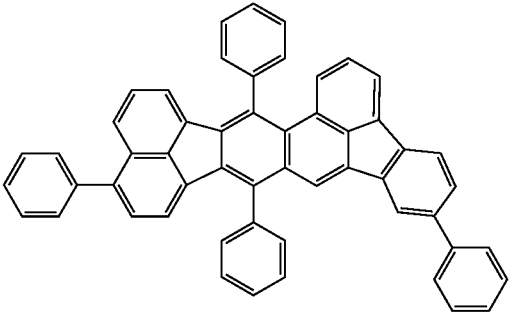

A11
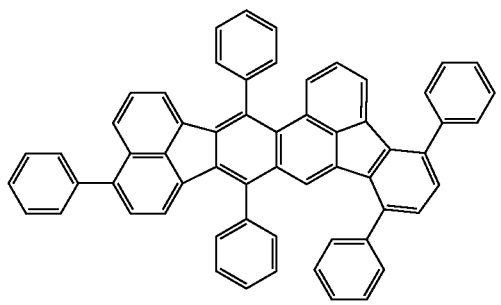
A12
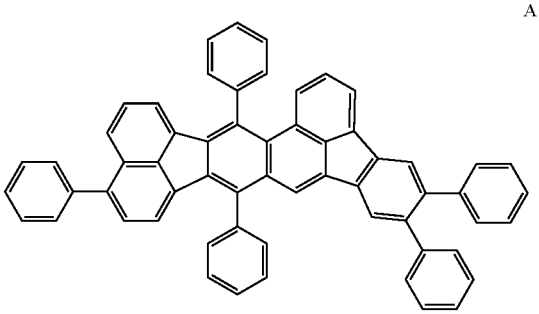
A13
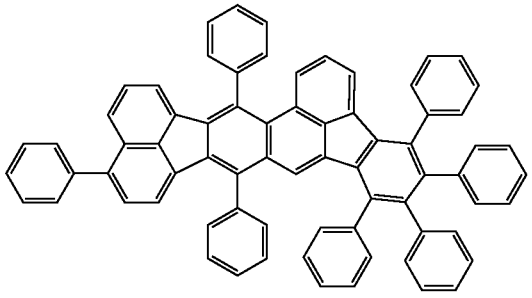
A14
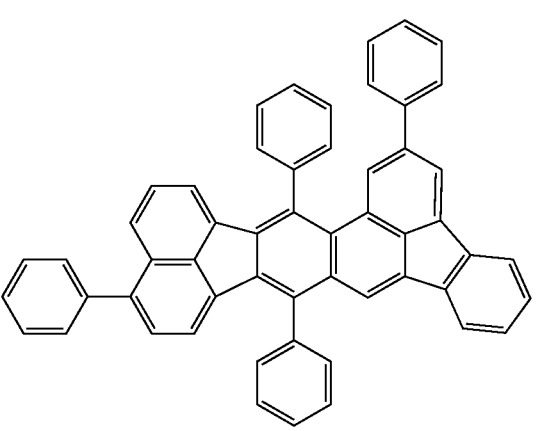
A15
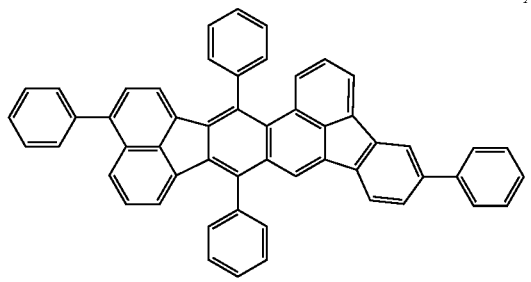
A16
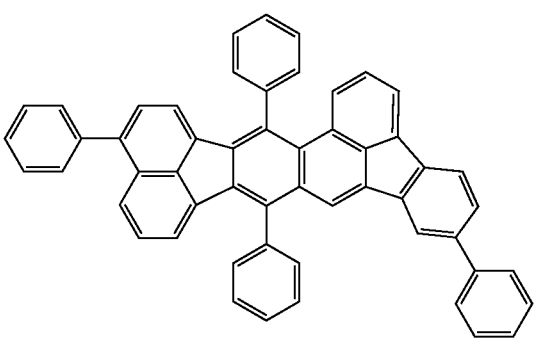
A17
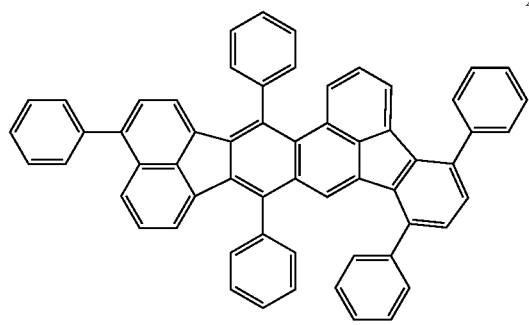
A18
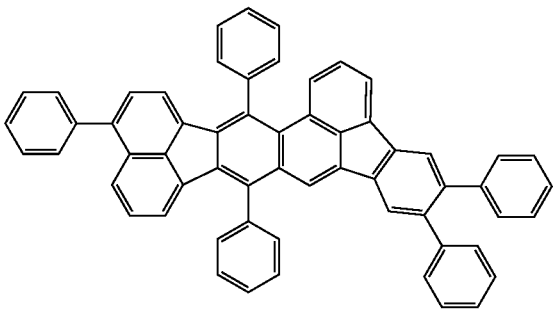
A19
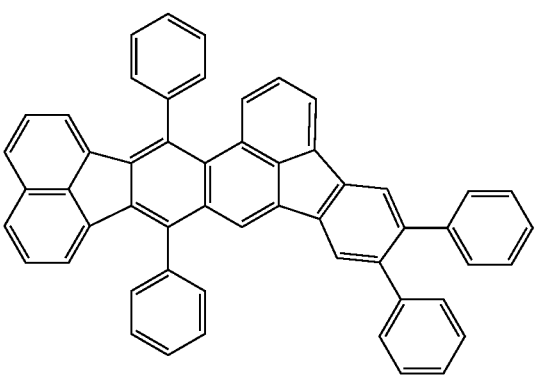

-continued
A20
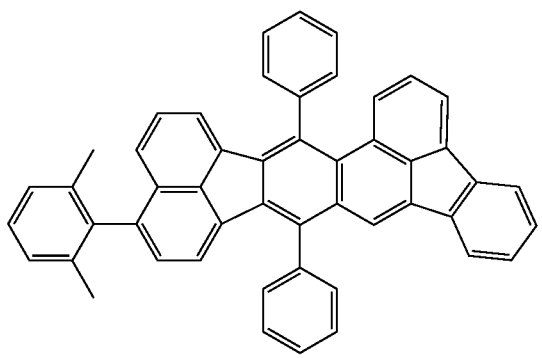
A21
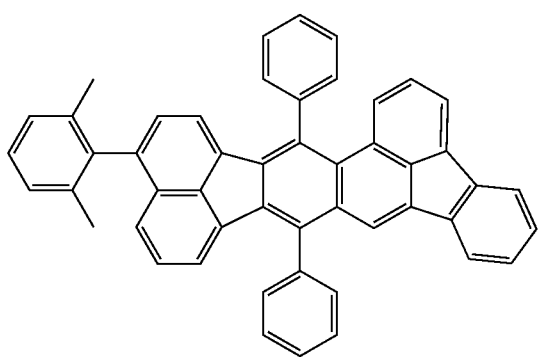
A22
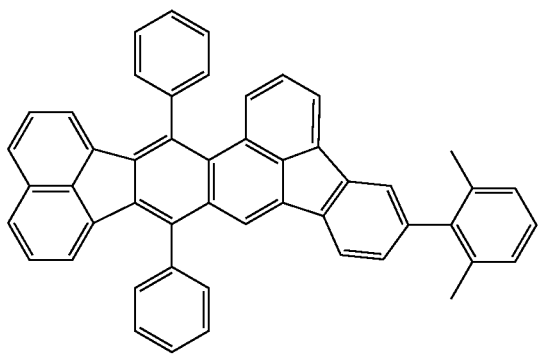
A23
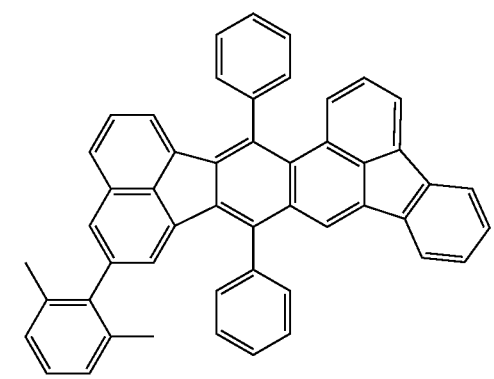
A24
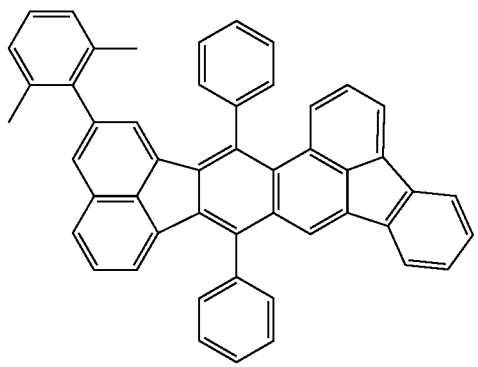
A25
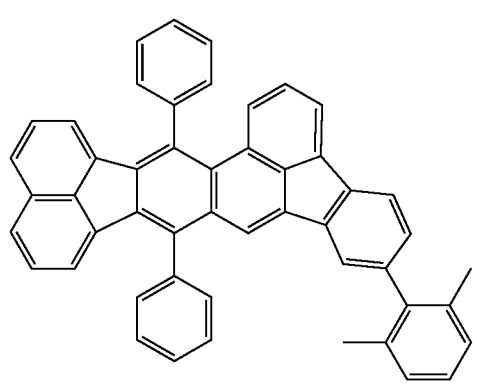
A26
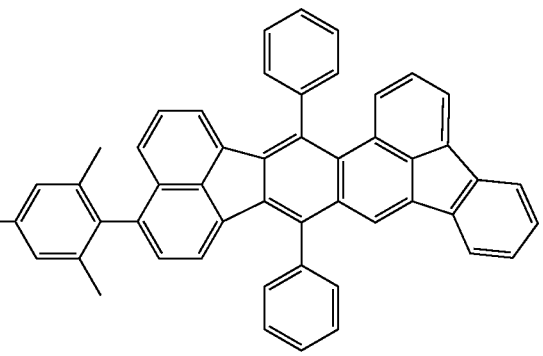
A27
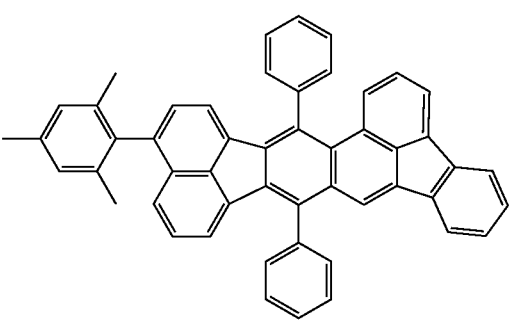

A28
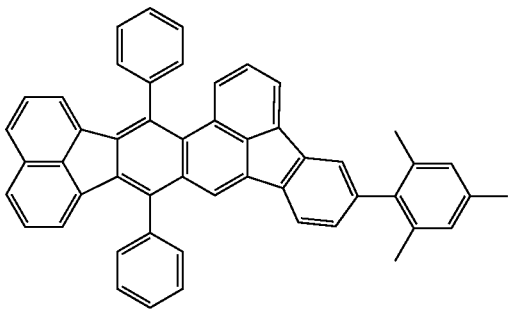
A29
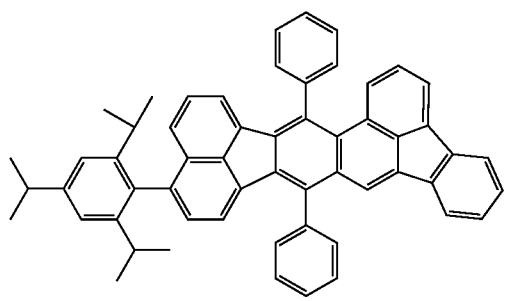
A30
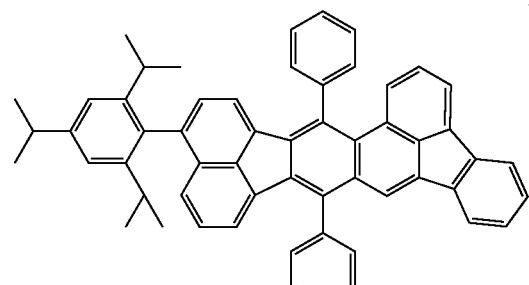
A31
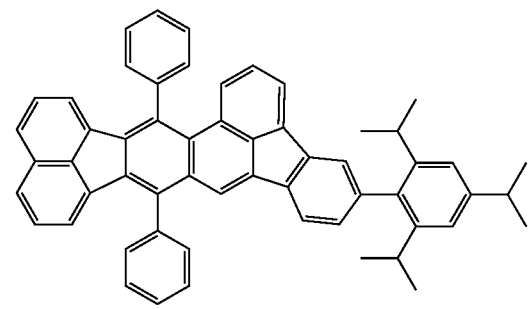
A32
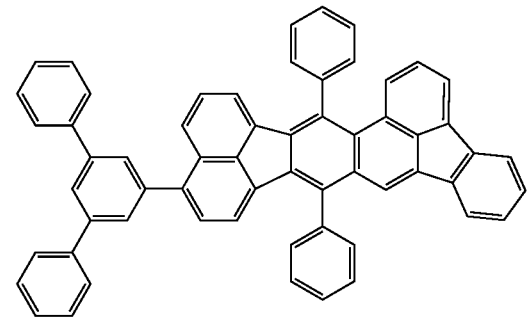
A33
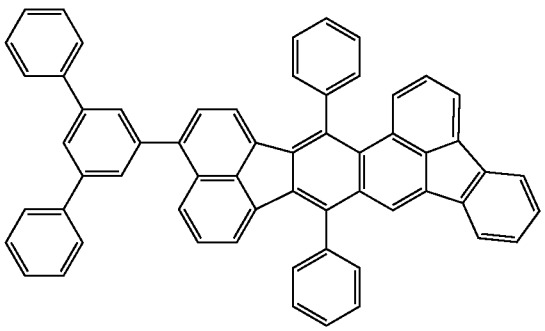
A34
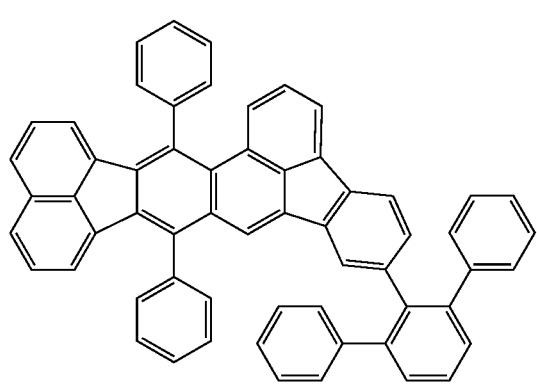
A35
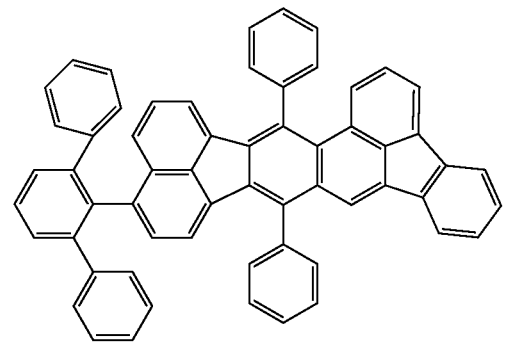
A36
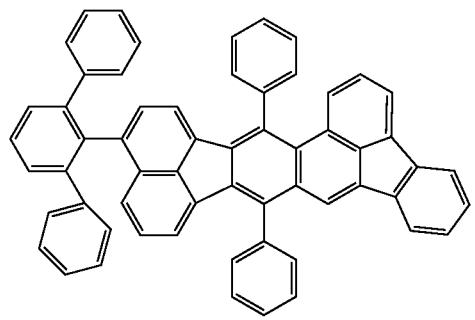

A37
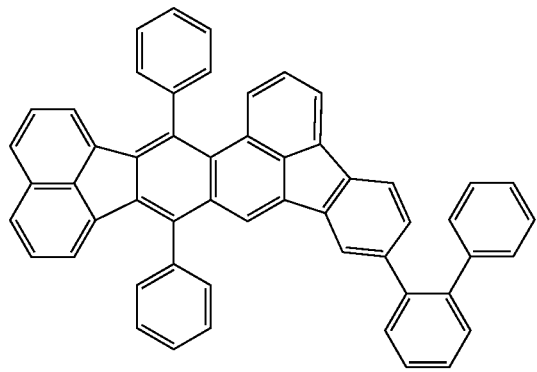
A38
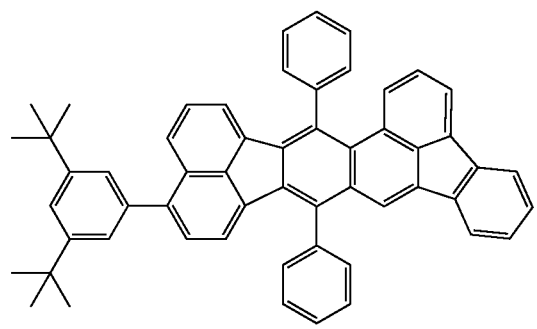
A39
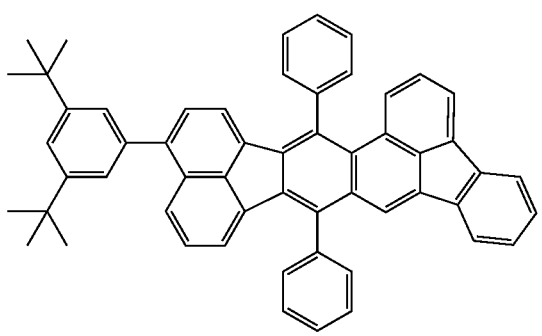
A40
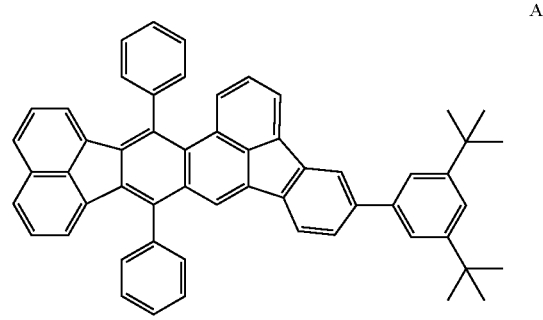
A41
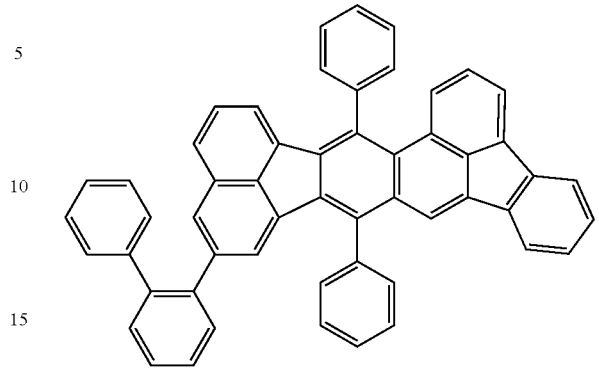
A42
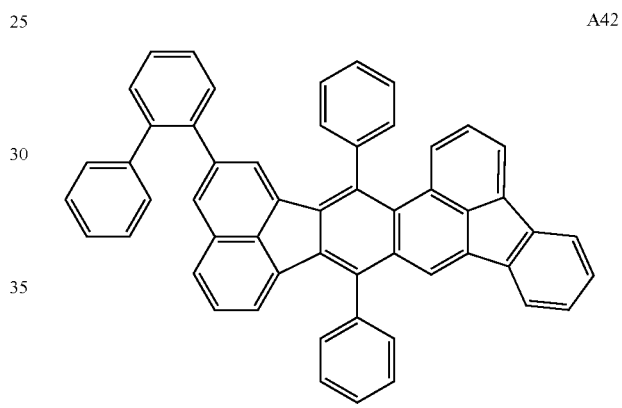
A43
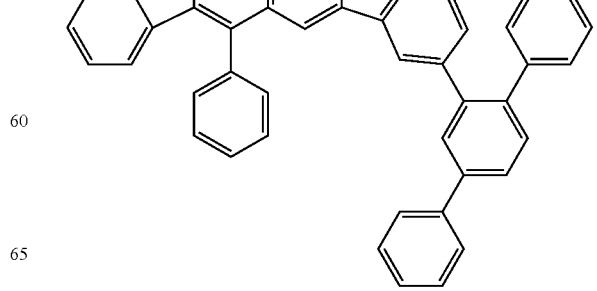

A44
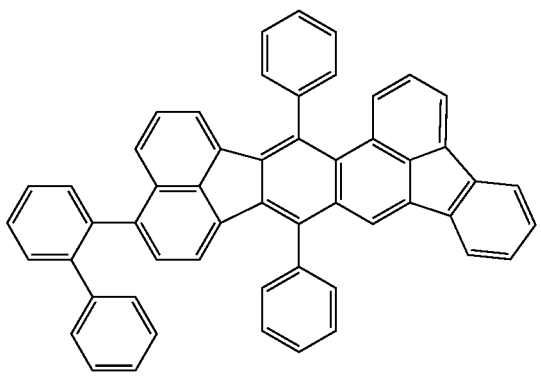
A45
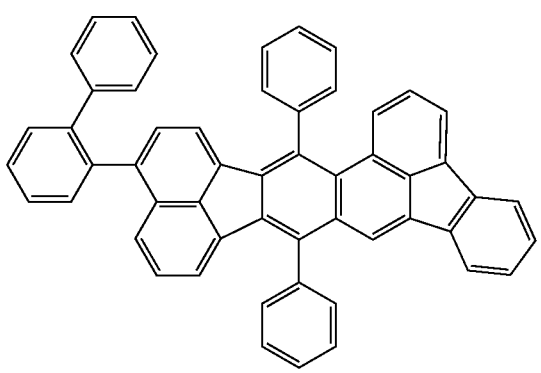
A46
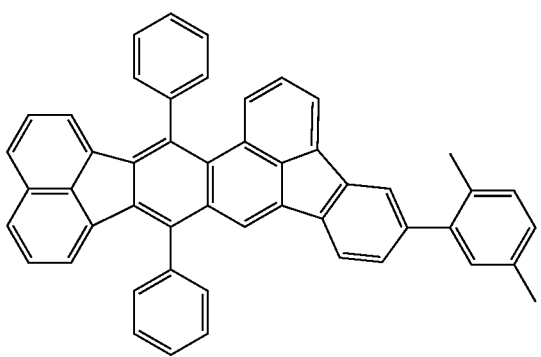
A47
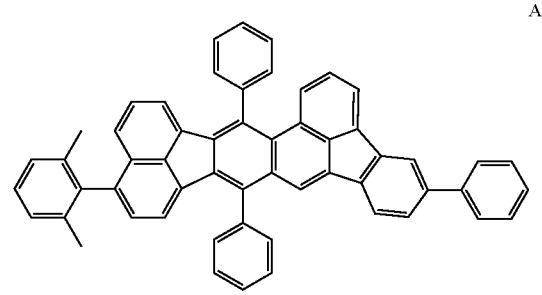
A48
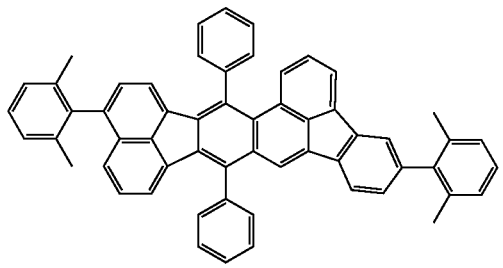
A49
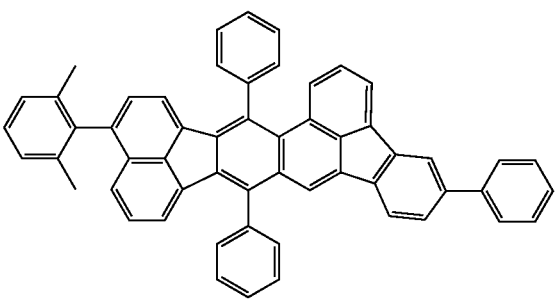
A50
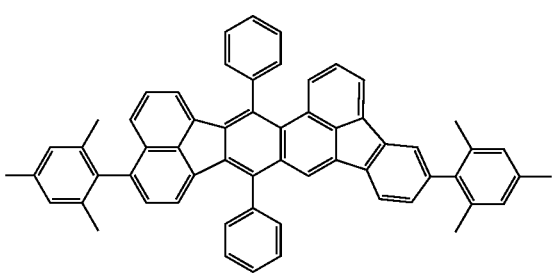
A51
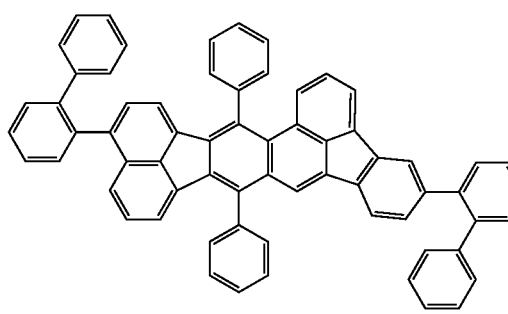
A52
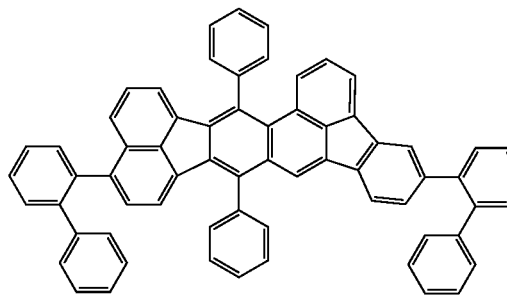

-continued
A53
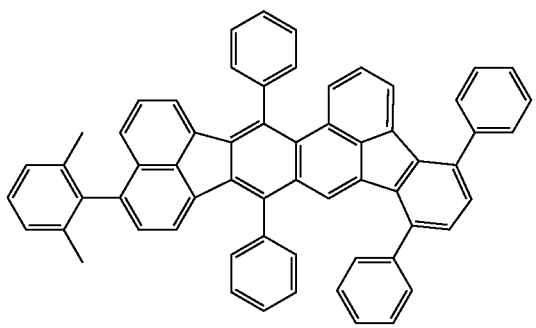
A54
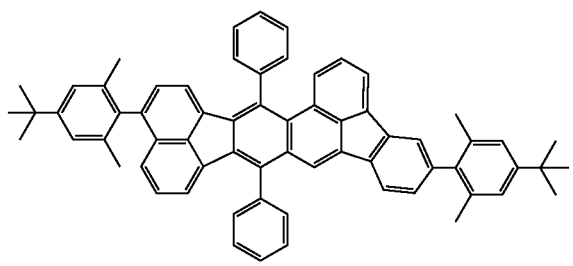
A55
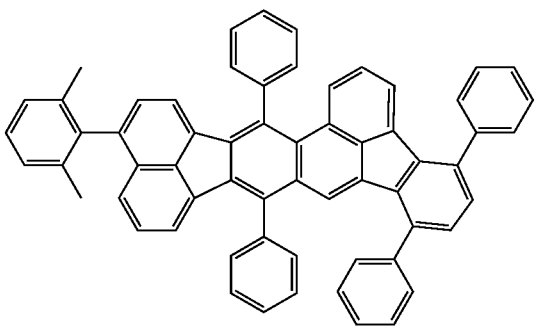
A56
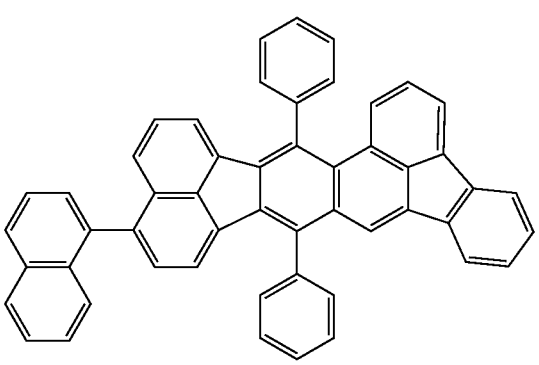
-continued
A57
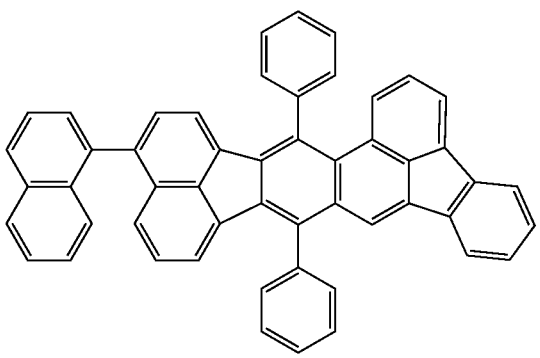
A58
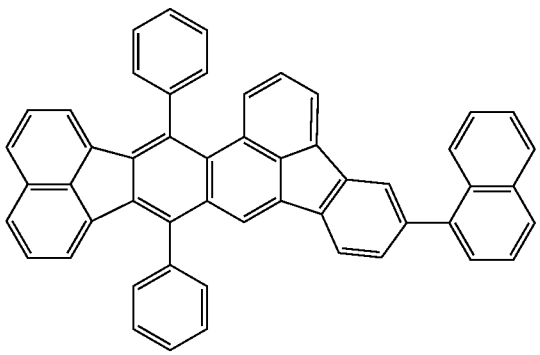
A59
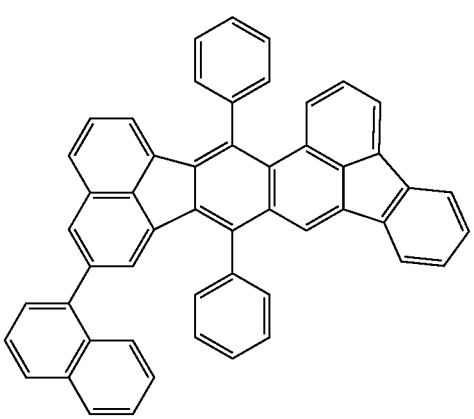
A60
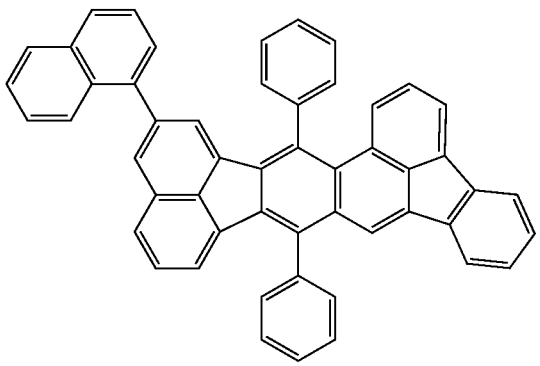

A61
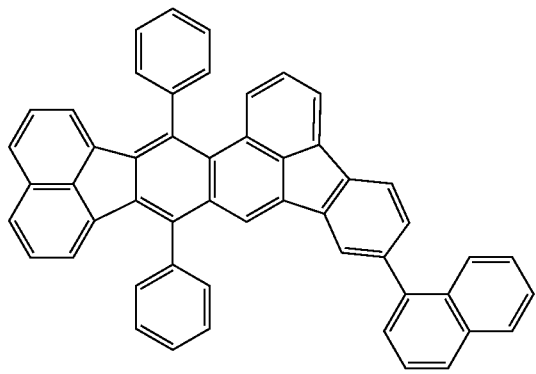
A62
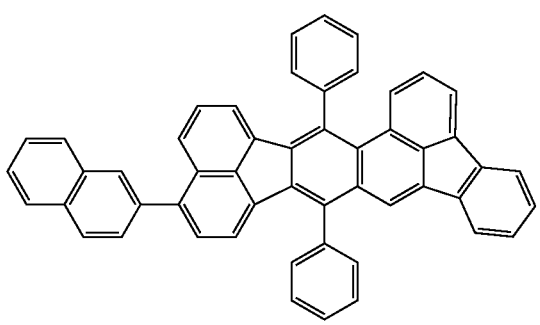
A63
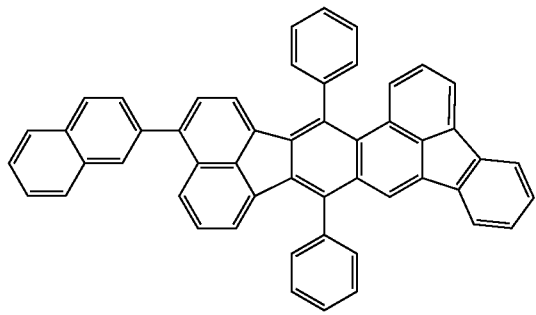
A64
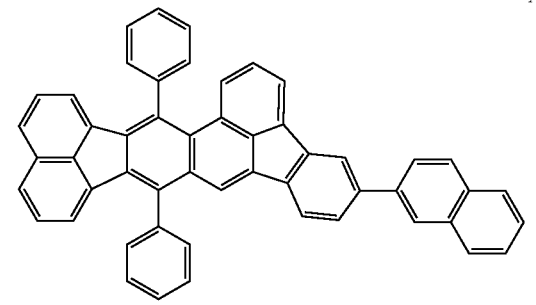
A65
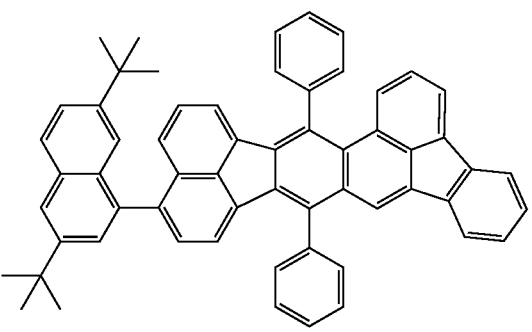
A66
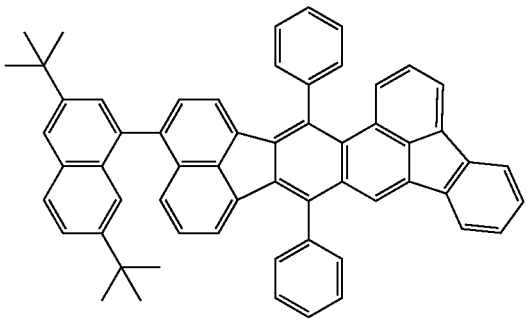
A67
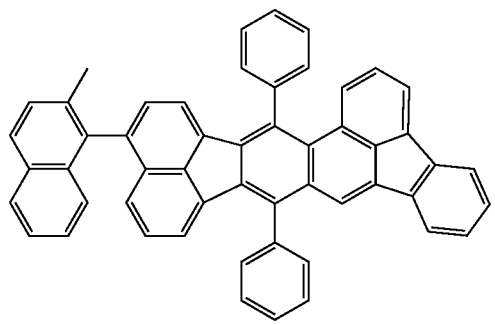
A68
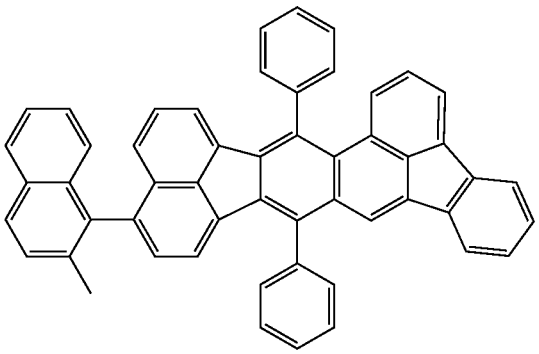

-continued
A69
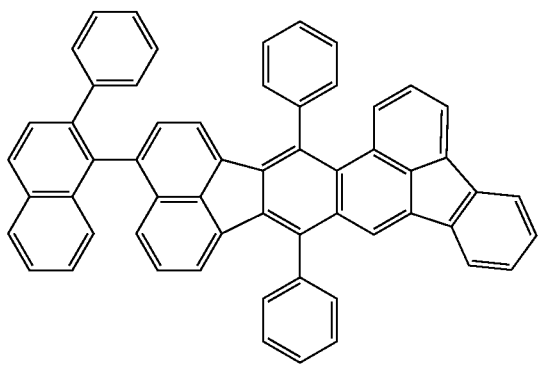
A70
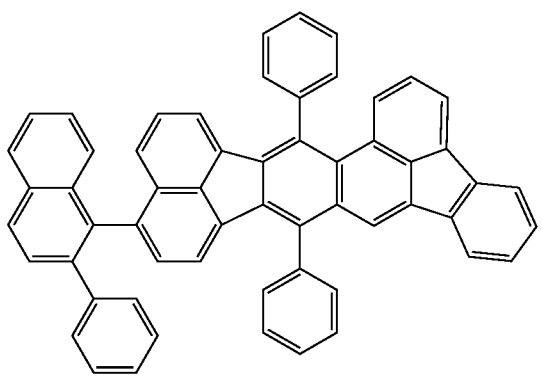
A71
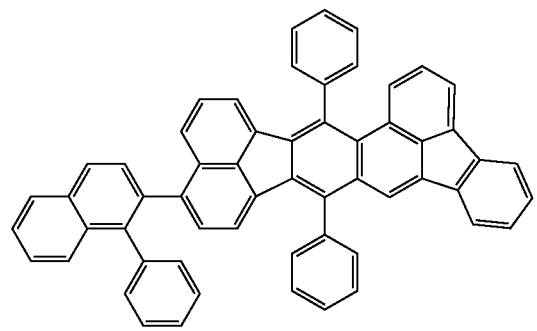
A72
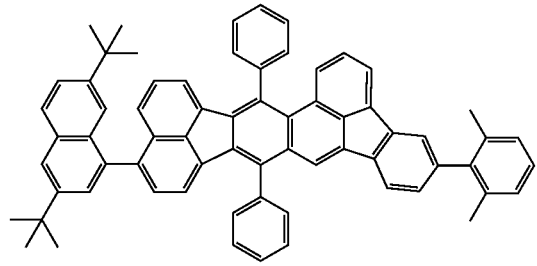
-continued
A73
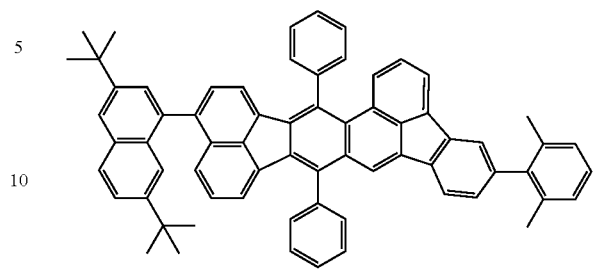
A74
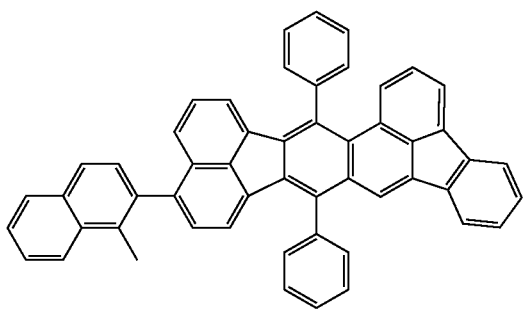
A75
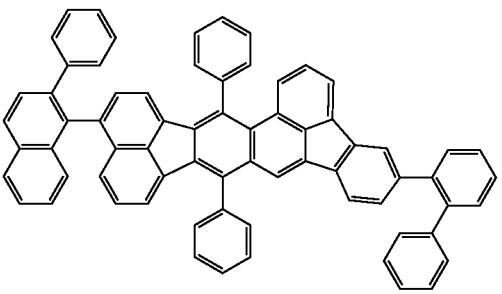
A76
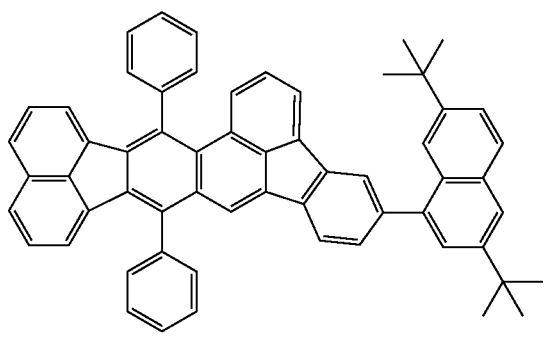

-continued
A77
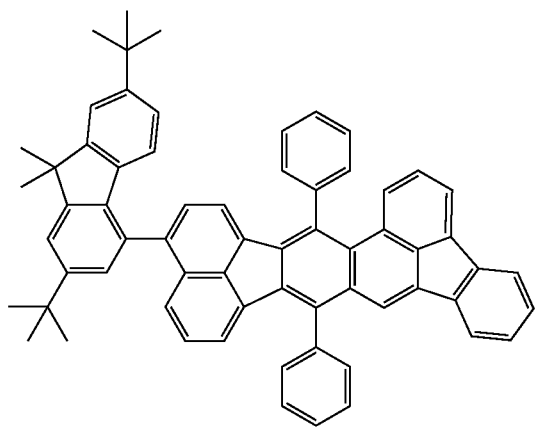
A78
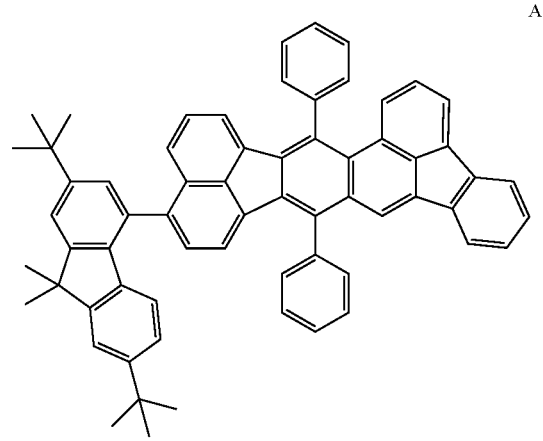
A79
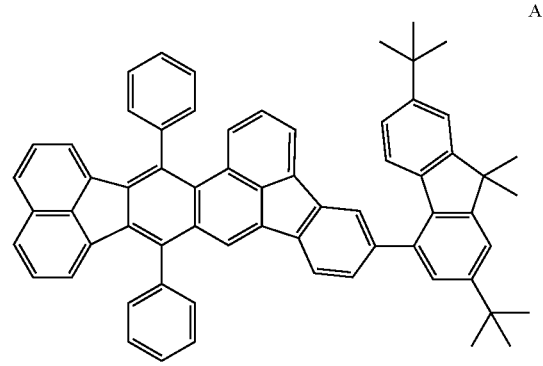
A80
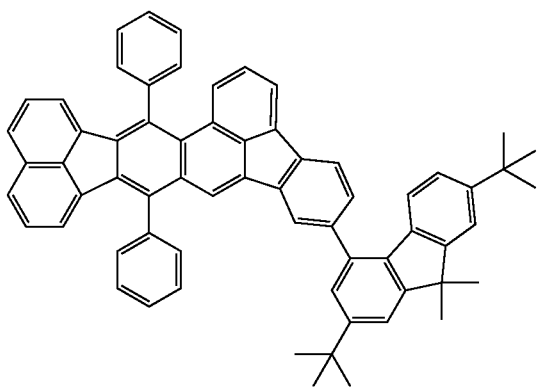
-continued
A81
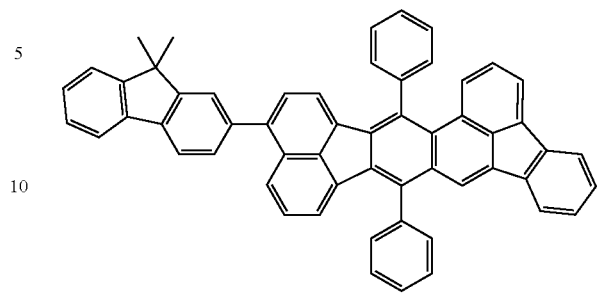
A82
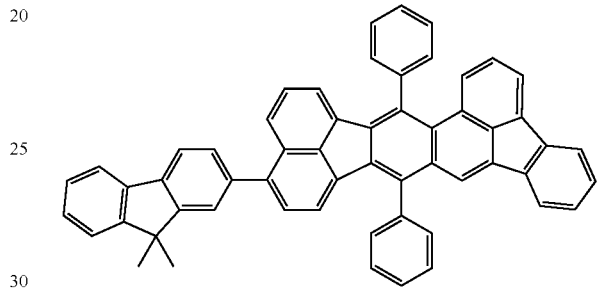
A83
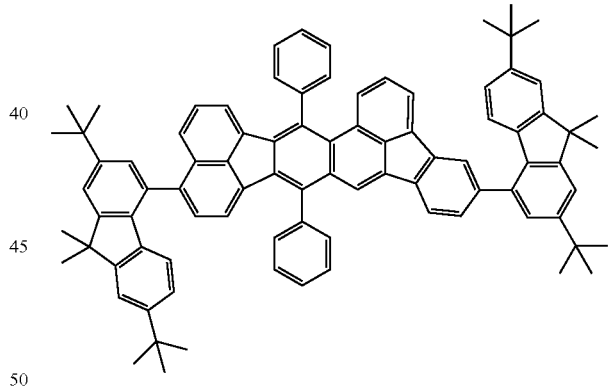
A84
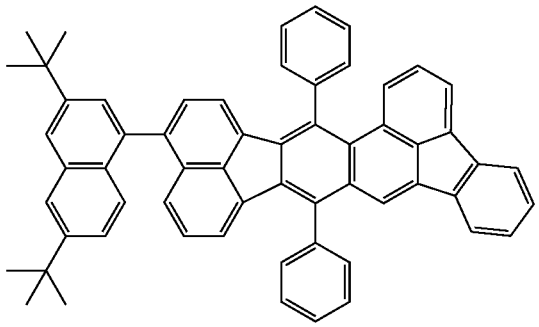

A85
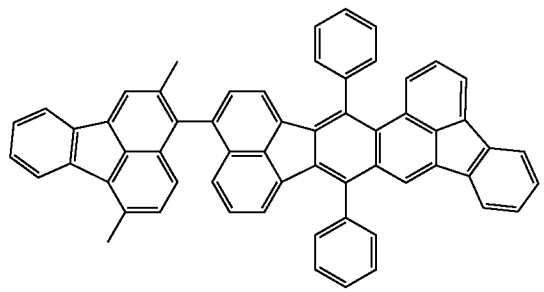
A86
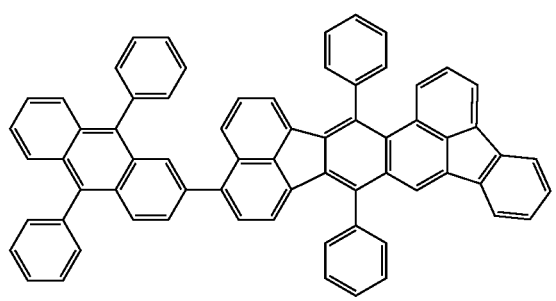
A87
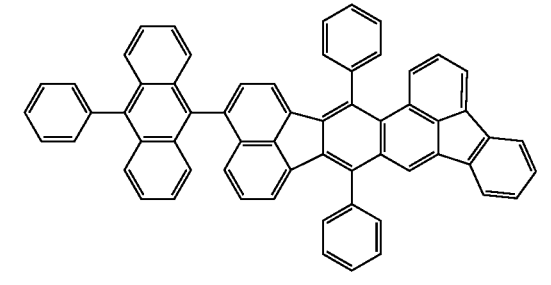
A88
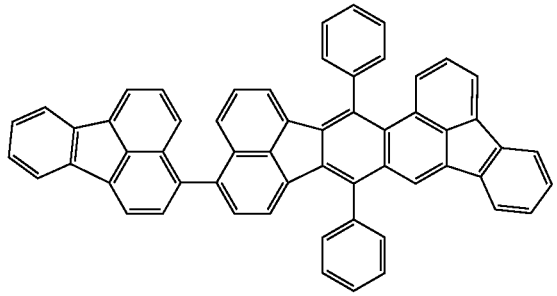
A89
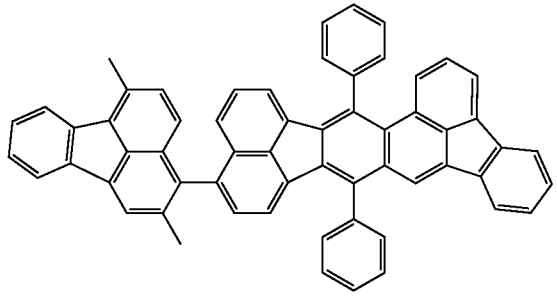
A90
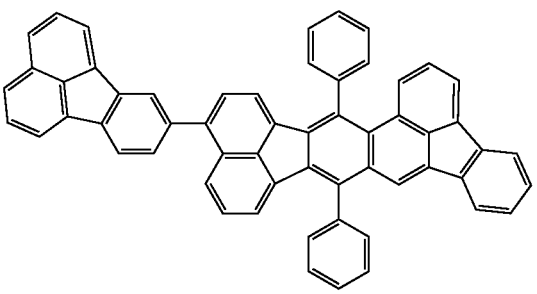
A91
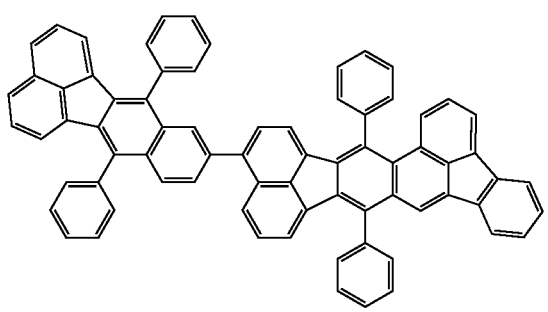
A92
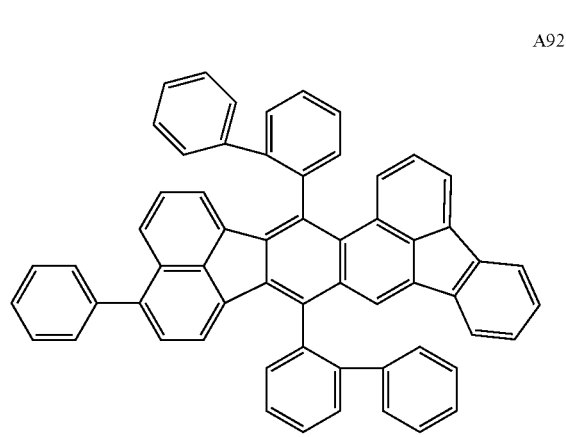
A93
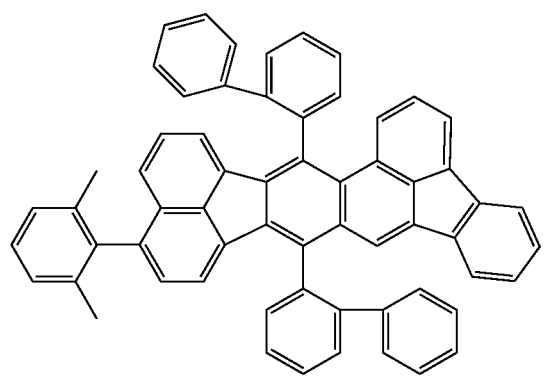

A94
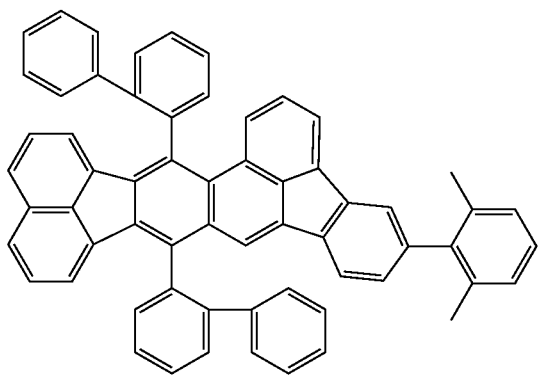
A95
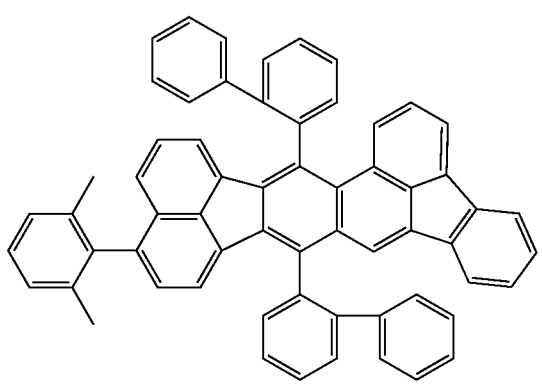
A96
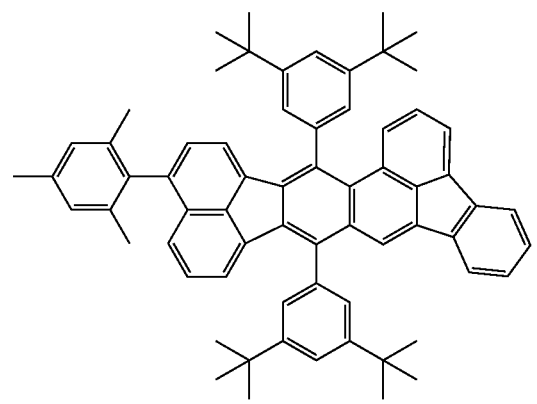
A97
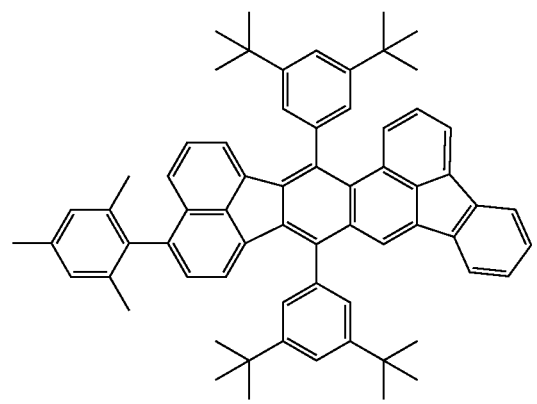
A98
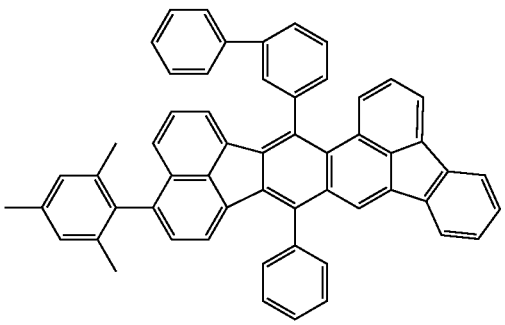
A99
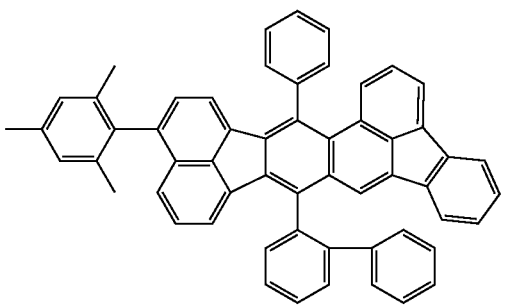
A100
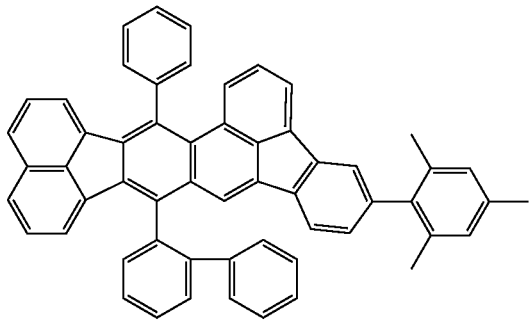
A101
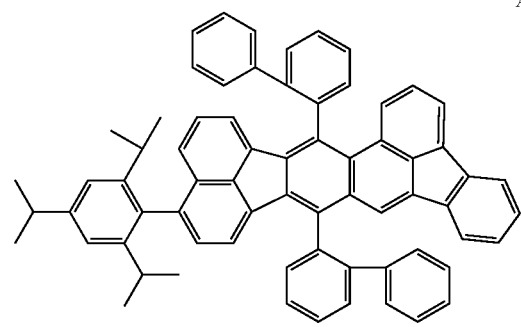

-continued
A102
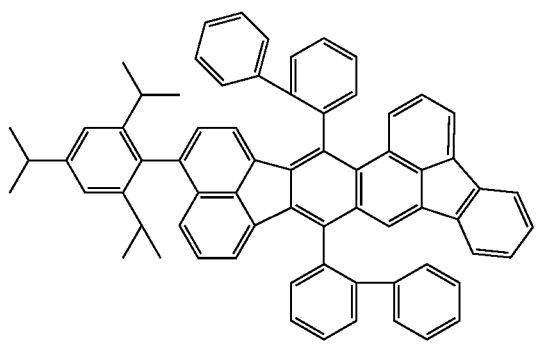
A103
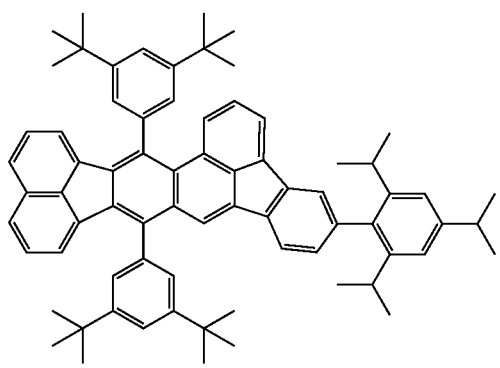
A104
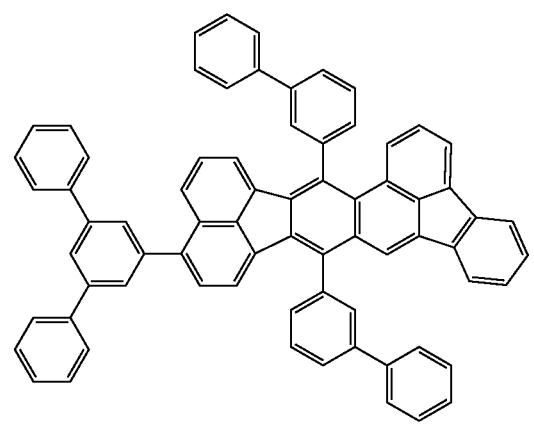
A106
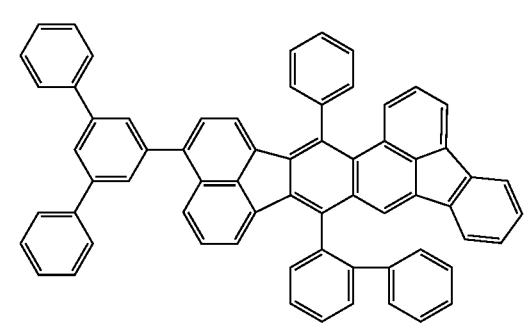
-continued
A107
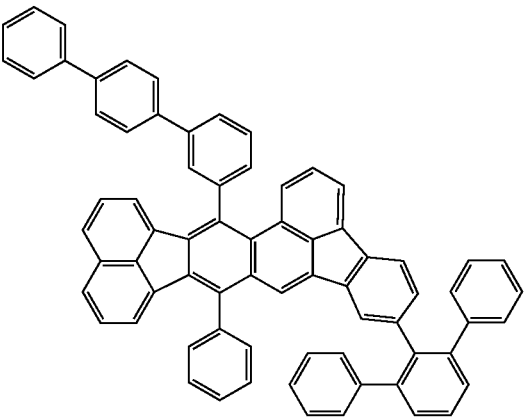
A108
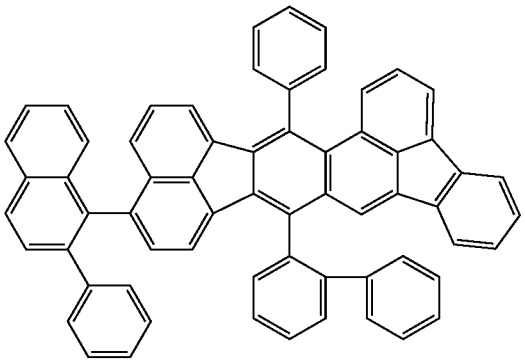
A109
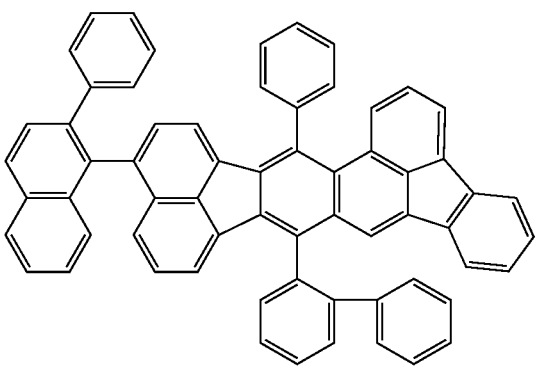
A110
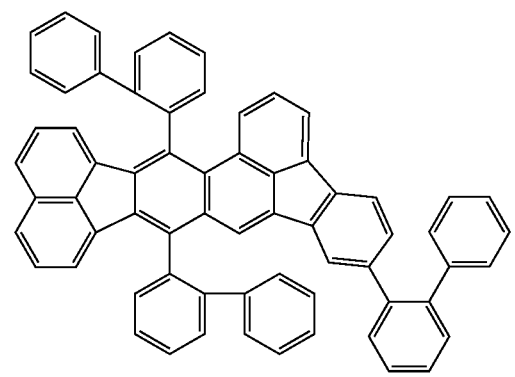

A111
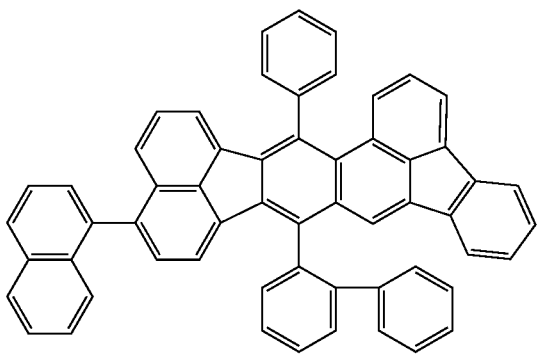
A112
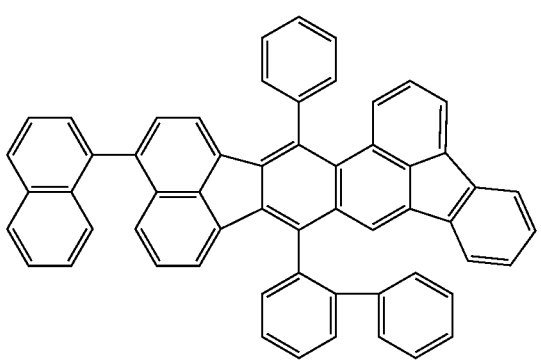
A113
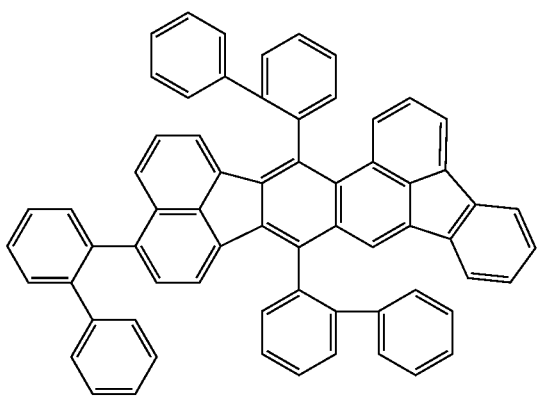
A114
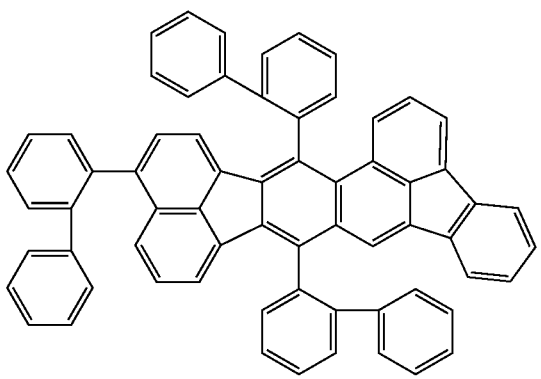
A115
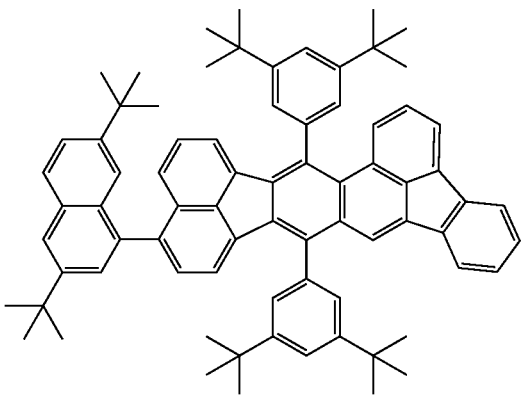
A116
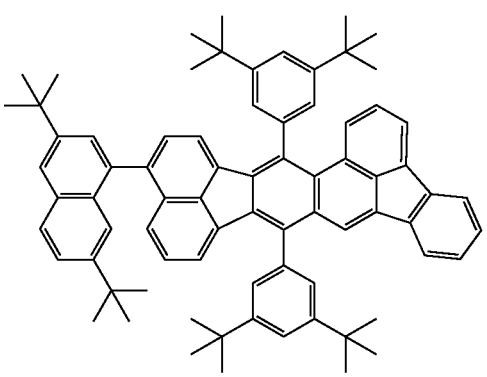
A117
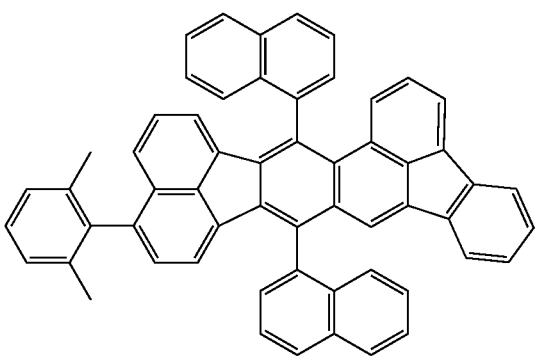
A118
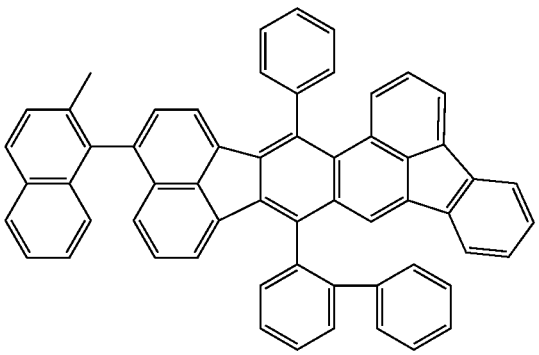

-continued
A119
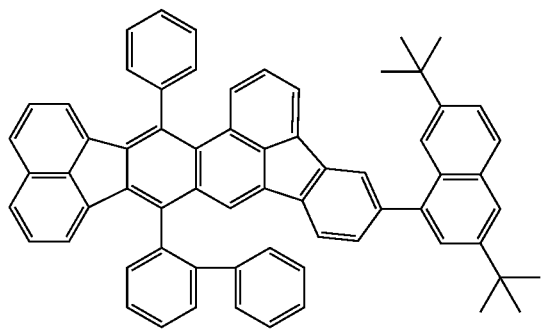
A120
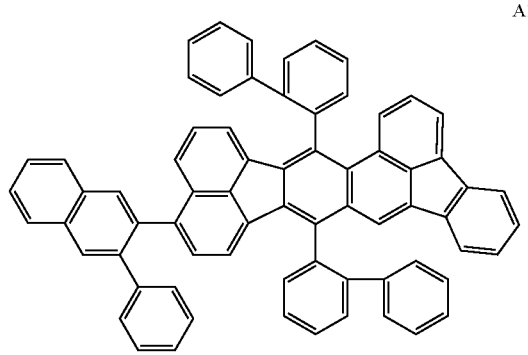
A121
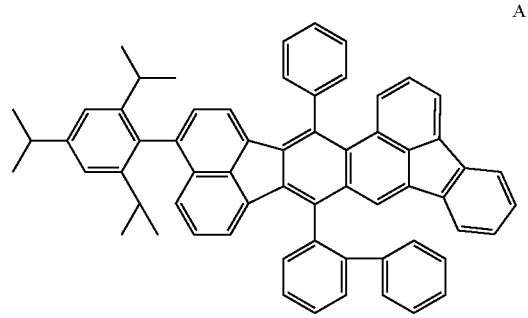
A122
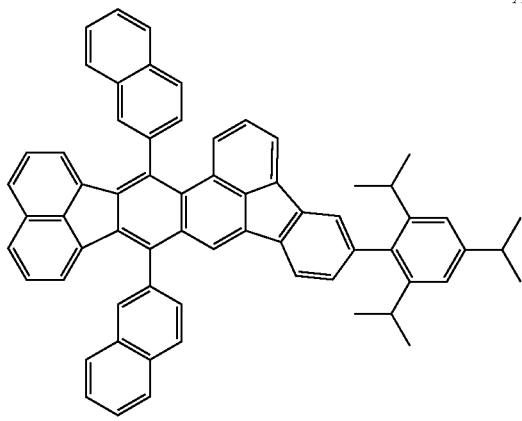
-continued
A123
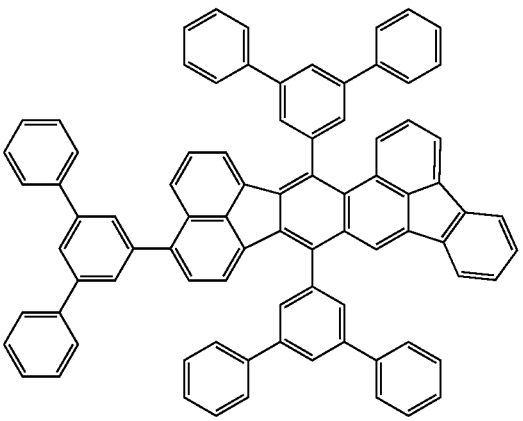
A124
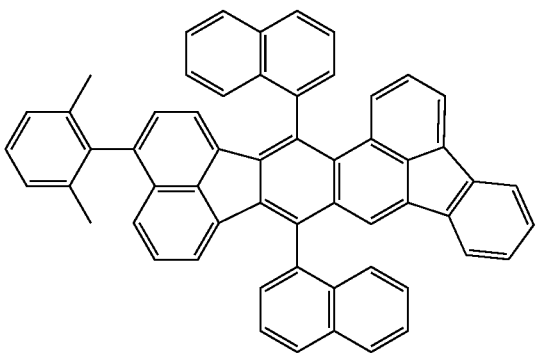
A125
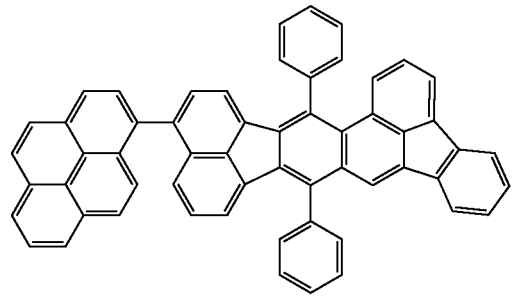
A126
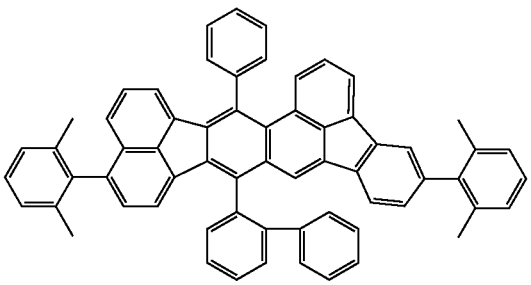

A127
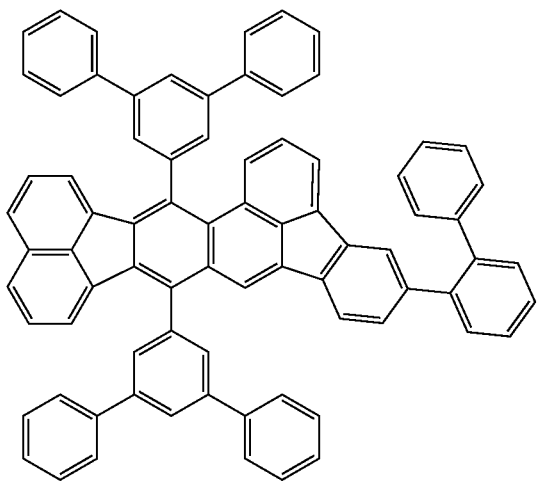
A128
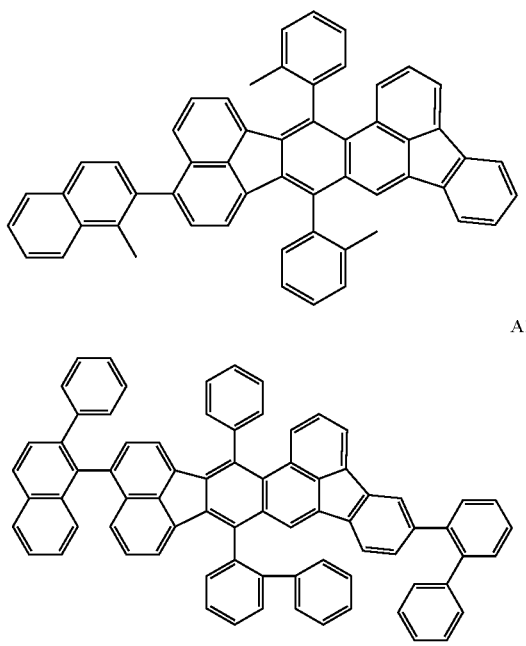
A129
A130
A131
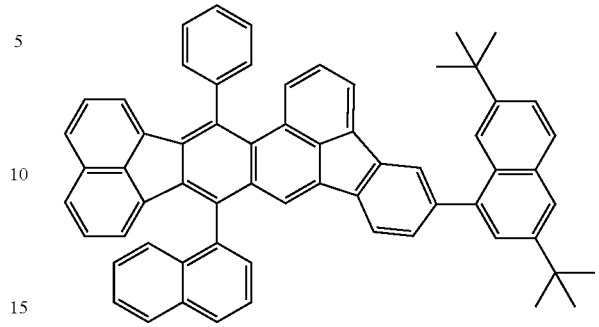
A132
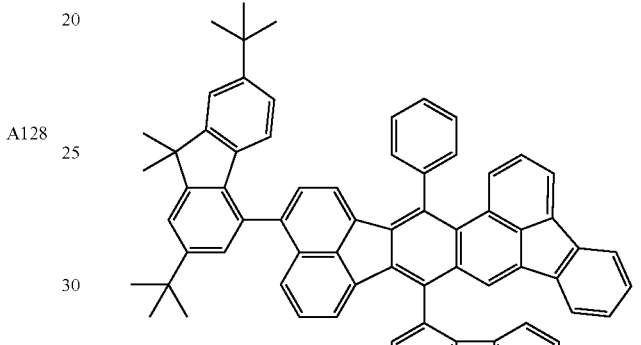
A133
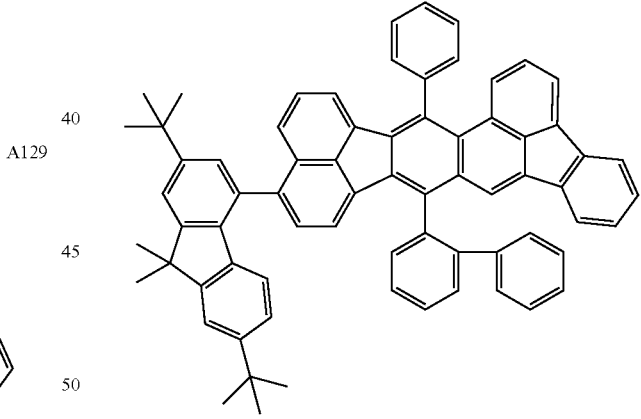
A134
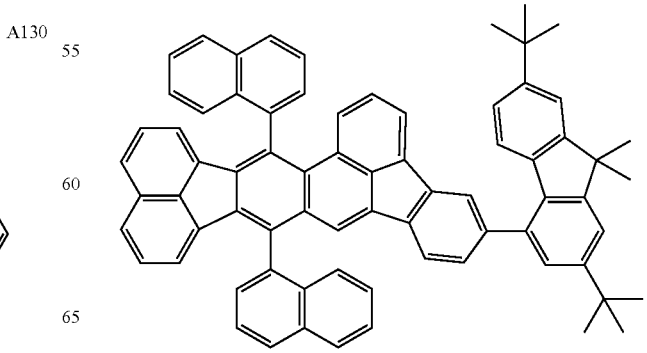

A135
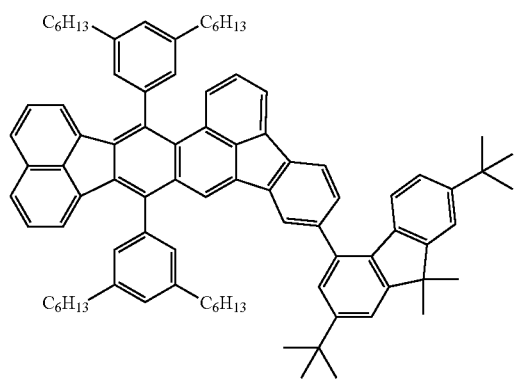
A139
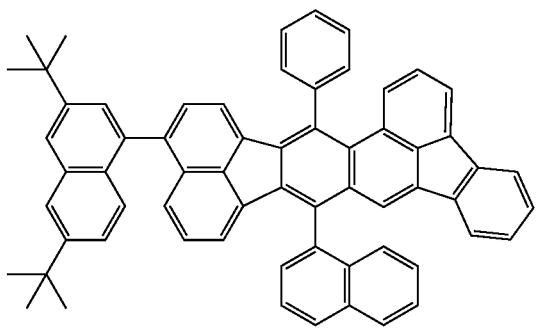
A136
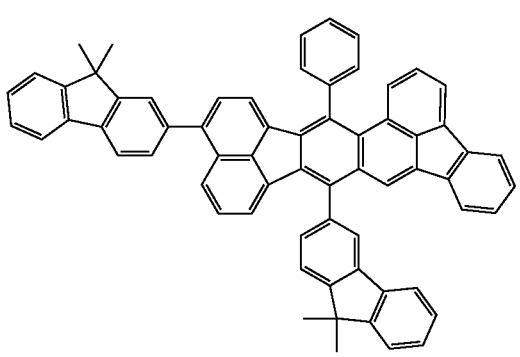
A140
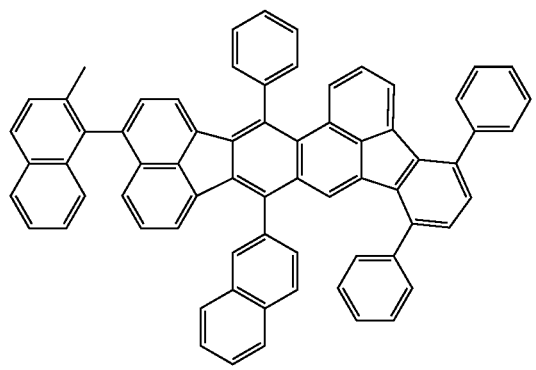
A137
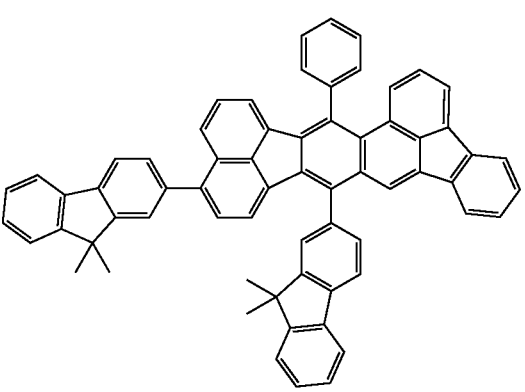
A141
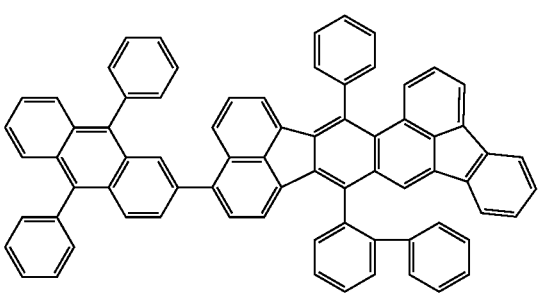
A138
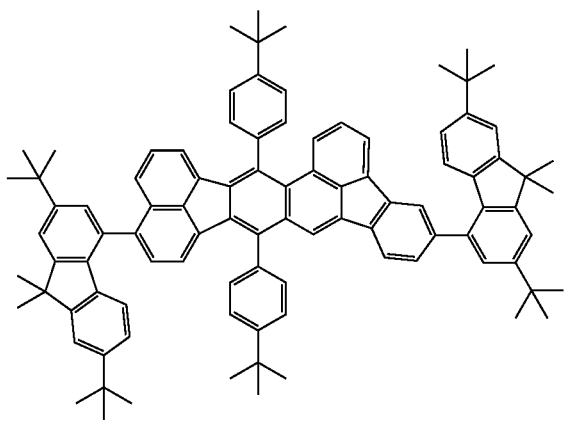
A142
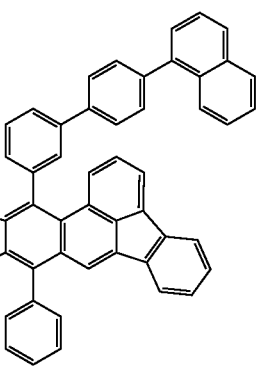

A143
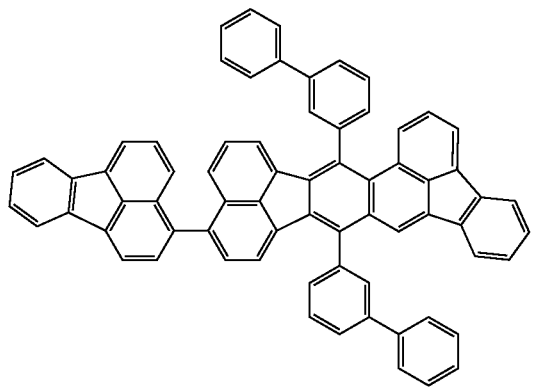
A144
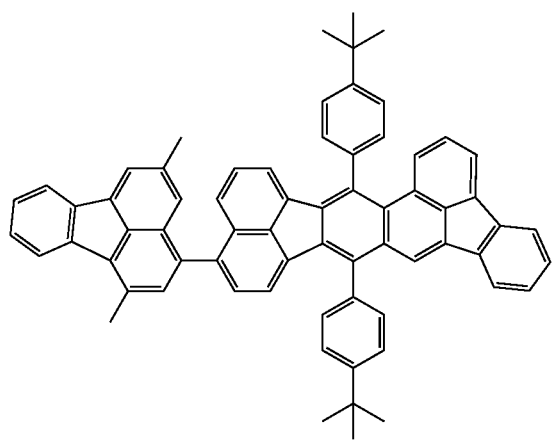
A145
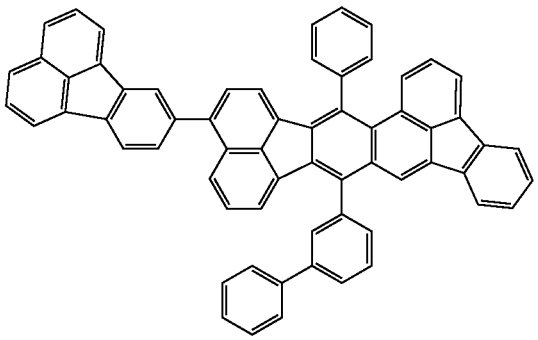
A146
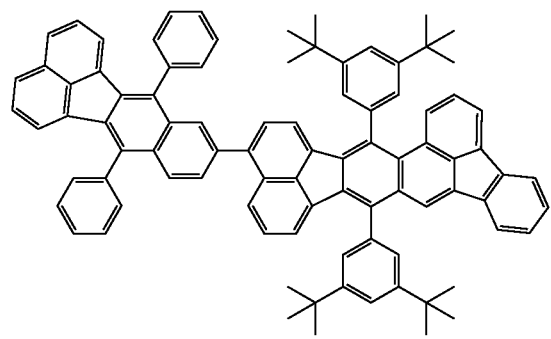
A147
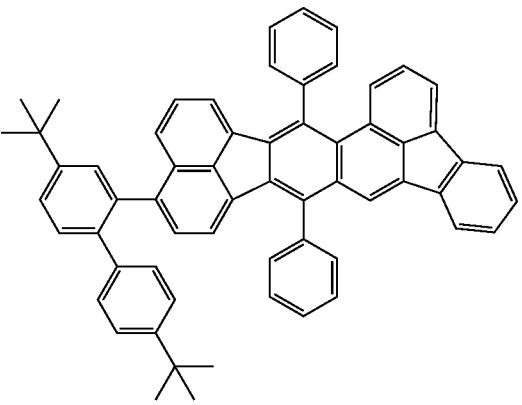
A148
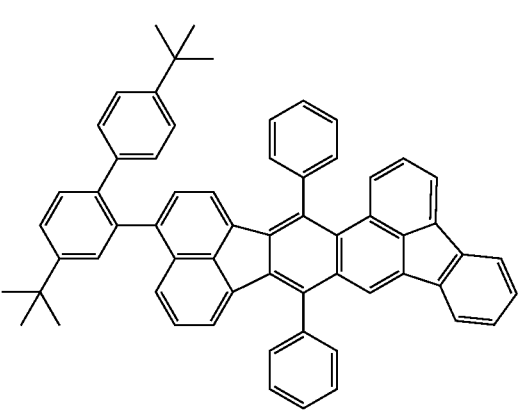
A149
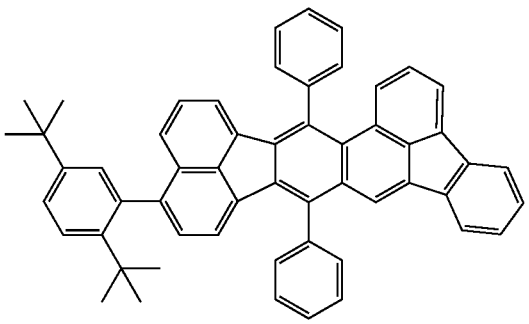
A150
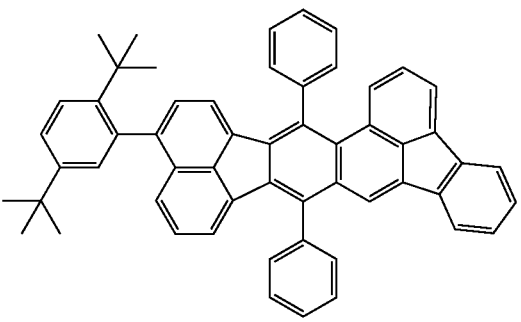

A151
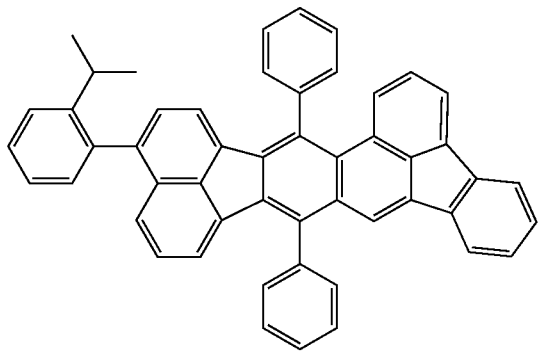
A152
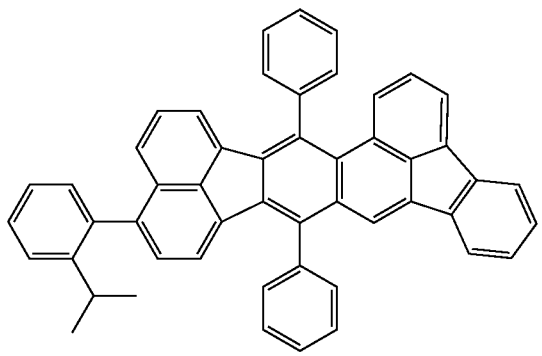
A153
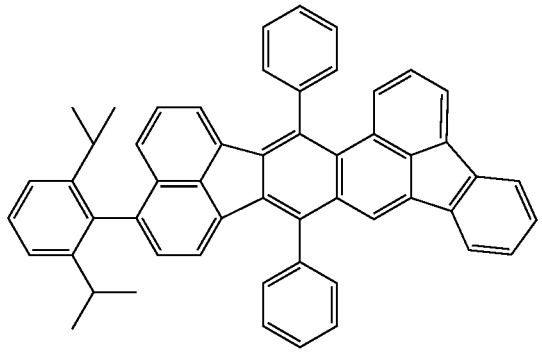
A154
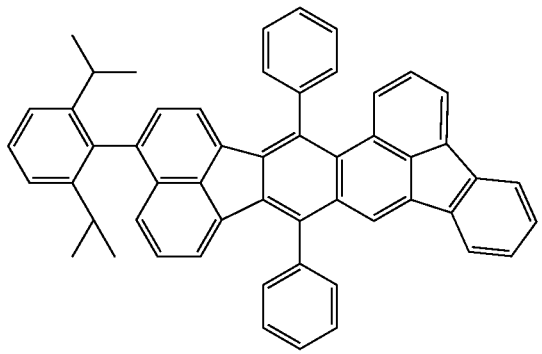
A155
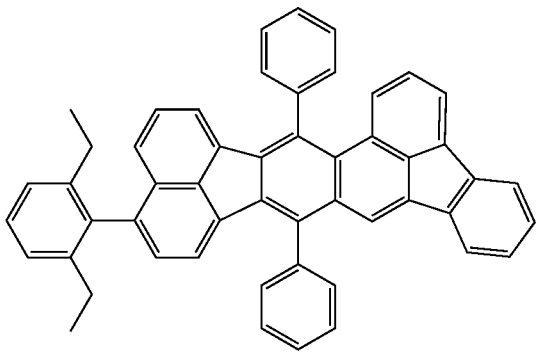
A156
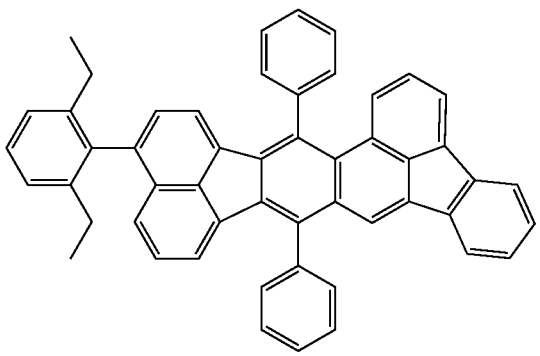
A157
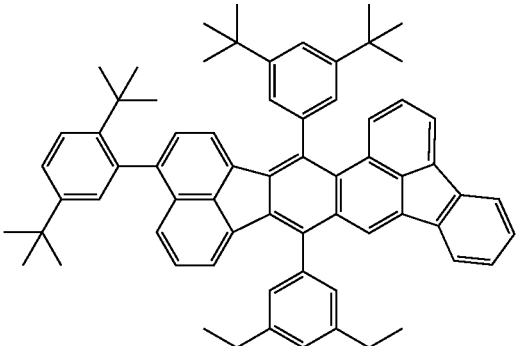
A158
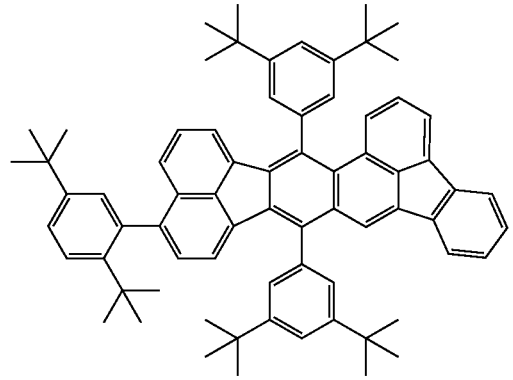

A159
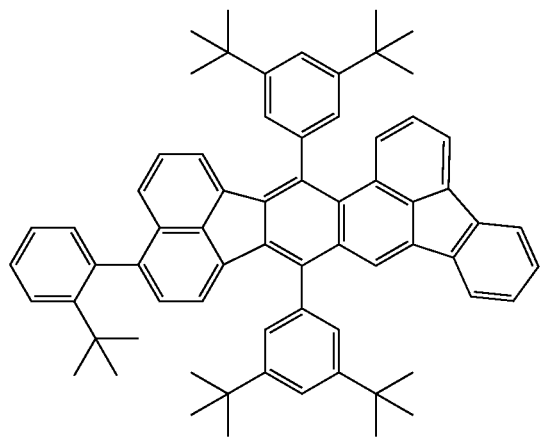
A160
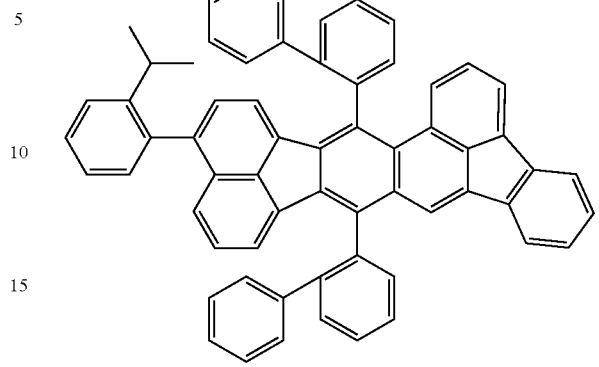
A161
A162
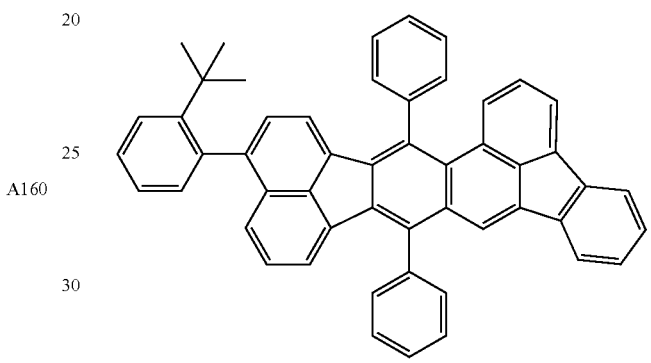
A163
A164
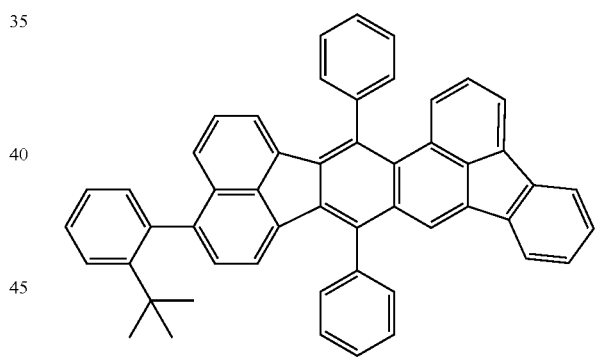
B1
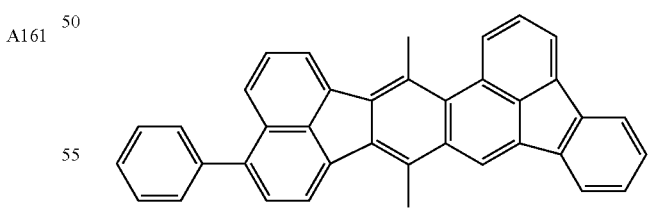
B2
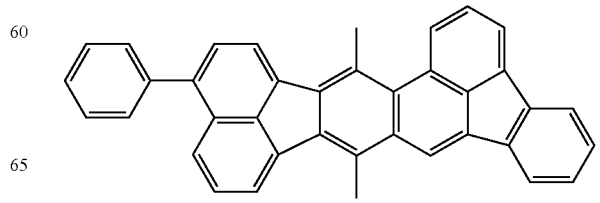

-continued
B3
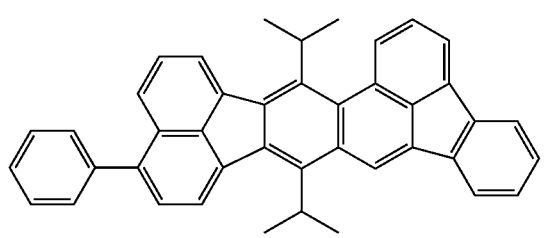
B4
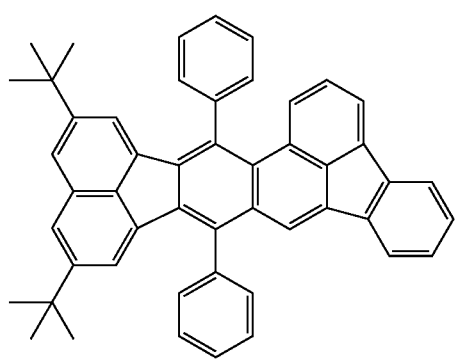
B5
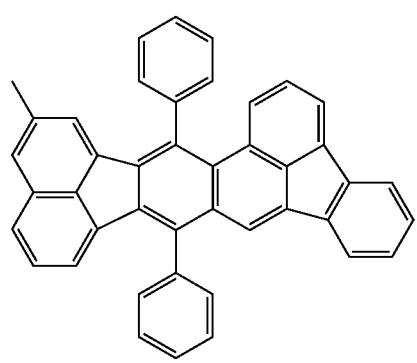
B6
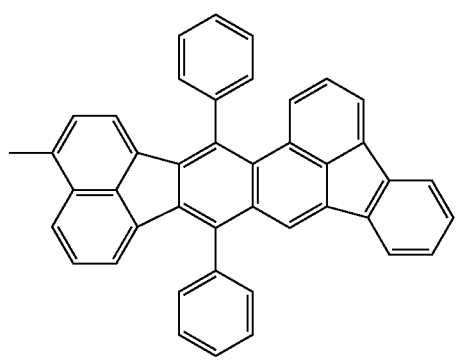
-continued
B7
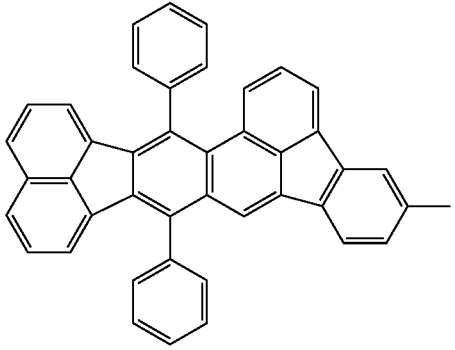
B8
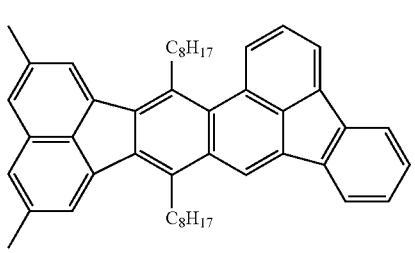
B9
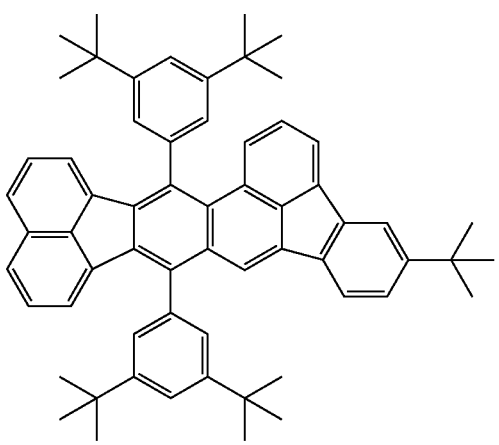
B10
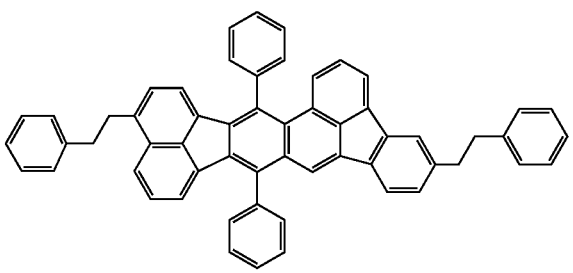

-continued
B11
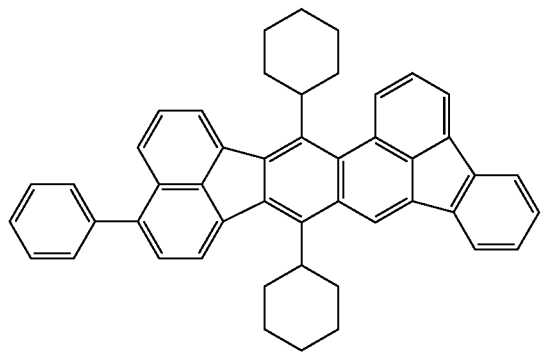
B12
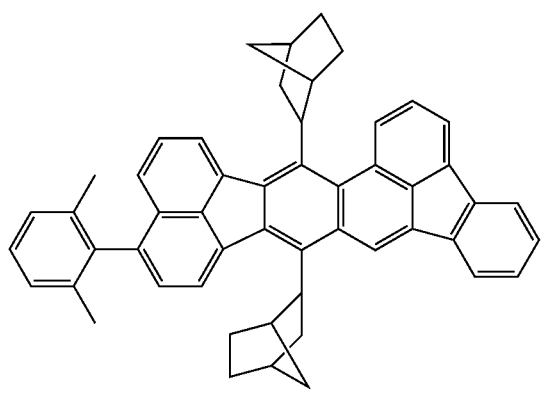
B13
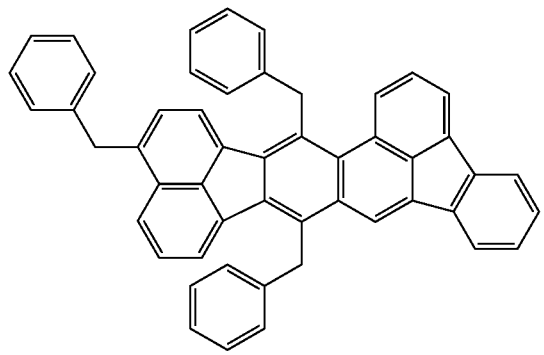
B14
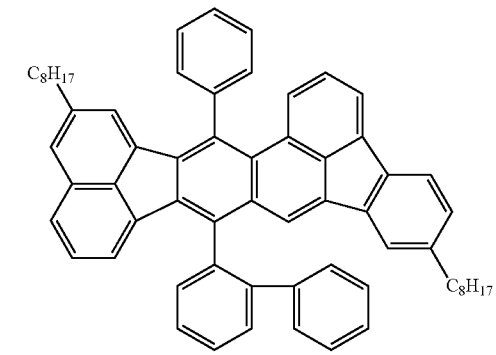
-continued
B15
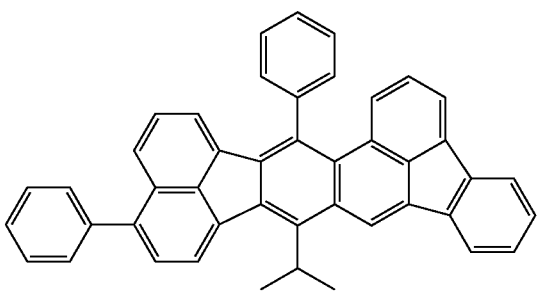
B16
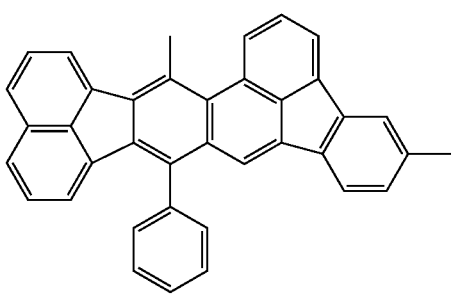
B17
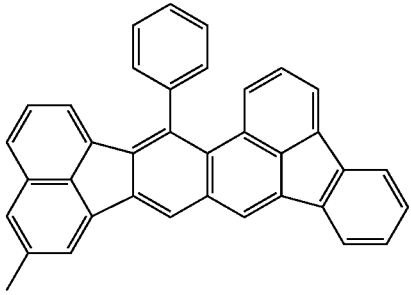
B18
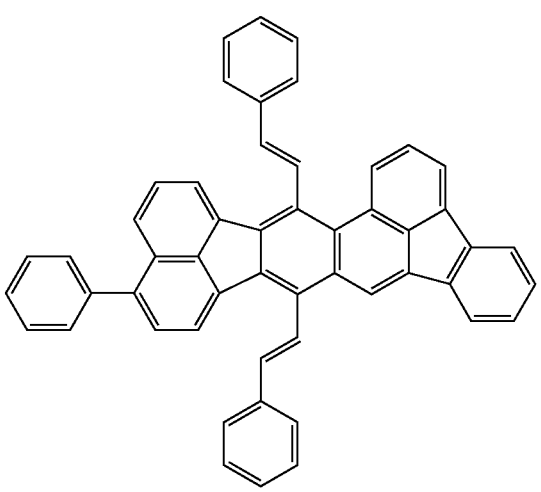

-continued
B19
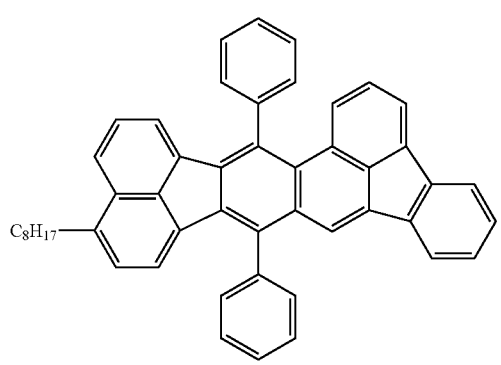
B20
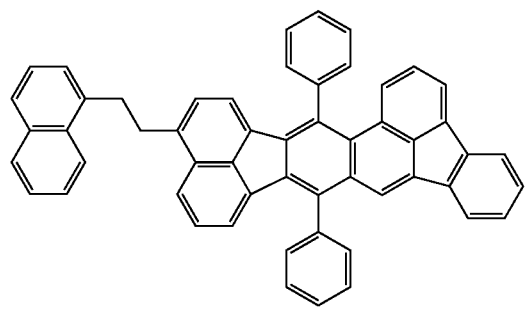
B21
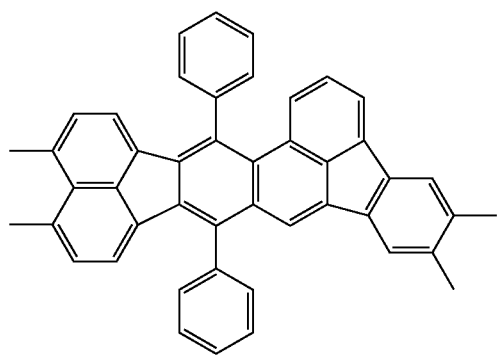
B22
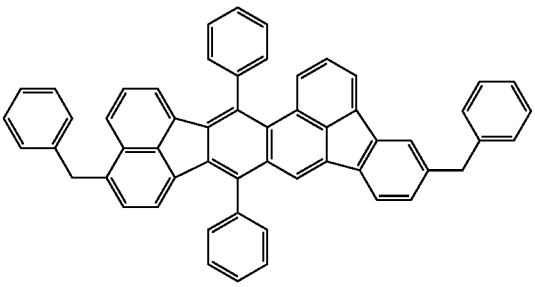
-continued
B23
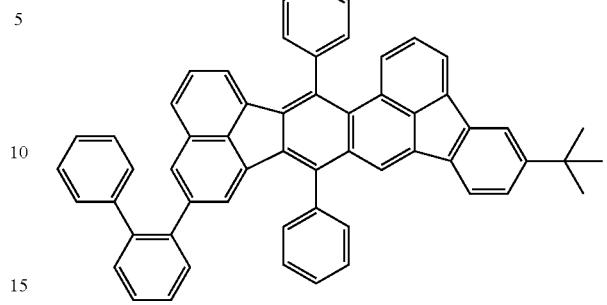
B24
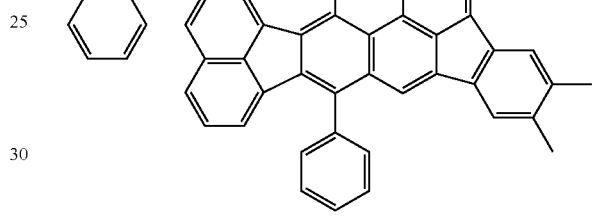
B25
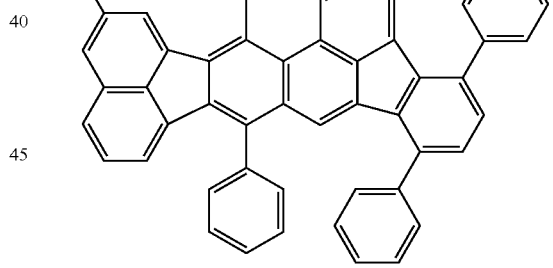
B26
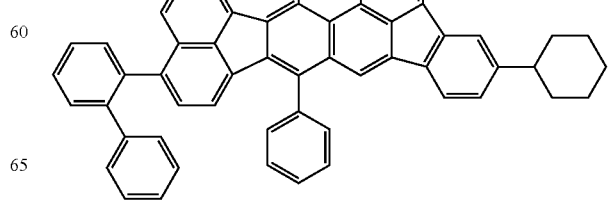

-continued
B27
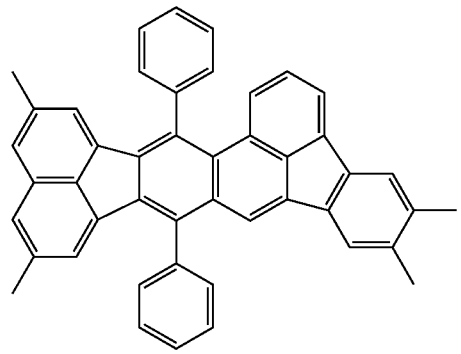
B28
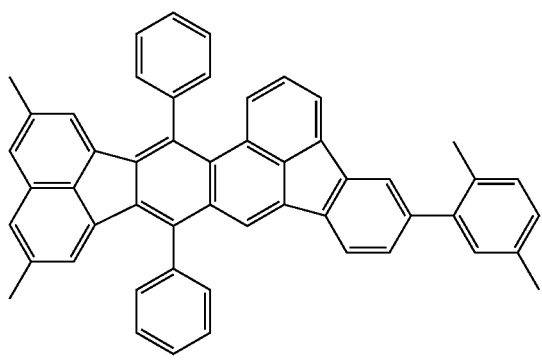
B29
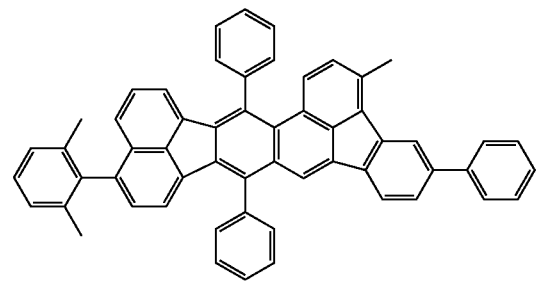
B30
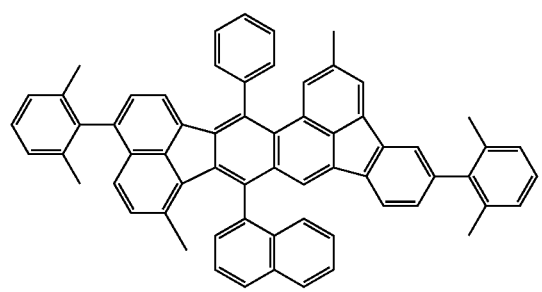
-continued
B31
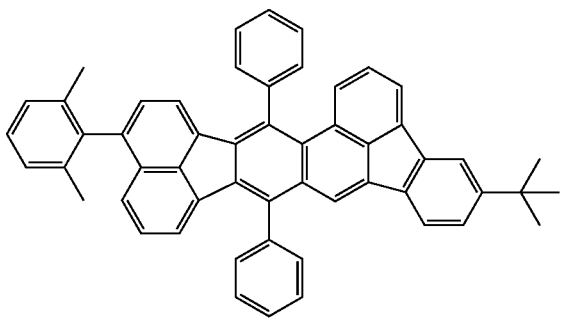
B32
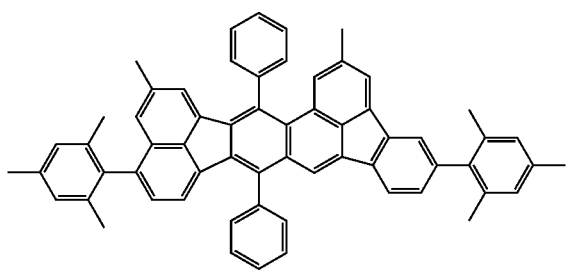
B33
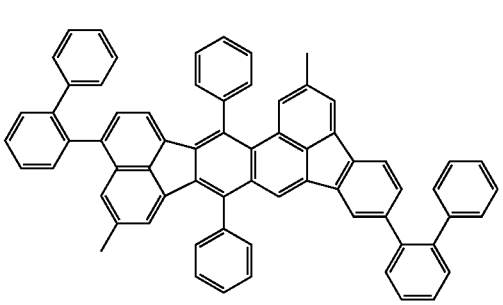
B34
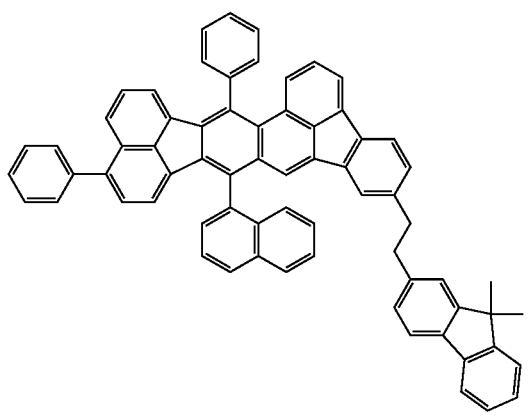

B35
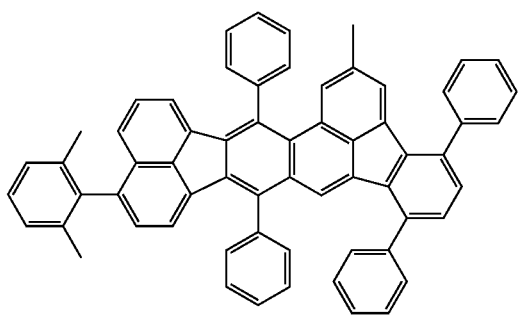
B36
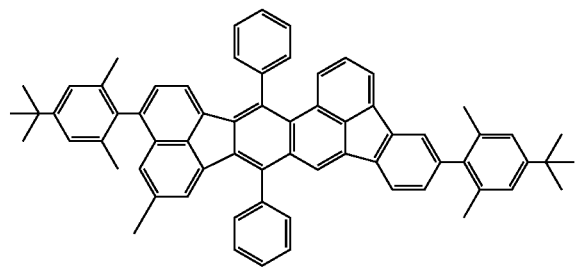
B37
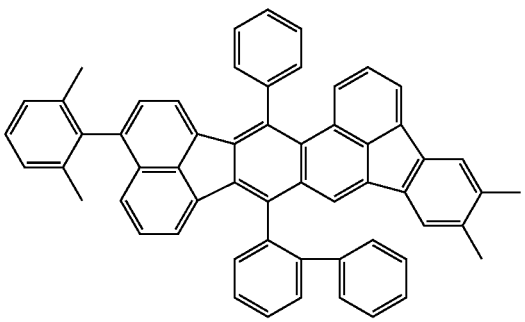
C1
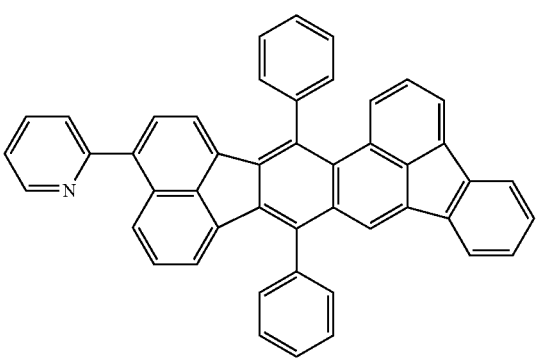
C2
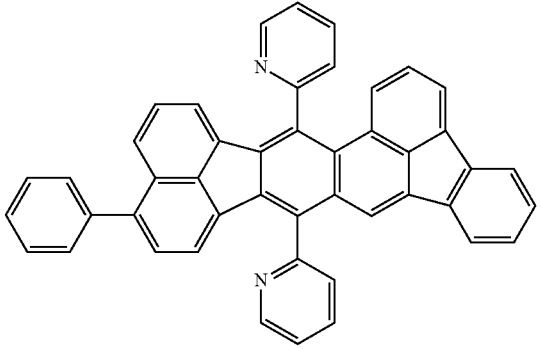
C3
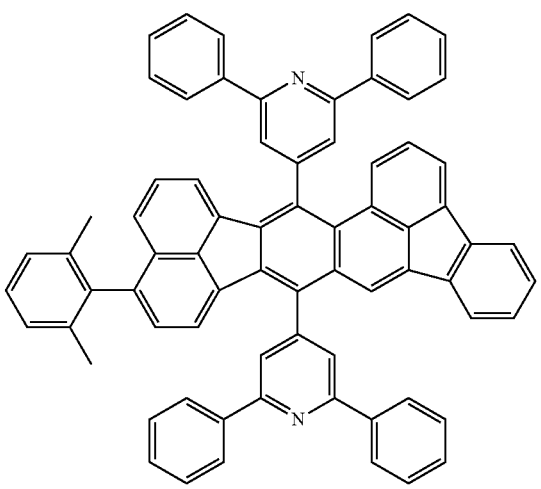
C4
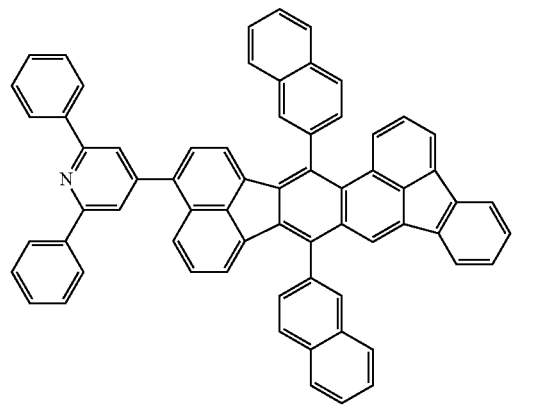
C5
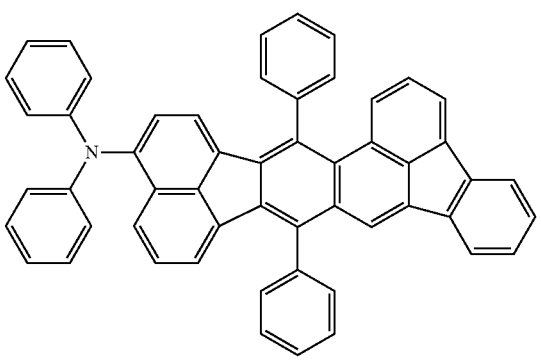

C6
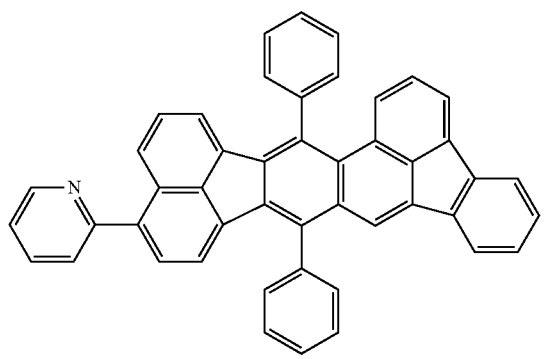
C7
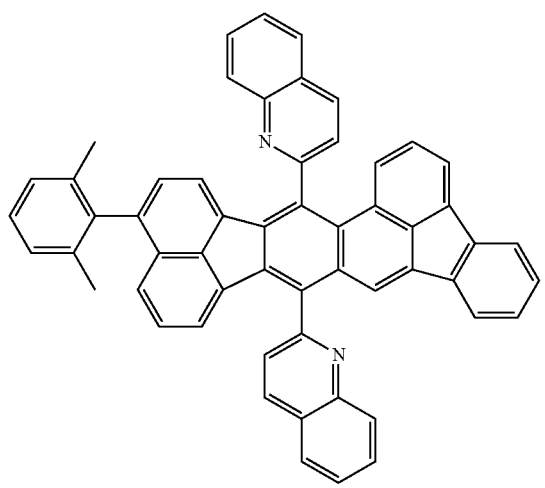
C8
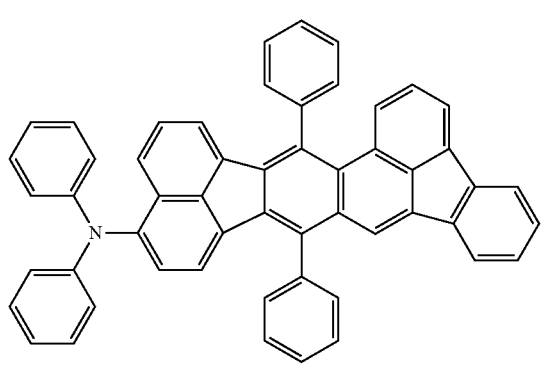
C9
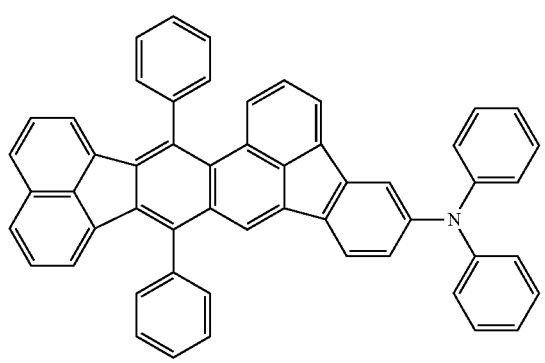
C10
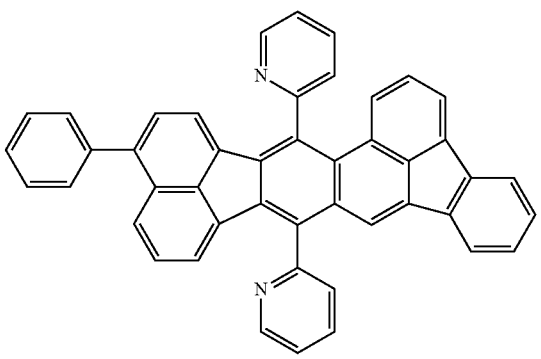
C11
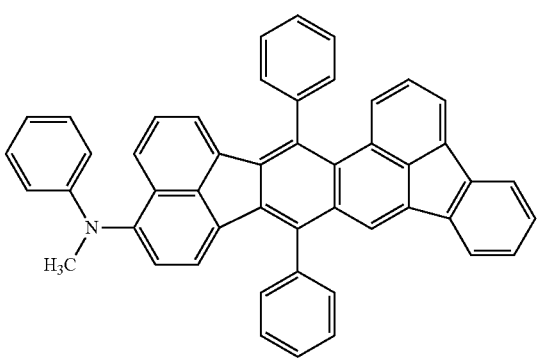
C12
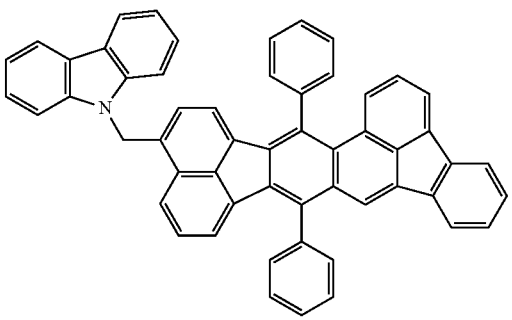
C13
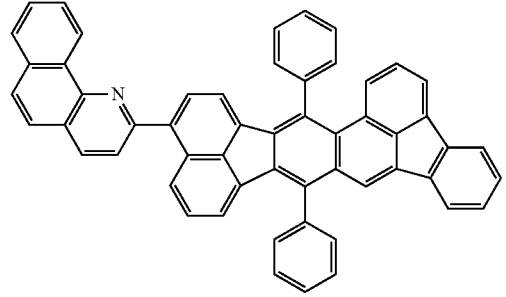

-continued
C14
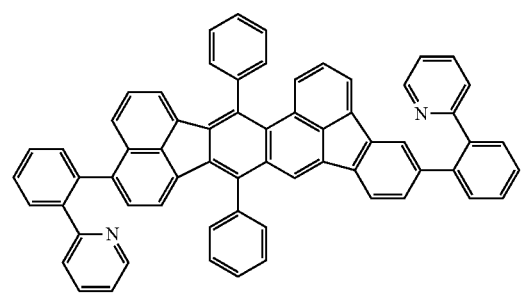
C15
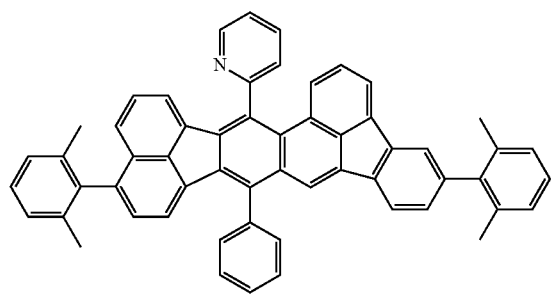
C16
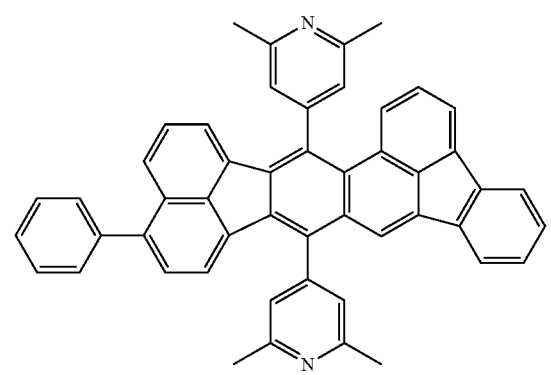
C17
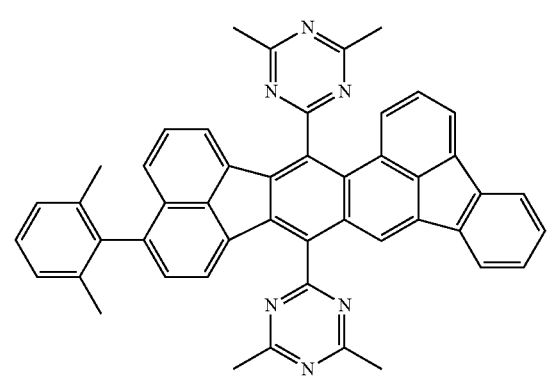
-continued
C18
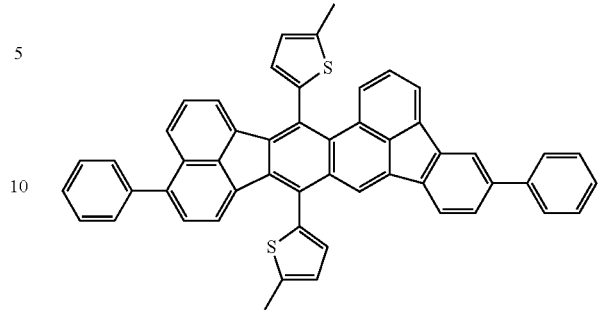
C19
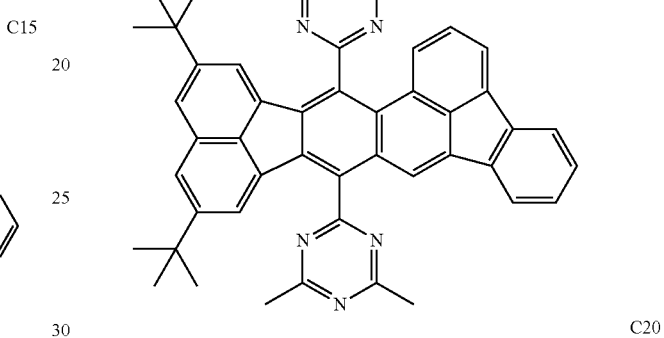
C20
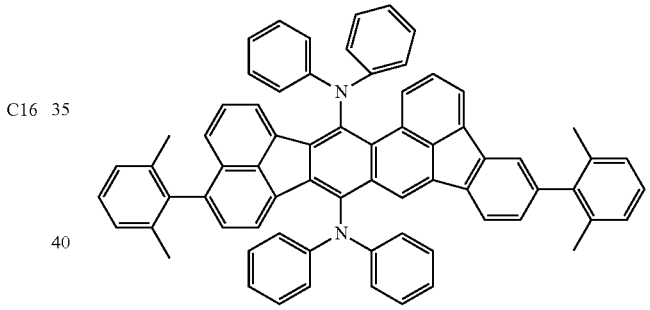
C21
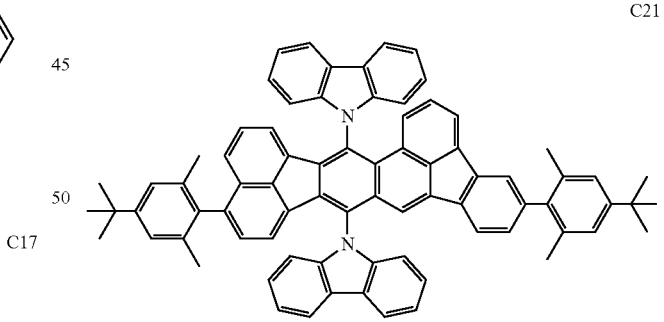
C22
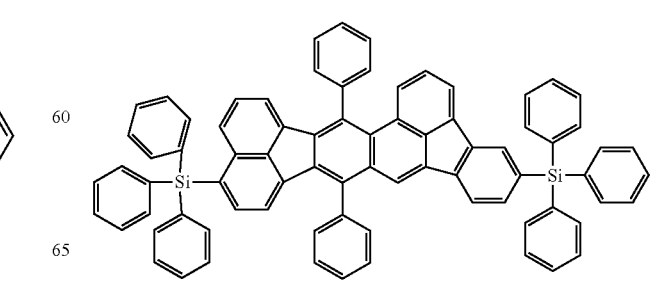

C23
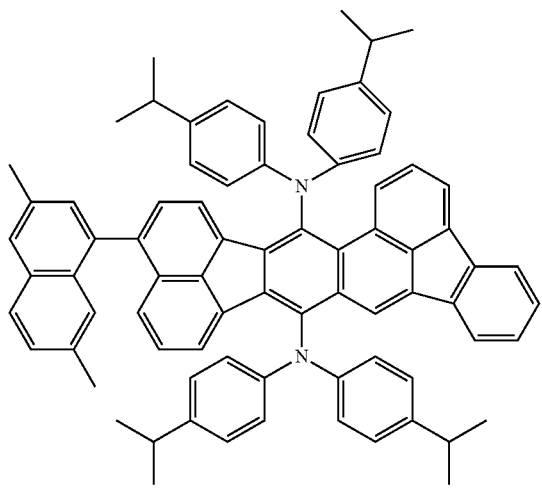
C24
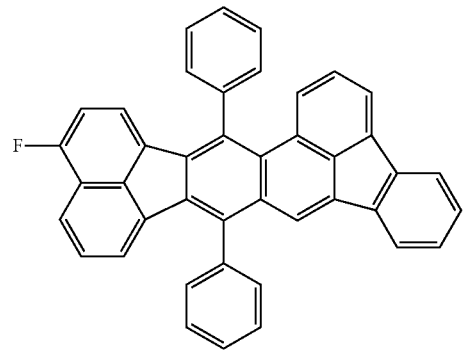
C25
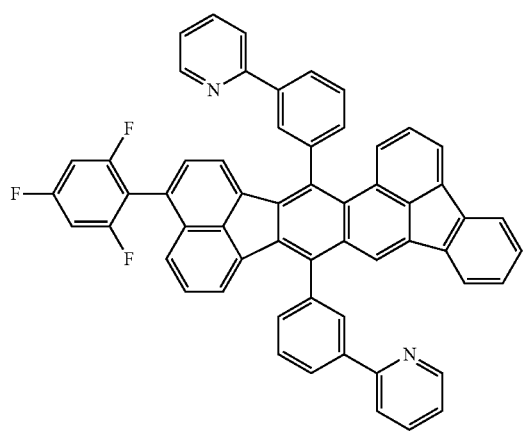
C26
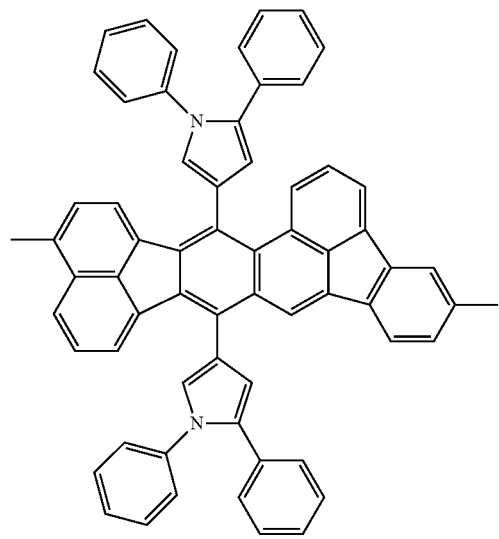
C27
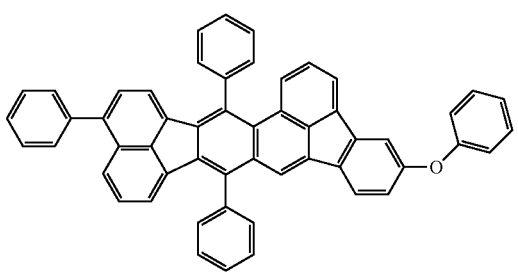
C28
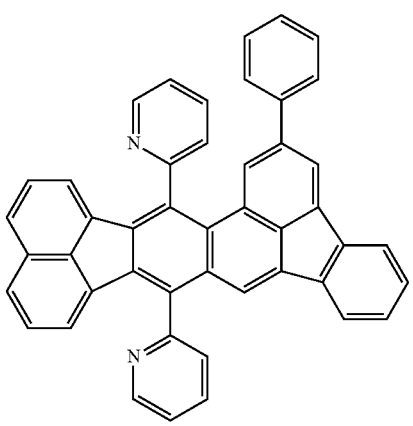
C29
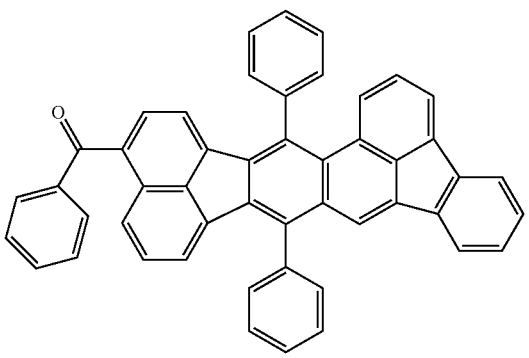

C30

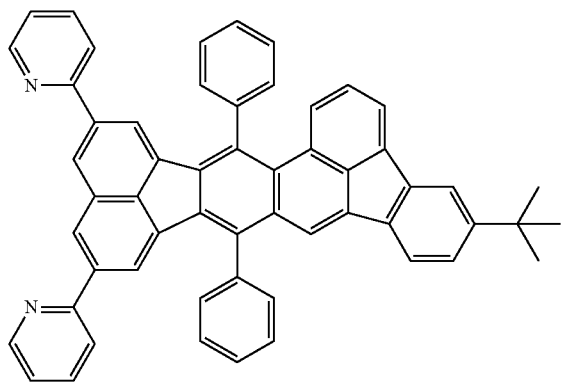

C31

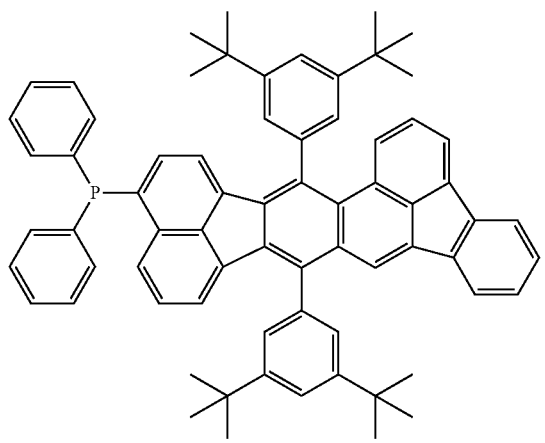

C32

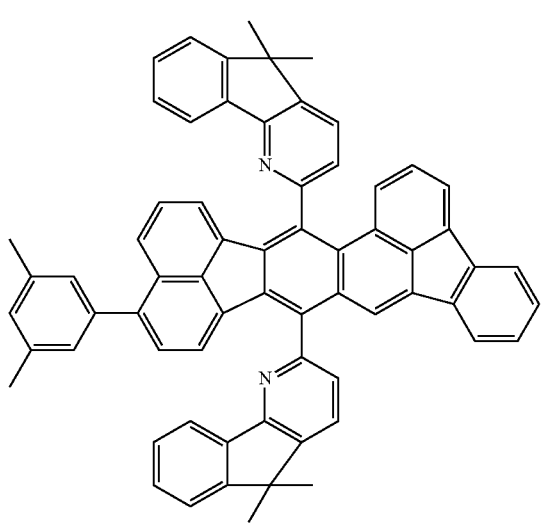

C33

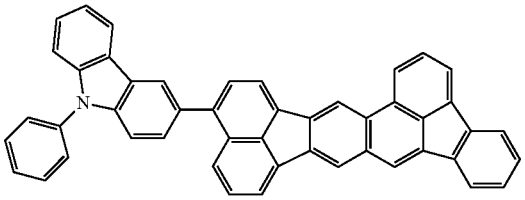

The novel organic compounds according to the present invention will now be described in more detail.

In general, in order to increase the luminous efficiency of organic light-emitting devices, it is desirable that a luminescence center material have a high emission quantum yield. In order to achieve this, it is necessary to satisfy the following conditions:

(1) The oscillator strength is high.

(2) An oscillating portion of the skeleton related to light emission is small.

As for a physical property required for a material suitable for blue-light emission in organic EL displays, it is important for a luminescent material to have an emission peak in the range of 430 to 480 nm. The organic compounds according to the present invention can emit light having an emission peak in the range of 430 to 480 nm.

As for (1) above, it is important to increase the symmetry of the molecular skeleton related to the light emission. However, under a forbidden transition condition specific to highly symmetric molecules, light emission does not occur in some cases. Alternatively, by further extending conjugation with a direction in which the conjugate plane is the longest as an axis, the dipole moment of the molecule is increased to increase the oscillator strength. In this respect, the organic compounds according to the present invention have a fused-ring structure in which conjugation is extended from the 8-position to the 11-position of benzo[k]fluoranthene. This structure further increases the moment of benzo[k]fluoranthene. As a result, the organic compounds according to the present invention have structures with high oscillator strengths.

As for (2) above, when the skeleton related to the light emission does not have a rotational structure, a decrease in the quantum yield due to rotational oscillation can be suppressed.

Furthermore, the basic skeleton of the organic compounds according to the present invention, i.e., the acenaphtho[1,2-k]benzo[e]acephenanthrene skeleton itself has a maximum emission wavelength in the blue region.

Furthermore, since this basic skeleton does not have a rotational structure, a decrease in the quantum yield due to rotational oscillation can be suppressed. A description will be made using benzo[k]fluoranthene as an example of a comparative basic skeleton. Comparing 7,12-diphenylbenzo[k]fluoranthene, which is obtained by substituting each of the 7-position and the 12-position of benzo[k]fluoranthene with a phenyl group, to 9,16-diphenylacenaphtho[1,2-k]benzo[e]acephenanthrene of the present invention, which is obtained by substituting each of the 9-position and the 16-position of acenaphtho[1,2-k]benzo[e]acephenanthrene with a phenyl group, the former compound has a maximum emission wavelength of 428 nm, whereas the compound of the present invention has a maximum emission wavelength of 440 nm.

[Chem. 3]

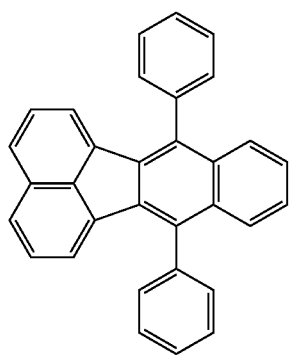

7,12-Diphenylbenzo[k]fluoranthene

[Chem. 4]

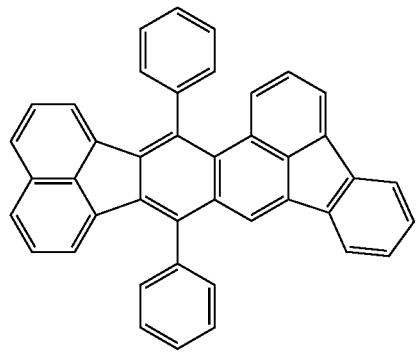

9,16-Diphenylacenaphtho[1,2-k]benzo[e]acephenanthrene

Accordingly, even the basic skeleton of the compounds of the present invention alone has an emission wavelength suitable for blue-light emission, and in addition, a high quantum yield is achieved. Furthermore, since the organic compounds according to the present invention each have two five-membered ring structures in the skeleton thereof, they have low energy levels of the HOMO and LUMO. Compounds having a lower oxidation potential require larger energy to be oxidized. That is, the organic compounds according to the present invention are stable against oxidation. When the organic compounds according to the present invention are used as luminescent materials, the compounds are suitable as electron-trapping luminescent materials.

Furthermore, according to the organic compounds of the present invention, in order to adjust the wavelength to be suitable for a desired device, a method of adjusting the wavelength by introducing a substituent may be employed. As for substituents suitable for shifting the wavelength to the long-wavelength side, the substituents are preferably introduced into the 1-position to the 8-position and the 10-position to the 15-position because substituents at the 9-position and the 16-position do not significantly change the wavelength. Absorption values (S1) of the acenaphtho[1,2-k]benzo[e]acephenanthrene skeleton and substituted acenaphtho[1,2-k]benzo[e]acephenanthrene derivatives each having an aryl group at different bonding positions were calculated. A change in the maximum emission wavelength can be estimated by the absorption values. As for the calculation method, a quantum chemical calculation at the B3LYP/6-31G* level was performed using the density function theory. Table 1 shows the results.

TABLE 1

| | Structural formula | Absorption value (S1) |
|---|---|---|
| Unsubstituted | | 411.5 nm |
| Substituted with phenyl at 5-position | | 422.1 nm |

TABLE 1-continued

| | Structural formula | Absorption value (S1) |
|---|---|---|
| Substituted with phenyl at 9-position | | 413.4 nm |
| Substituted with phenyl at 12-position | | 419.5 nm |
| Substituted with phenyl at 15-position | | 420.1 nm |
| Substituted with phenyl at 16-position | | 411.7 nm |

Although all positions of substitution were not calculated, at the 9-position and the 16-position, the absorption value was increased by 0.5 to 1.9 nm as compared with that of the unsubstituted compound, and thus the wavelength is hardly shifted to the long-wavelength side. In contrast, at the other positions, the absorption value was increased by 8.0 to 10.6 nm, as compared with that of the unsubstituted compound. Accordingly, in order to shift the wavelength to the long-wavelength side in the wavelength control, substituents at the 1-position to the 8-position and the 10-position to the 15-position are preferable. According to the present invention, by introducing substituents into the 1-position to the 8-position and the 10-position to the 15-position, the emission wavelength can be shifted to the long-wavelength side to prepare luminescent materials suitable for blue, or green to red. In addition, the organic compounds according to the present invention have high planarity. Therefore, when the organic compounds are unsubstituted, excimers are readily formed by intermolecular stacking. Accordingly, in view of suppression of the formation of excimers, an aryl group is preferably introduced to each of the 9-position and the 16-position.

A1 to A164 are compounds each constituted by only carbon atoms and hydrogen atoms. That is, these compounds do not contain a heteroatom such as nitrogen. Furthermore, each of the 9-position and the 16-position of A1 to A164 is substituted with an aryl group. Specifically, this aryl group is a phenyl group or other aryl group constituted by only carbon atoms and hydrogen atoms (hereinafter referred to as "hydrocarbon"). Since these positions are substituted with the aryl groups, these compounds have steric hindrance. Furthermore, at least one of the 1-position to the 8-position and the 10-position to the 15-position of A1 to A164 is substituted with an aryl group. Specifically, this aryl group is also a phenyl group or other aryl group constituted by only carbon atoms and hydrogen atoms. Since at least one of these positions is substituted with such an aryl group, the emission wavelength of the molecule is made longer than the emission wavelength of the basic skeleton. The aryl group bonded to each of the 9-position and the 16-position and the aryl group bonded to at least one of the 1-position to the 8-position and the 10-position to the 15-position may be the same or different.

Conjugation of the basic skeleton is extended by introducing an aryl group into at least one of these positions. As a result, since the band-gap of the molecule is narrowed, the substituted compound can emit light having a wavelength longer than the emission wavelength of the basic skeleton itself, which is an unsubstituted compound. In addition, since the 9-position and the 16-position are orthogonal to the basic skeleton, molecules having substituents at these positions have a three-dimensional structure. As a result, stacking of the molecules can be suppressed to suppress concentration quenching. Accordingly, tuning of the emission wavelength can be achieved by introducing substituents into the 1-position to the 8-position and the 10-position to the 15-position. Furthermore, formation of an excimer can be suppressed by introducing substituents into the 9-position and the 16-position. In addition, all the substituents of the organic compounds are constituted by hydrocarbons. Accordingly, when the half of the total of the oxidation potential and the reduction potential of the basic skeleton is assumed to be a center position, the potential width of oxidation-reduction of these organic compounds can be changed while maintaining the center position.

In the organic compounds according to the present invention, when a substituent is a hydrocarbon in which an alkyl group is directly bonded, e.g., the substituent shown in any of B1 to B37, the alkyl group is directly bonded to the basic skeleton. As a result, the compound is subjected to the donating property of the substituent, the center position is shifted from the oxidation-reduction potential, and the oxidation potential tends to be high.

Furthermore, according to the organic compounds of the present invention, since a substituent having an $sp^3$ hybrid orbital is directly bonded to the basic skeleton, stacking of the molecules can be suppressed. Thus, the formation of excimer can be effectively suppressed. In addition, the formation of excimer can be further suppressed by introducing, as an additional substituent, a substituent having a fused-ring structure into an end of an alkyl group which is a substituent introduced into the basic skeleton.

In addition, when the organic compound has, as a substituent, a heteroatom-containing substituent such as a heterostructure-containing aryl group or amino group, as shown in C1 to C33, it is possible to control a change in the oxidation-reduction potential due to the heterostructure. As a result, not only the maximum emission wavelength can be shifted to the long-wavelength side and the organic compounds can be used as an electron-trapping luminescent material, but also the organic compounds can be used in applications such as an electron transport material, a hole transport material, and a hole-trapping luminescent material.

It was found that, in this respect, acenaphtho[1,2-k]benzo[e]acephenanthrene derivatives which are organic compounds according to the present invention can achieve a high quantum yield that can be used in the blue region.

As described above, according to the organic light-emitting device of the present invention, at least one acenaphtho[1,2-k]benzo[e]acephenanthrene derivative compound is contained in a layer composed of an organic compound. The acenaphtho[1,2-k]benzo[e]acephenanthrene derivative compounds of the present invention can be used as a luminescent material for a blue-light-emitting device. However, the applications of the compounds are not limited thereto. Specifically, the compounds of the present invention may be used as a luminescent material, a host material, a transport material, and the like for a green-light-emitting device.

Organic compounds represented by general formula (1) can be synthesized by synthetic route 1 described below. Although this synthesis method produces isomers depending on the position of a substituent R, there is no significant difference in the luminescence properties so long as the isomers have the same R. Accordingly, a desired compound may be isolated by recrystallization or the like and used or the isomers may be used in the form of a mixture. The mixture ratio is not particularly limited because the luminescence properties of the mixture are not significantly decreased compared with those of a single compound. When the compounds are used as a mixture, crystallinity is suppressed and thus an advantage such as suppression of concentration quenching can also be expected. As for other substituents, the synthesis can be conducted by substituting hydrogen atoms with other substituents such as an alkyl group, a halogen atom, a phenyl group, and the like.
Synthetic Route 1

Various organic compounds according to the present invention can be synthesized from starting materials D1 to D4. Organic compounds that can be synthesized are shown in the table below (synthetic compounds in Table 2 below). Table 2 also shows the starting materials.

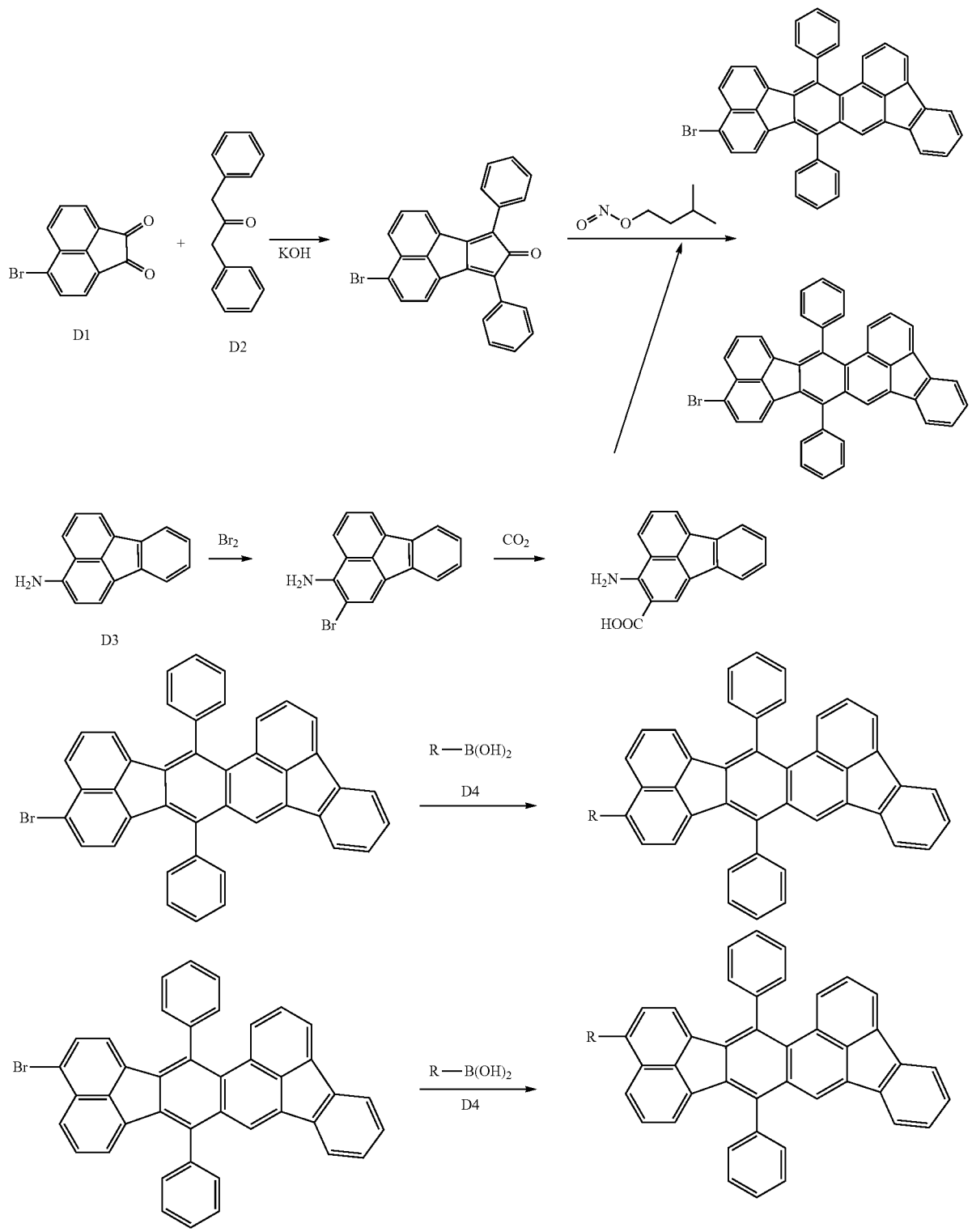

[Chem. 5]

TABLE 2

| | D1 | D2 | D3 | D4 |
|---|---|---|---|---|
| Synthesis example 1 | 5-bromoacenaphthenequinone | 1,3-diphenylacetone | 3-aminofluoranthene | phenylboronic acid |
| Synthesis example 2 | 5-bromoacenaphthenequinone | 1,3-diphenylacetone | 3-aminofluoranthene | 2,6-dimethylphenylboronic acid |
| Synthesis example 3 | 5-bromoacenaphthenequinone | 1,3-diphenylacetone | 3-aminofluoranthene | 2,4,6-trimethylphenylboronic acid |
| Synthesis example 4 | 5-bromoacenaphthenequinone | 1,3-diphenylacetone | 3-aminofluoranthene | 3,6-di-tert-butylnaphthalen-1-ylboronic acid |
| Synthesis example 5 | 5-bromoacenaphthenequinone | 1,3-diphenylacetone | 3-aminofluoranthene | [1,1':2',1''-terphenyl]-3'-ylboronic acid |
| Synthesis example 6 | 5-bromoacenaphthenequinone | 1,3-diphenylacetone | 3-aminofluoranthene | [1,1':3',1''-terphenyl]-5'-ylboronic acid |
| Synthesis example 7 | 5-bromoacenaphthenequinone | 1,3-diphenylacetone | 3-aminofluoranthene | naphthalen-1-ylboronic acid |

TABLE 2-continued
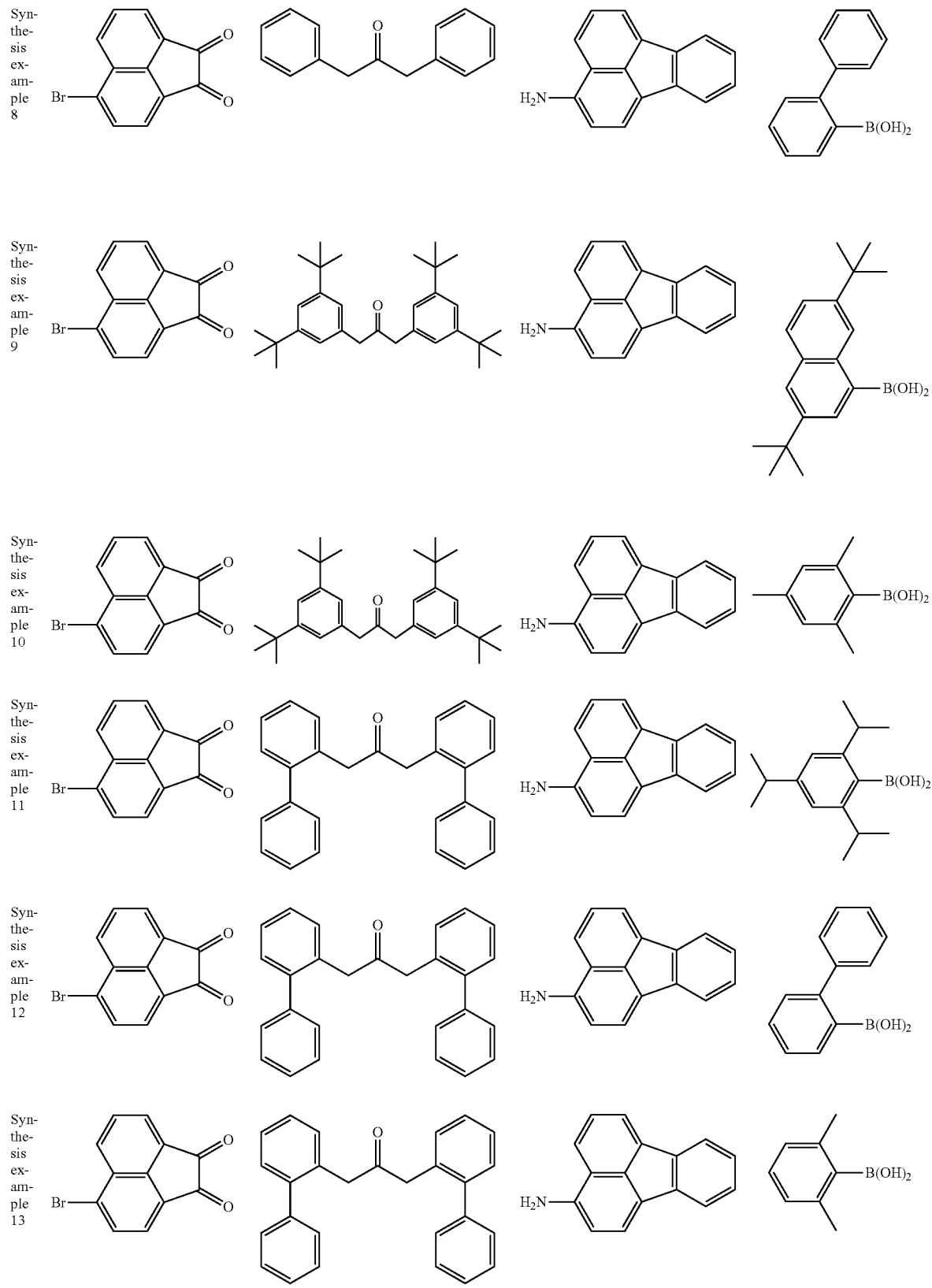

TABLE 2-continued
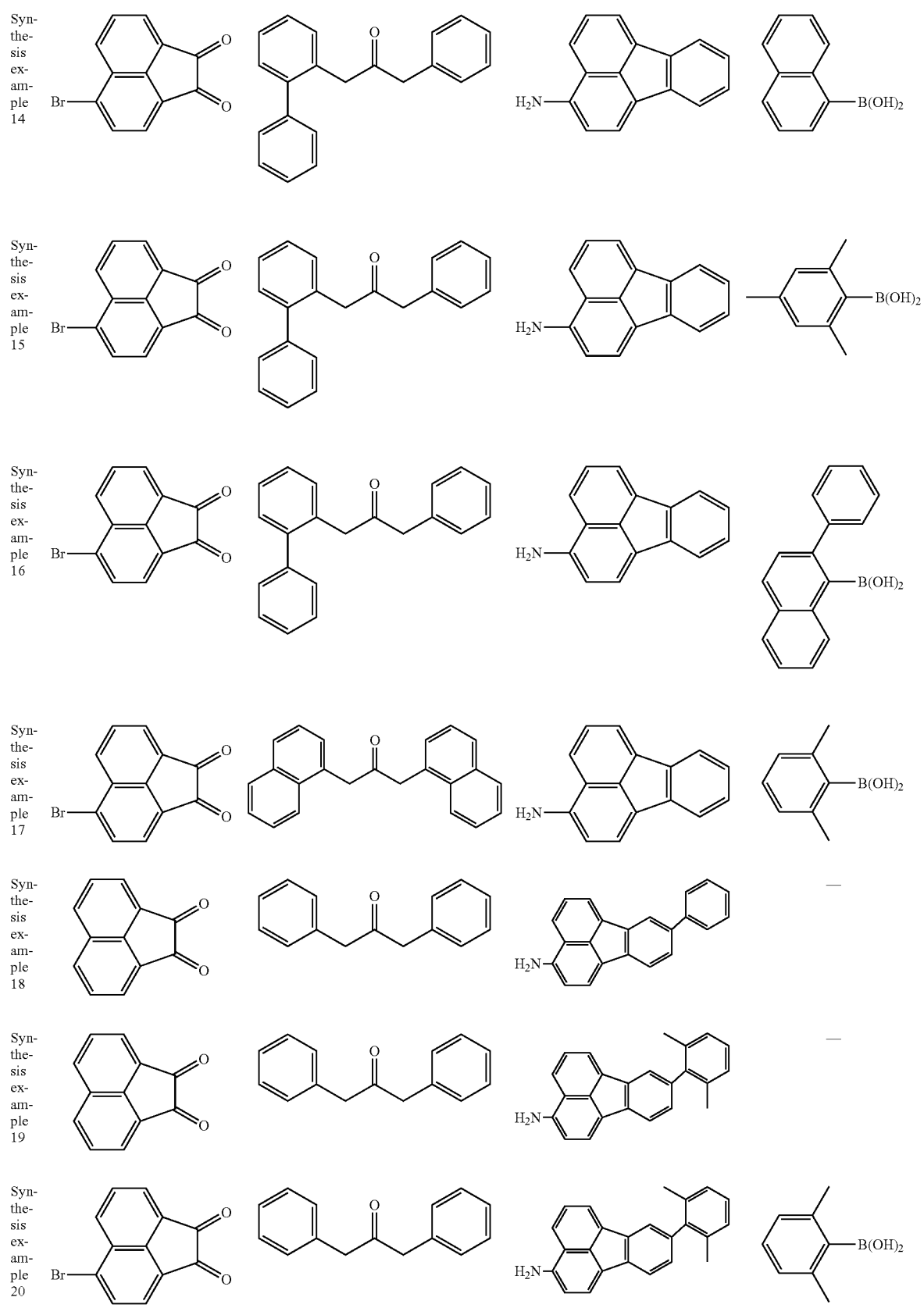

TABLE 2-continued
| Synthesis example 21 | 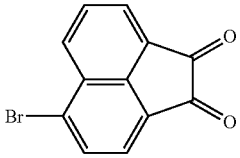 | 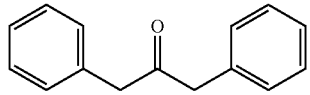 | 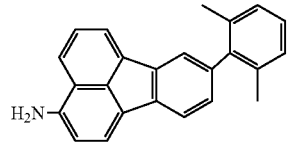 | 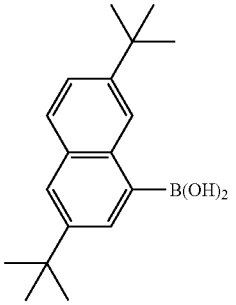 |
|---|---|---|---|---|
| Synthesis example 22 | 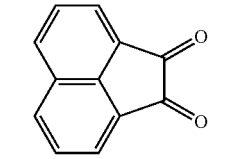 [SMILES: O=C1C(=O)c2cccc3cccc1c23] | 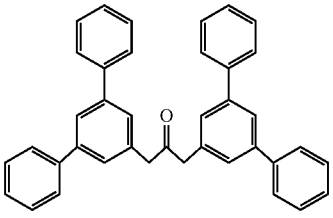 [SMILES: O=C(Cc1cc(-c2ccccc2)cc(-c2ccccc2)c1)Cc1cc(-c2ccccc2)cc(-c2ccccc2)c1] | 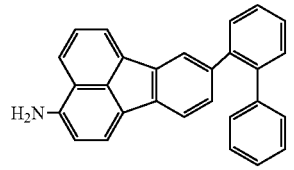 [SMILES: Nc1ccc2c3c(cccc13)-c1cc(-c3ccccc3-c3ccccc3)ccc1-2] | — |
| Synthesis example 23 | 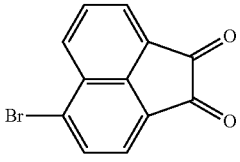 | 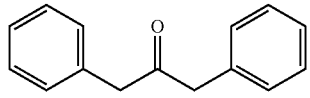 [SMILES: O=C(Cc1ccccc1)Cc1ccccc1] | 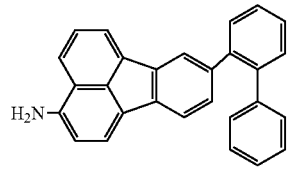 [SMILES: Nc1ccc2c3c(cccc13)-c1cc(-c3ccccc3-c3ccccc3)ccc1-2] | 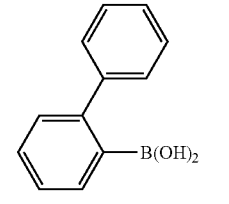 [SMILES: OB(O)c1ccccc1-c1ccccc1] |
| Synthesis example 24 | 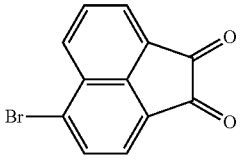 | 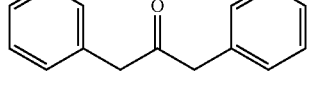 | 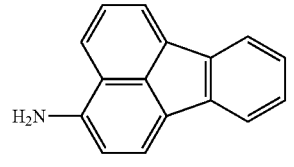 [SMILES: Nc1ccc2c3c(cccc13)-c1ccccc1-2] | 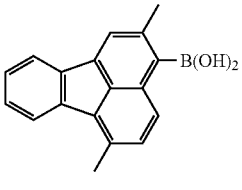 [SMILES: Cc1cc2c3c(c(C)ccc3c1B(O)O)-c1ccccc1-2] |
| Synthesis example 25 | 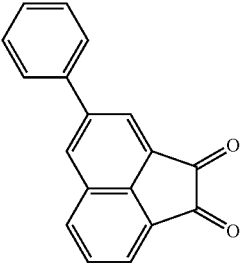 [SMILES: O=C1C(=O)c2cc(-c3ccccc3)cc3cccc1c23] | 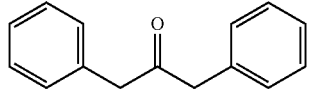 [SMILES: O=C(Cc1ccccc1)Cc1ccccc1] | 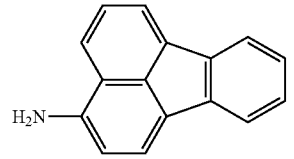 [SMILES: Nc1ccc2c3c(cccc13)-c1ccccc1-2] | — |
| Synthesis example 26 | 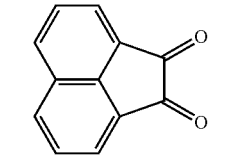 [SMILES: O=C1C(=O)c2cccc3cccc1c23] | 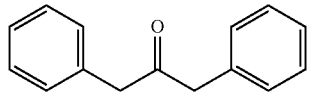 [SMILES: O=C(Cc1ccccc1)Cc1ccccc1] | 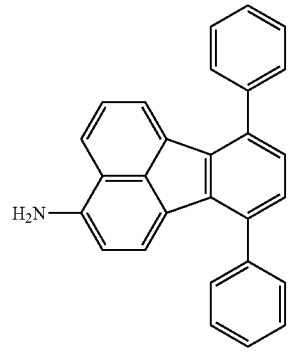 [SMILES: Nc1ccc2c3c(cccc13)-c1c(-c3ccccc3)ccc(-c3ccccc3)c1-2] | — |

TABLE 2-continued

| | | | | |
|---|---|---|---|---|
| Synthesis example 27 | | | | |
| Synthesis example 28 | | | | |
| Synthesis example 29 | | | | |
| Synthesis example 30 | | | | |
| Synthesis example 31 | | | | — |
| Synthesis example 32 | | | | |

Synthetic compounds

| | |
|---|---|
| Synthesis example 1 | |

TABLE 2-continued
Synthesis example 2
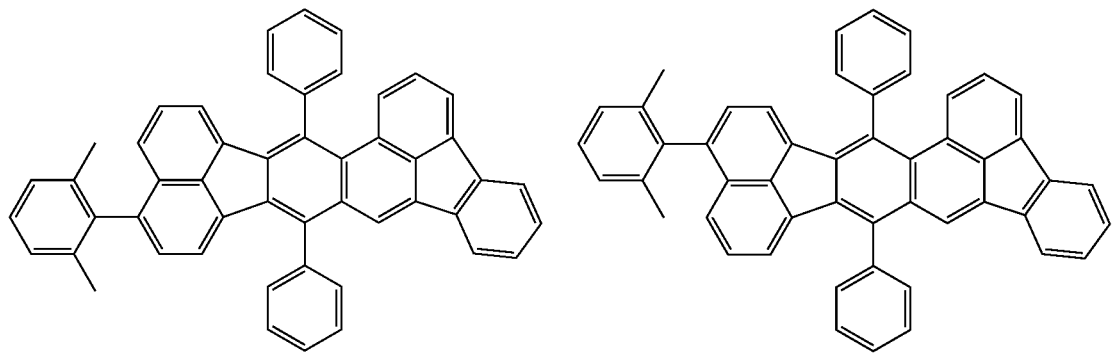
Synthesis example 3
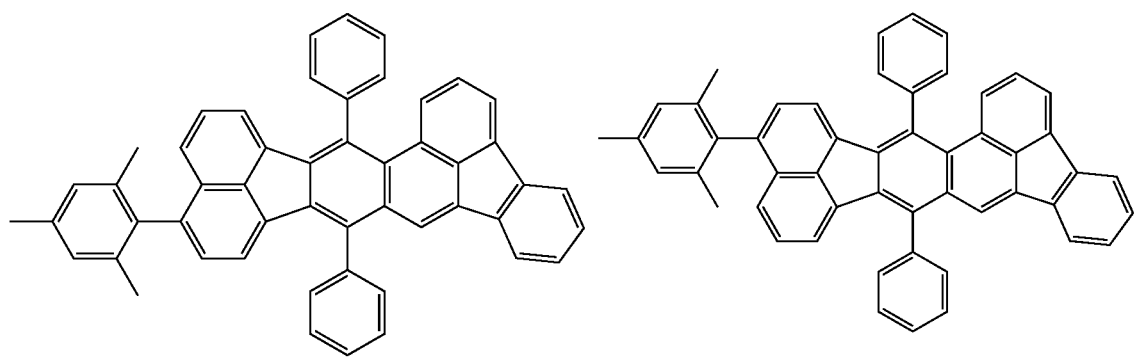
Synthesis example 4
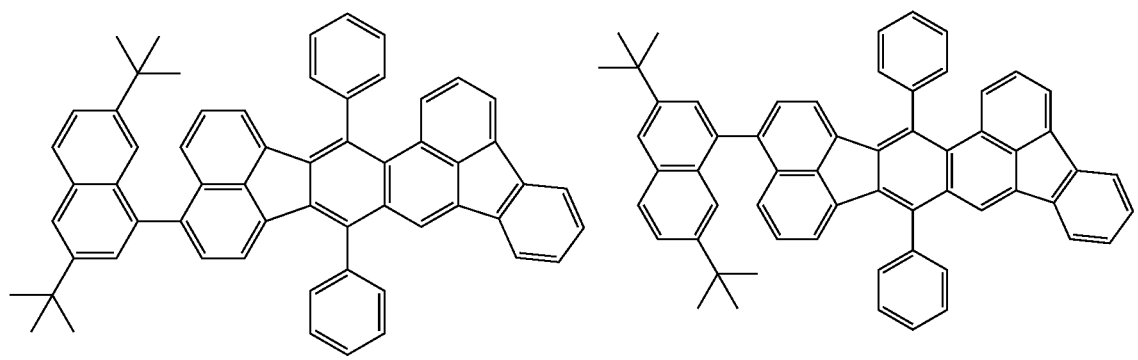
Synthesis example 5
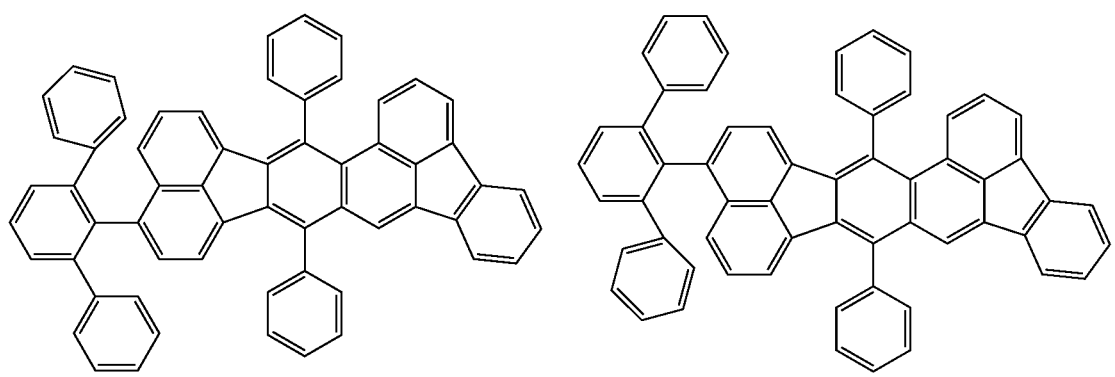

TABLE 2-continued
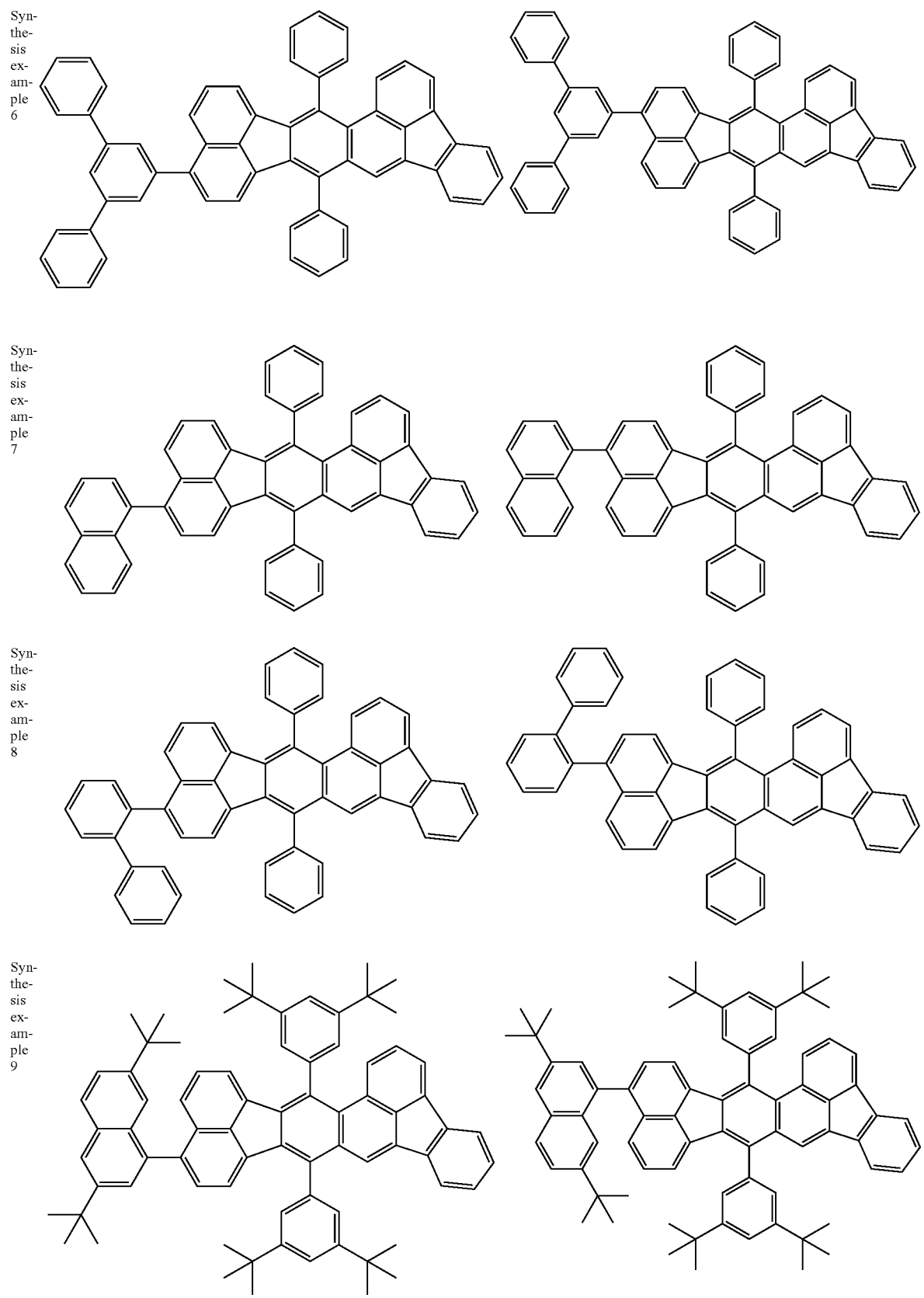

TABLE 2-continued
| | | |
|---|---|---|
| Synthesis example 10 | 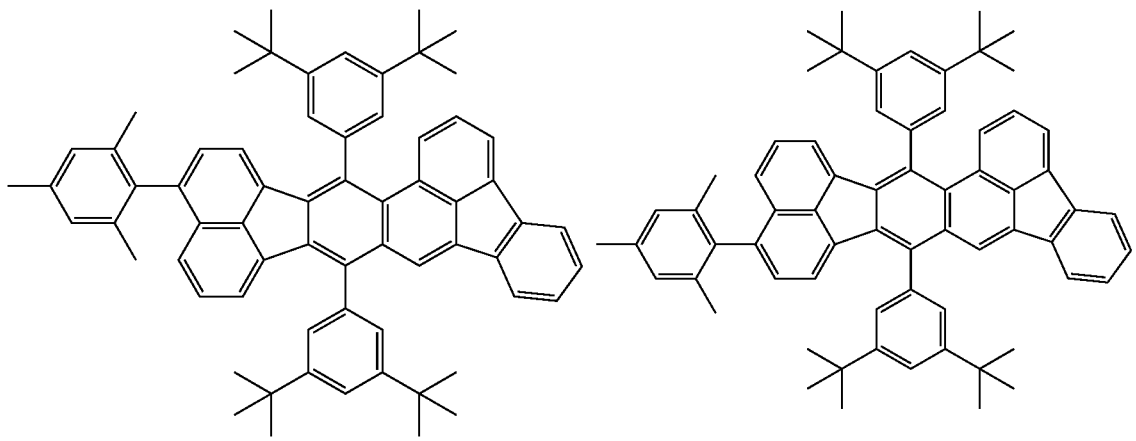 | |
| Synthesis example 11 | 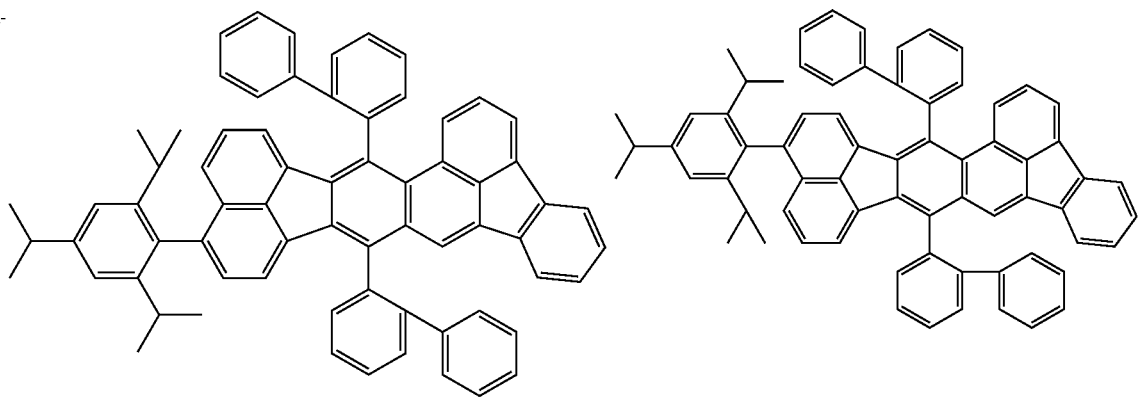 | |
| Synthesis example 12 | 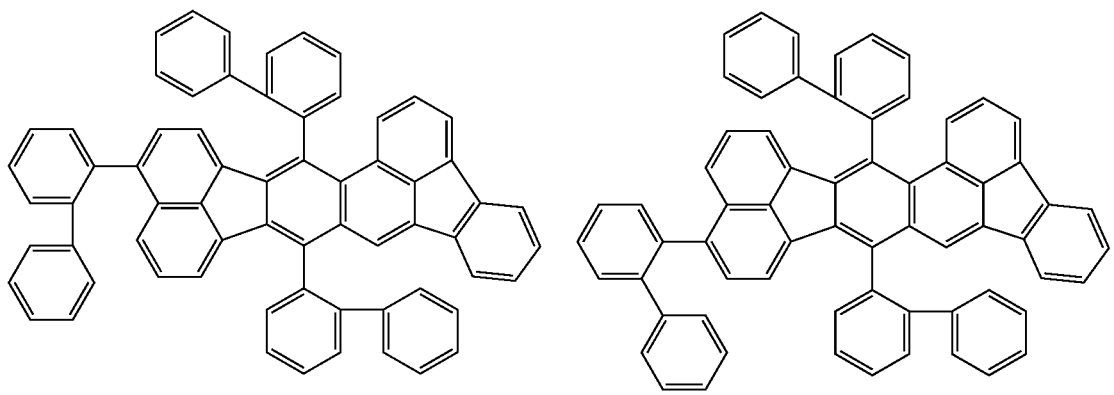 | |
| Synthesis example 13 | 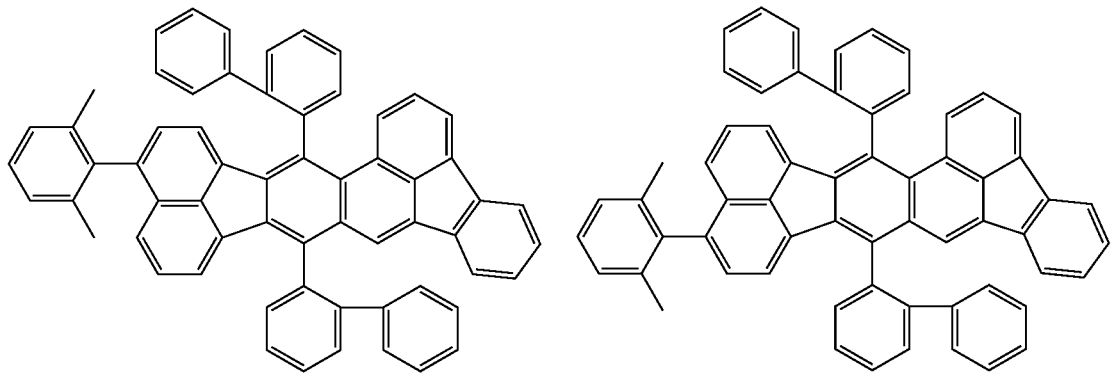 | |

TABLE 2-continued
| Synthesis example 14 | 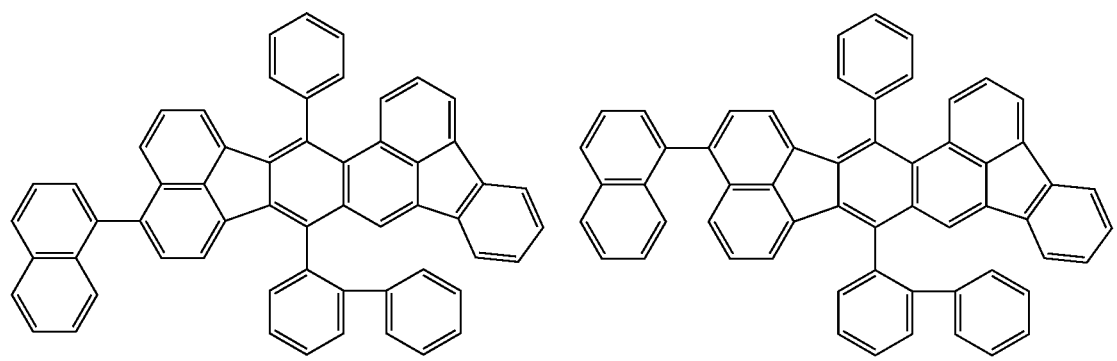 |
| --- | --- |
| Synthesis example 15 | 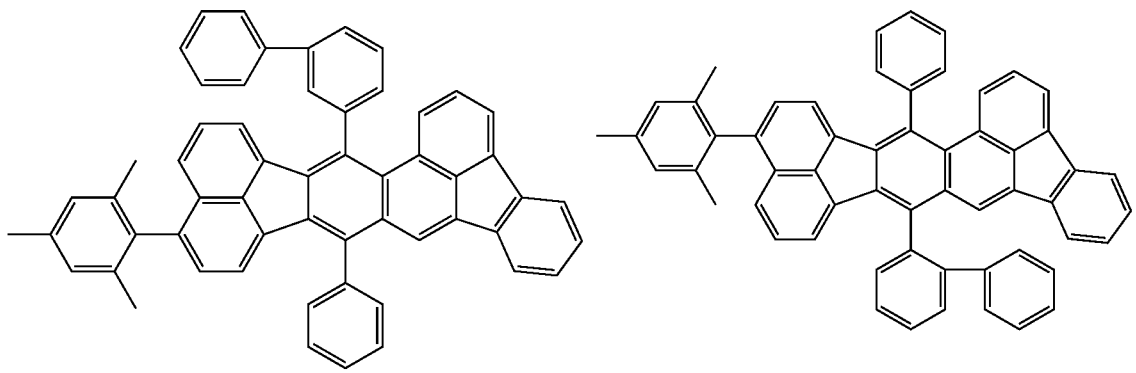 |
| Synthesis example 16 | 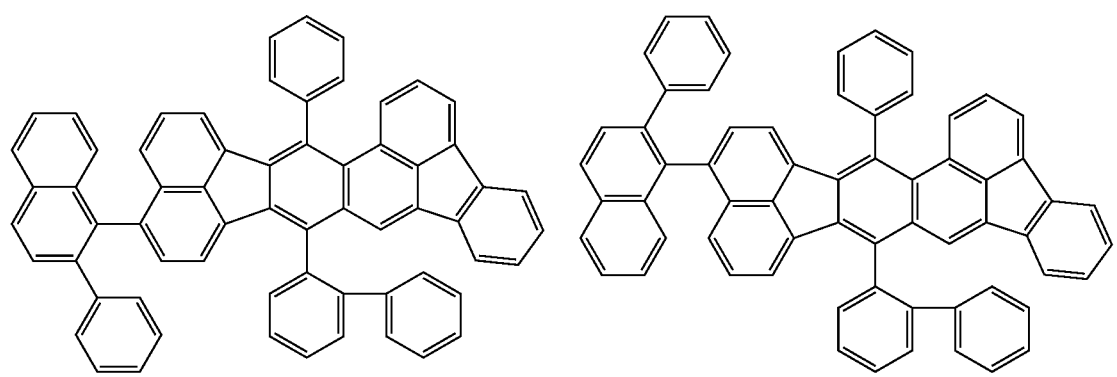 |
| Synthesis example 17 | 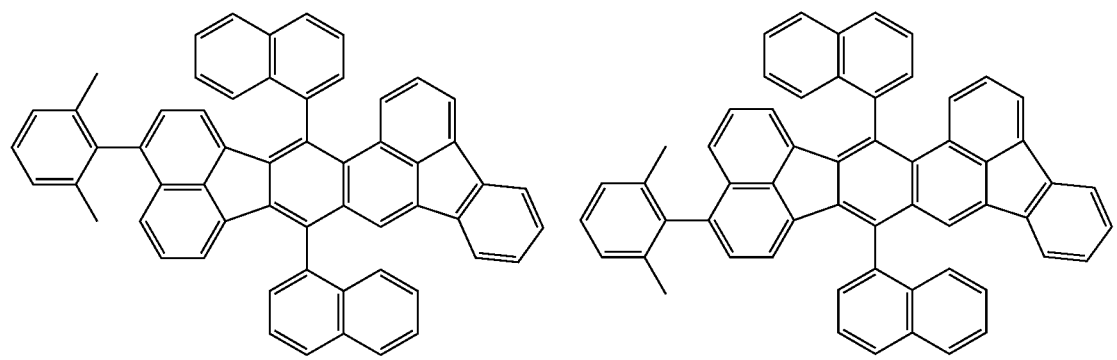 |

TABLE 2-continued
| Synthesis example 18 | 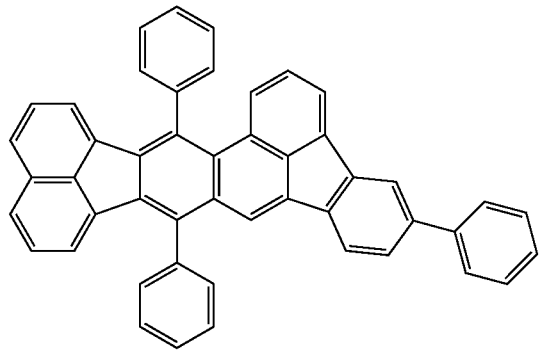 [SMILES: c1ccc(-c2ccc3c(c2)c2cccc4c5c(-c6ccccc6)c6c7cccc8cccc(c6c(-c6ccccc6)c5cc3c24)c87)cc1] |
| --- | --- |
| Synthesis example 19 | 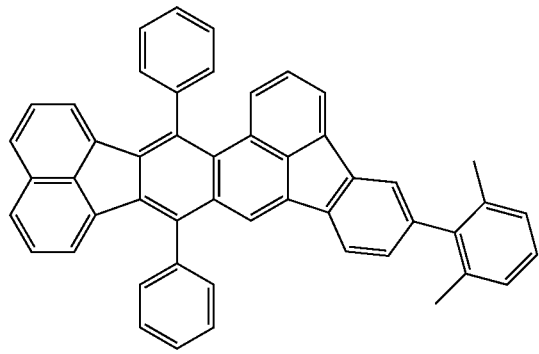 [SMILES: Cc1cccc(C)c1-c1ccc2c(c1)c1cccc3c4c(-c5ccccc5)c5c6cccc7cccc(c5c(-c5ccccc5)c4cc2c13)c76] |
| Synthesis example 20 | 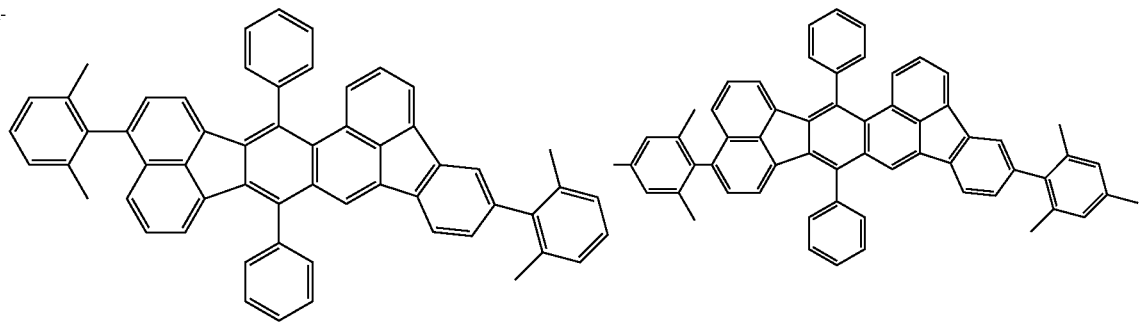 |
| Synthesis example 21 | 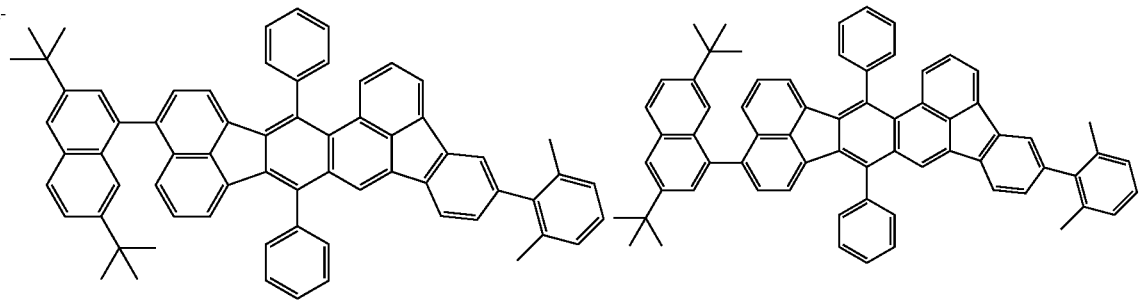 |

TABLE 2-continued
Synthesis example 22
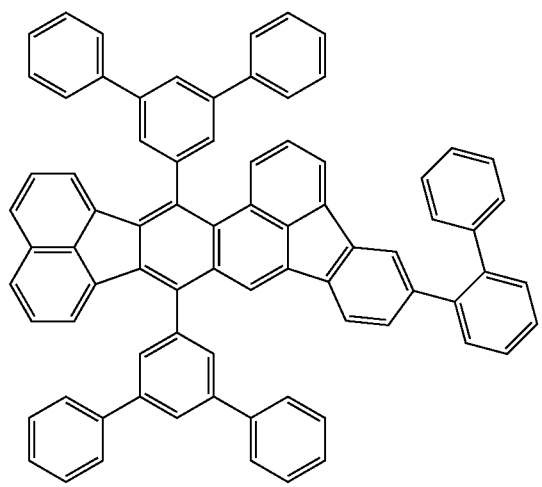 [SMILES: c1ccc(-c2cc(-c3ccccc3)cc(-c3c4cc5c6ccc(-c7ccccc7-c7ccccc7)cc6c6cccc(c4c(-c4cc(-c7ccccc7)cc(-c7ccccc7)c4)c4c7cccc8cccc(c34)c87)c65)c2)cc1]
Synthesis example 23
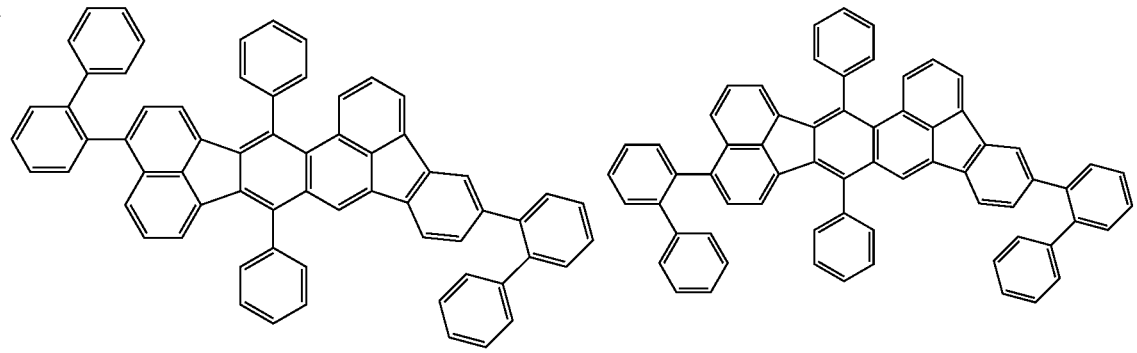
Synthesis example 24
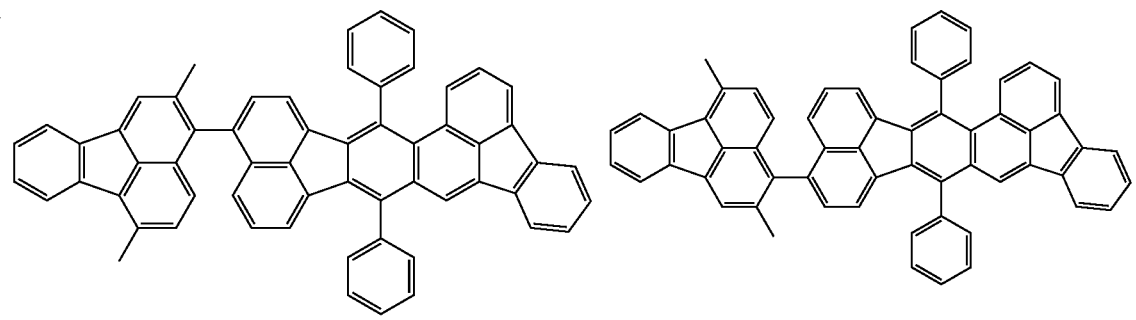
Synthesis example 25
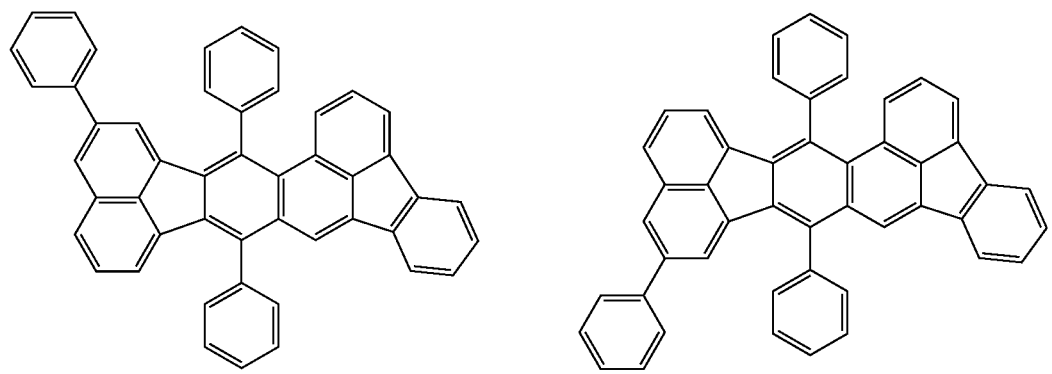

TABLE 2-continued
Synthesis example 26
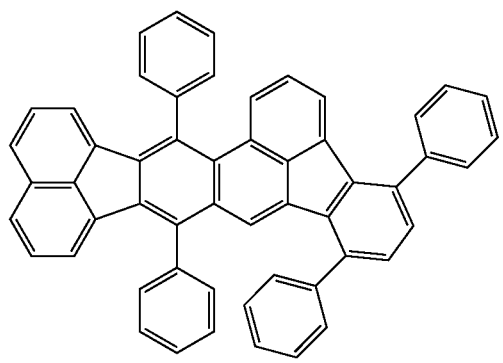 [SMILES: c1ccc(-c2c3cc4c5c(-c6ccccc6)ccc(-c6ccccc6)c5c5cccc(c3c(-c3ccccc3)c3c6cccc7cccc(c23)c76)c54)cc1]
Synthesis example 27
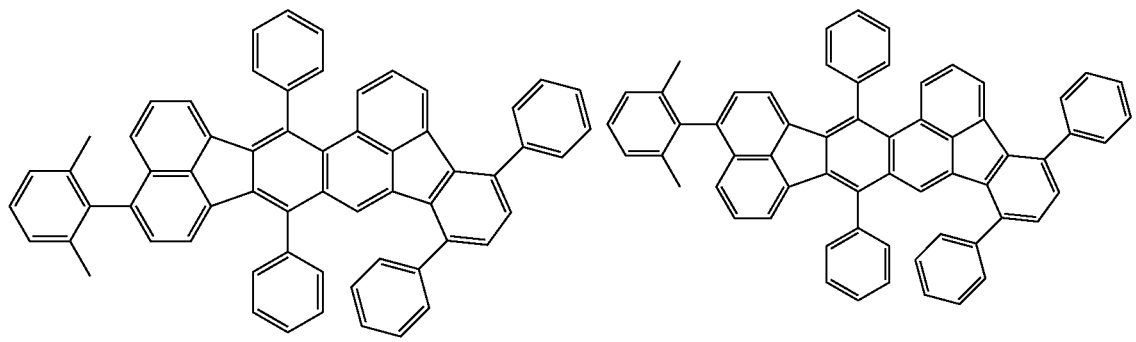
Synthesis example 28
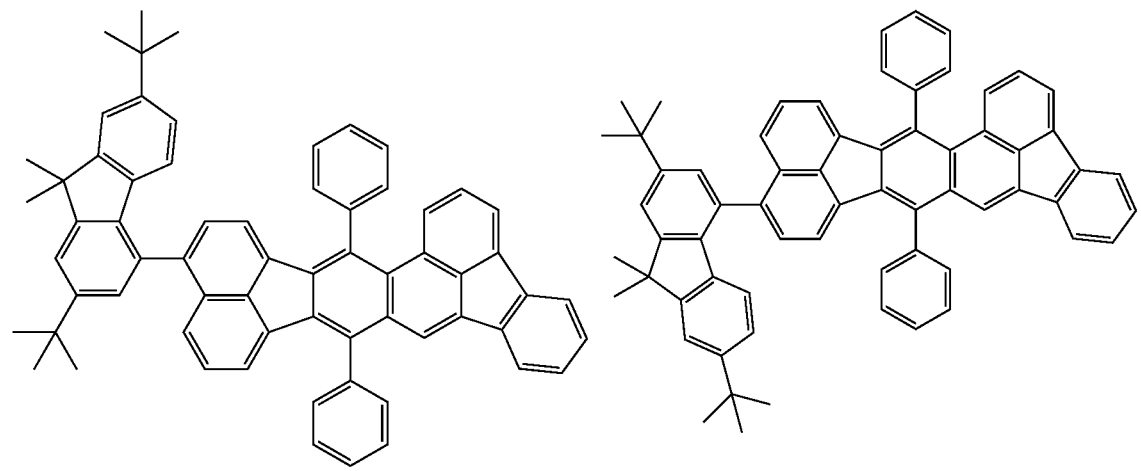
Synthesis example 29
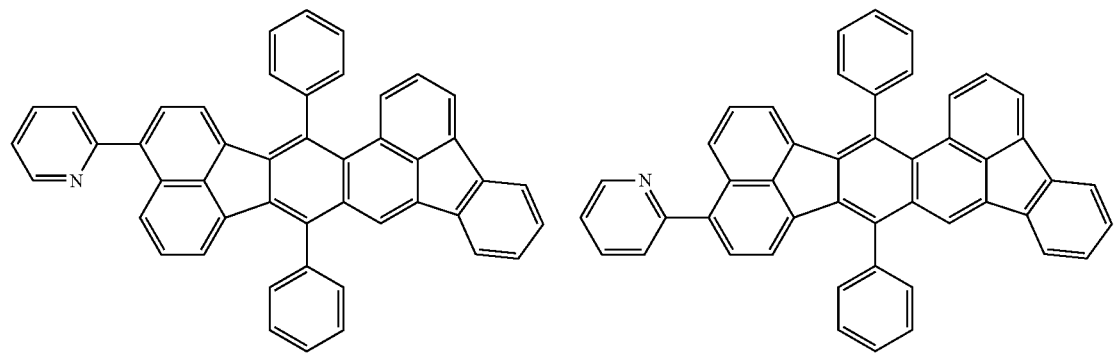

TABLE 2-continued

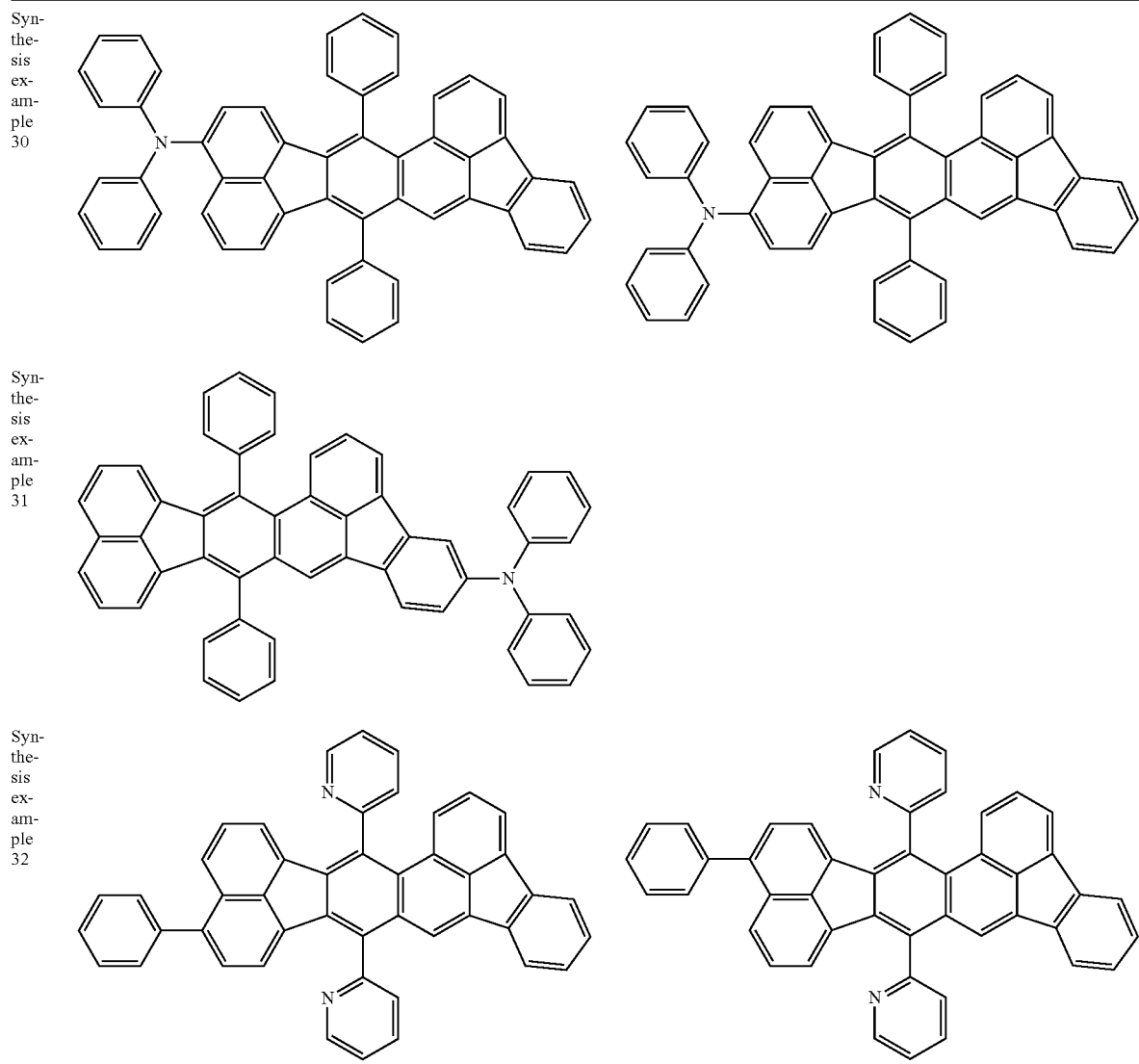

Next, an organic light-emitting device according to the present invention will be described. The organic light-emitting device according to the present invention includes at least a pair of electrodes, i.e., an anode and a cathode, and an organic compound layer interposed between the electrodes. This organic compound layer contains the organic compound represented by general formula (1) above. Organic light-emitting devices are devices in which a luminescent material, which is an organic compound, disposed between a pair of electrodes emits light. When one layer constituting the organic compound layer is a light-emitting layer, the light-emitting layer may be composed of the organic compound according to the present invention alone or may be partly composed of the organic compound according to the present invention. The phrase "light-emitting layer may be partly composed of the organic compound according to the present invention" means that the organic compound according to the present invention may be a main component of the light-emitting layer or an auxiliary component thereof. Herein, among all compounds constituting the light-emitting layer, the main component refers to a compound contained in a large amount in terms of weight or the number of moles, for example, and the auxiliary component refers to a compound contained in a small amount. A material used as the main component can also be referred to as "host material". A material used as the auxiliary component can also be referred to as "dopant (guest) material", "luminescence assist material" or "charge injection material".

When the organic compound according to the present invention is used as the guest material, the concentration of the guest material to the host material is preferably 0.01% by weight or more and 20% by weight or less, and more preferably, 0.5% by weight or more and 10% by weight or less. The wavelength of the light emitted from the light-emitting layer can be made longer than the wavelength of the solution by 5 nm or more and 20 nm or less by varying the concentration of the guest material in any one of these two ranges.

When the light-emitting layer is composed of a host material and guest material having a carrier transport property, a main process that leads to light emission includes the following steps.
1. Transportation of electrons and holes inside the light-emitting layer.

2. Generation of excitons of the host material.
3. Transmission of excitation energy among molecules of the host material.
4. Transfer of the excitation energy from the host material to the guest material.

A desired energy transfer and light emission in each of the steps occur in competition with various deactivation steps.

Naturally, in order to increase the luminous efficiency of the organic light-emitting device, the emission quantum yield of a luminescence center material (e.g., guest material) itself must be high. However, how the energy transfer between the molecules of the host material or between the molecules of the host material and the guest material is efficiently performed is also an important factor. The cause of luminescence degradation due to electrical conduction has not yet become clear. However, it is believed that such degradation relates to at least the luminescence center material itself or the environmental changes that are brought to the luminescence center material by the nearby molecules.

Under these circumstances, the inventors of the present invention conducted various investigations and found that when a compound represented by general formula (1) of the present invention described above is used as the host material or the guest material of a light-emitting layer, in particular, as the guest material thereof, the device outputs light with a high efficiency and high luminance and has markedly high durability.

Next, an organic light-emitting device of the present invention will be described in detail. The organic light-emitting device of the present invention includes at least a pair of electrodes, i.e., an anode and a cathode, and an organic compound layer interposed between the electrodes. In the organic light-emitting device, the organic compound layer contains at least one organic compound represented by general formula (1).

At least one compound layer other than the organic compound layer may be provided between the pair of electrodes. Two or more compound layers including the organic compound layer may be provided between the pair of electrodes. In such a case, the device having such a structure is referred to as "multilayer organic light-emitting device".

A first example to a fifth example of multilayer organic light-emitting devices will be described below.

The first example of the multilayer organic light-emitting device has a structure in which an anode, a light-emitting layer, and a cathode are sequentially provided on a substrate. The organic light-emitting device of this example is useful when a material having a hole transport property, an electron transport property, and a light-emitting property by itself is used in the light-emitting layer, or when compounds having respective properties are mixed and used in the light-emitting layer.

The second example of the multilayer organic light-emitting device has a structure in which an anode, a hole-transporting layer, an electron-transporting layer, and a cathode are sequentially provided on a substrate. The organic light-emitting device of this example is useful when a material having a hole transport property and a material having an electron transport property are used in the corresponding layers or when a material having both these properties is used in both the hole-transporting layer and the electron-transporting layer, and a luminescent substance is used in combination with a simple hole transport substance or electron transport substance that has no light-emitting property. In such a case, the light-emitting layer is either the hole-transporting layer or the electron-transporting layer.

The third example of the multilayer organic light-emitting device has a structure in which an anode, a hole-transporting layer, a light-emitting layer, an electron-transporting layer, and a cathode are sequentially provided on a substrate. This is a device in which functions of carrier transportation and light emission are separated from each other. A compound having a hole transport property, a compound having an electron transport property, and a compound having a light-emitting property may be adequately used in combination. Accordingly, the flexibility of material selection is significantly increased, and various compounds having different emission wavelengths can be used. Consequently, the hue of light emission can be diversified. Furthermore, carriers or excitons are effectively confined in the center light-emitting layer to improve the luminous efficiency.

The fourth example of the multilayer organic light-emitting device has a structure in which an anode, a hole injection layer, a hole-transporting layer, a light-emitting layer, an electron-transporting layer, and a cathode are sequentially provided on a substrate. The organic light-emitting device of this example is advantageous in that the adhesiveness between the anode and the hole-transporting layer is improved and a hole injection property is improved. Accordingly, this structure is effective for reducing the voltage.

The fifth example of the multilayer organic light-emitting device has a structure in which an anode, a hole injection layer, a hole-transporting layer, a light-emitting layer, a hole/exciton-blocking layer, an electron-transporting layer, and a cathode are sequentially provided on a substrate. In this structure, a layer (hole/exciton-blocking layer) that blocks holes or excitons from passing through the cathode side is interposed between the light-emitting layer and the electron-transporting layer. The luminous efficiency can be effectively improved by using a compound having a significantly high ionization potential in the hole/exciton-blocking layer.

In the present invention, a light emission region containing the compound represented by general formula (1) refers to a region of the light-emitting layer described above. However, the first to fifth examples of the multilayer organic light-emitting devices are merely the basic device structures, and the structure of an organic light-emitting device including the organic compound according to the present invention is not limited to the above examples. The organic light-emitting device may have various other layer structures. For example, an insulating layer may be provided between an electrode and an organic layer. An adhesive layer or an interference layer may be provided. Alternatively, the electron-transporting layer or the hole-transporting layer may be composed of two layers having different ionization potentials.

The compound represented by general formula (1) used in the present invention can be used in any one of the first example to the fifth example described above. In the organic light-emitting device according to the present invention, at least one organic compound represented by general formula (1) used in the present invention is contained in a layer containing an organic compound. In particular, the organic compound represented by general formula (1) may be used as a guest material in the light-emitting layer.

The organic compound according to the present invention may be used as a host material in the light-emitting layer.

The organic compound according to the present invention may be used in a layer other than the light-emitting layer, namely, any one of a hole injection layer, a hole-transporting layer, a hole/exciton-blocking layer, an electron-transporting layer, and an electron injection layer.

In addition to the organic compound of the present invention, existing low-molecular weight or high-molecular weight hole-transporting compounds, luminescent compounds, electron-transporting compounds, and the like may be used in combination as required.

Examples of such compounds will be described below. Hole injection/transport materials may have a high hole mobility so that holes can be easily injected from an anode and the injected holes can be transported to the light-emitting layer. Examples of the low-molecular weight and high-molecular weight materials having hole injection/transport properties include, but are not limited to, triarylamine derivatives, phenylenediamine derivatives, stilbene derivatives, phthalocyanine derivatives, porphyrin derivatives, polyvinylcarbazole, polythiophene, and other electrically conductive polymers.

Examples of host materials mainly include, but are not limited to, not only the compounds shown in Table 3 and derivatives of the compounds shown in Table 3, but also fused-ring compounds (such as fluorene derivatives, naphthalene derivatives, anthracene derivatives, pyrene derivatives, carbazole derivatives, quinoxaline derivatives, and quinoline derivatives), organoaluminum complexes such as tris(8-quinolinolato)aluminum, organozinc complexes, triphenylamine derivatives, and polymer derivatives such as polyfluorene derivatives and polyphenylene derivatives.

TABLE 3

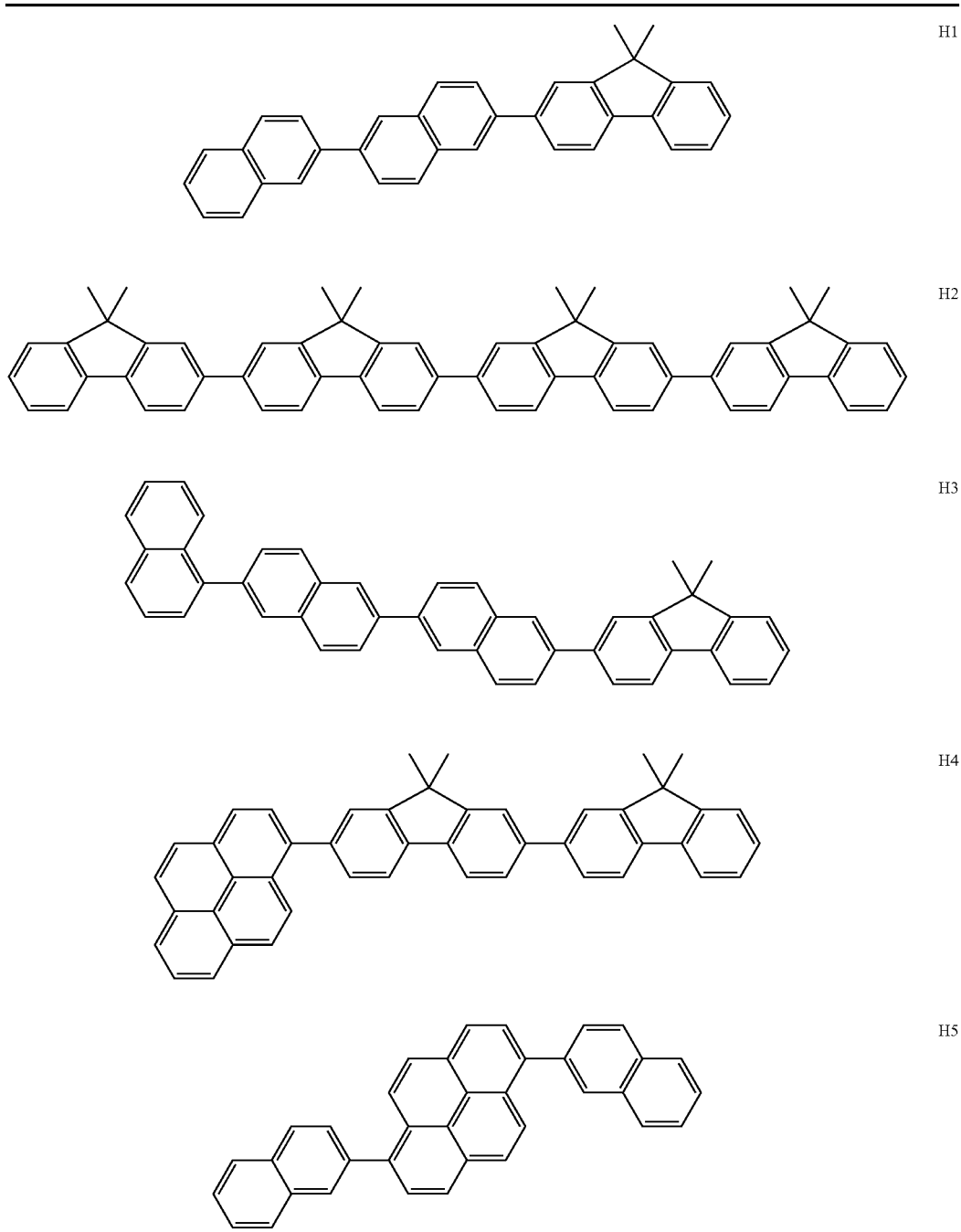

TABLE 3-continued
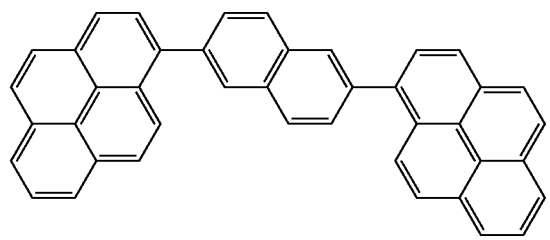 [SMILES: c1cc2ccc3ccc(-c4ccc5cc(-c6ccc7ccc8cccc9ccc6c7c89)ccc5c4)c4ccc(c1)c2c34]
H6
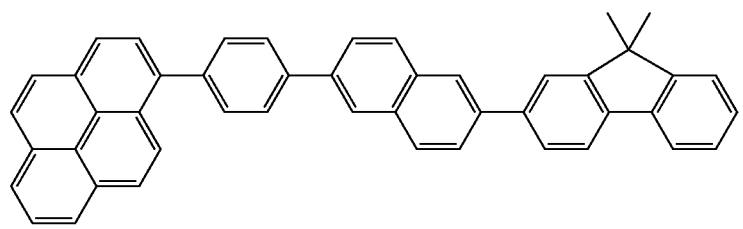 [SMILES: CC1(C)c2ccccc2-c2ccc(-c3ccc4cc(-c5ccc(-c6ccc7ccc8cccc9ccc6c7c89)cc5)ccc4c3)cc21]
H7
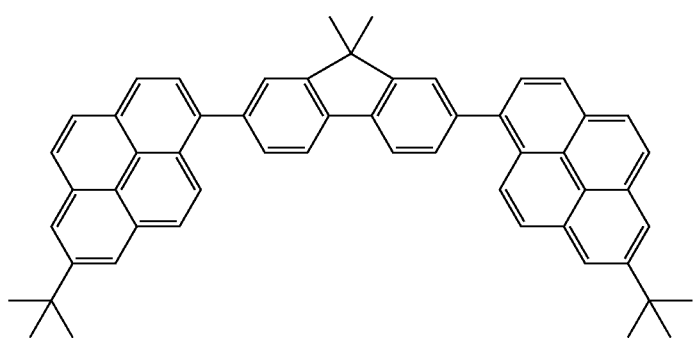 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34]
H8
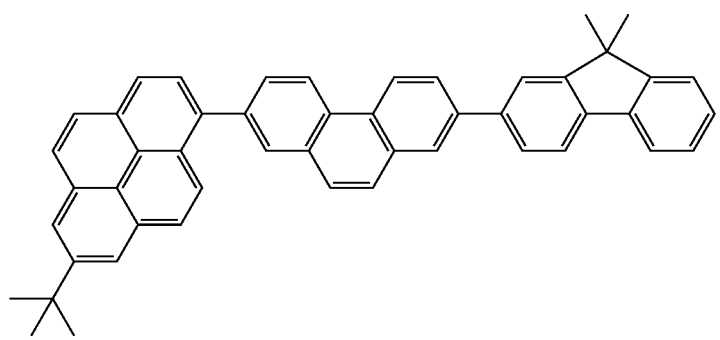 [SMILES: CC(C)(C)c1cc2ccc3ccc(-c4ccc5c(ccc6cc(-c7ccc8c(c7)C(C)(C)c7ccccc7-8)ccc65)c4)c4ccc(c1)c2c34]
H9
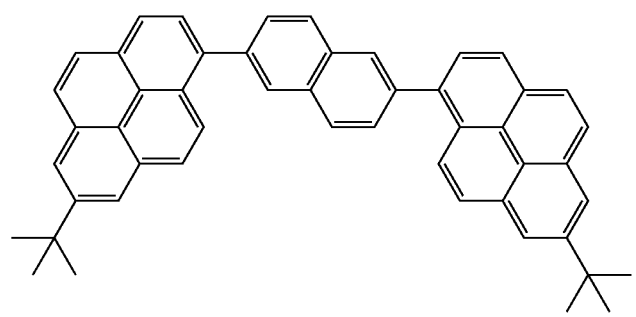 [SMILES: CC(C)(C)c1cc2ccc3ccc(-c4ccc5cc(-c6ccc7ccc8cc(C(C)(C)C)cc9ccc6c7c89)ccc5c4)c4ccc(c1)c2c34]
H10

TABLE 3-continued
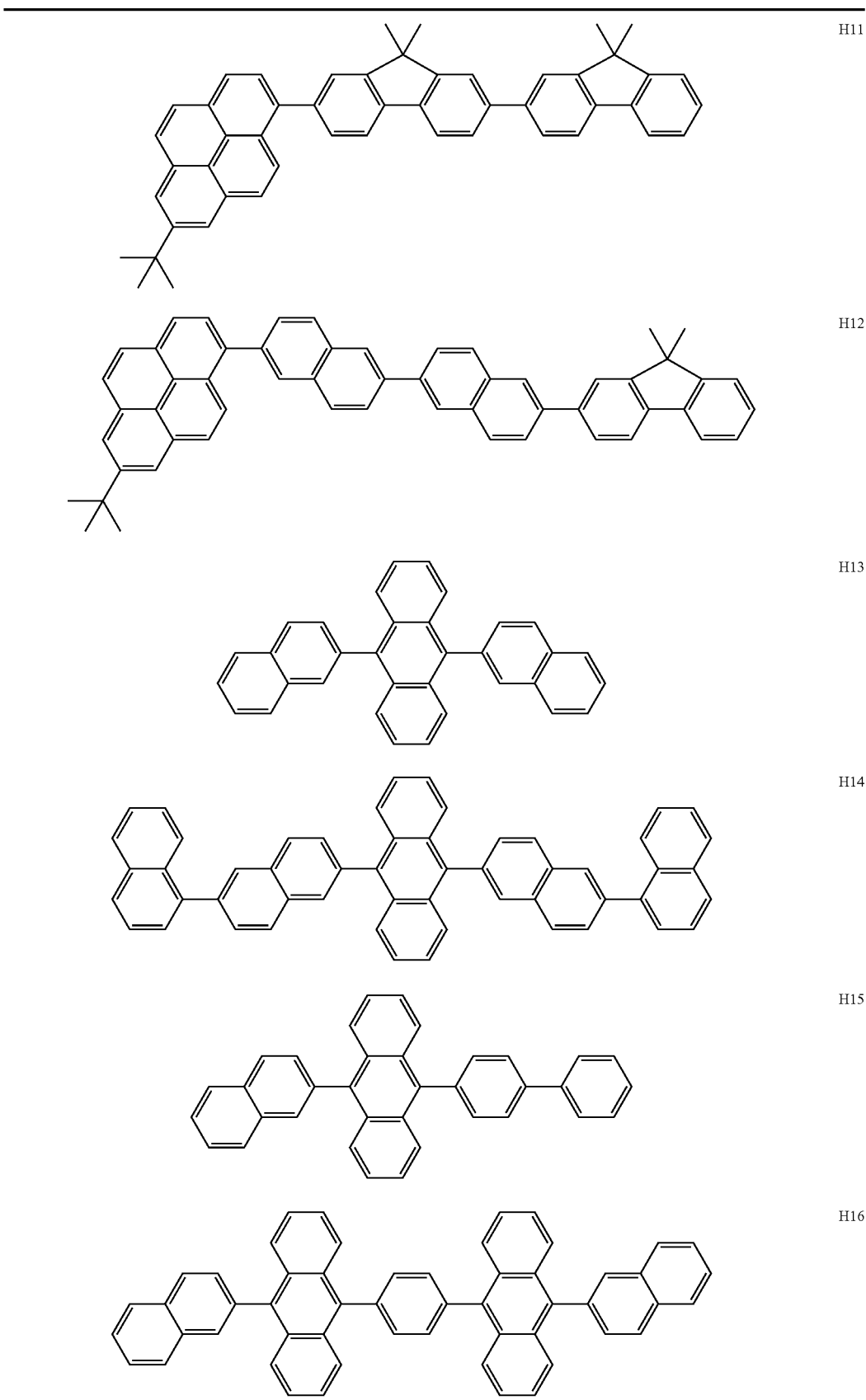
H11
H12
H13
H14
H15
H16

TABLE 3-continued
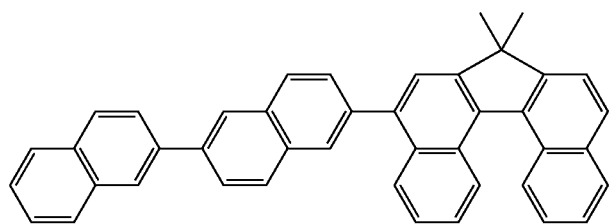 [SMILES: CC1(C)c2ccc3ccccc3c2-c2c1cc(-c1ccc3cc(-c4ccc5ccccc5c4)ccc3c1)c1ccccc21]
H17
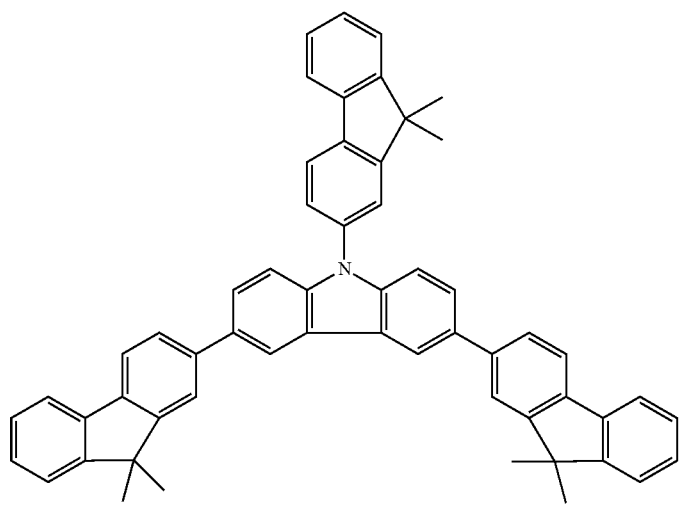 [SMILES: CC1(C)c2ccccc2-c2ccc(-c3ccc4c(c3)c3cc(-c5ccc6c(c5)C(C)(C)c5ccccc5-6)ccc3n4-c3ccc4c(c3)C(C)(C)c3ccccc3-4)cc21]
H18
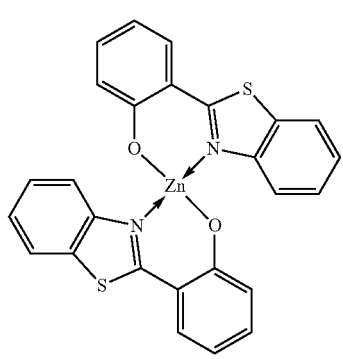
H19
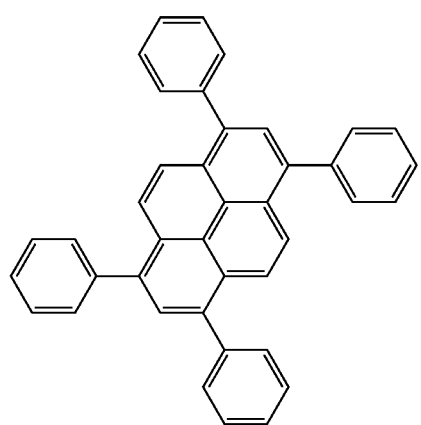 [SMILES: c1ccc(-c2cc(-c3ccccc3)c3ccc4c(-c5ccccc5)cc(-c5ccccc5)c5ccc2c3c54)cc1]
H20

TABLE 3-continued
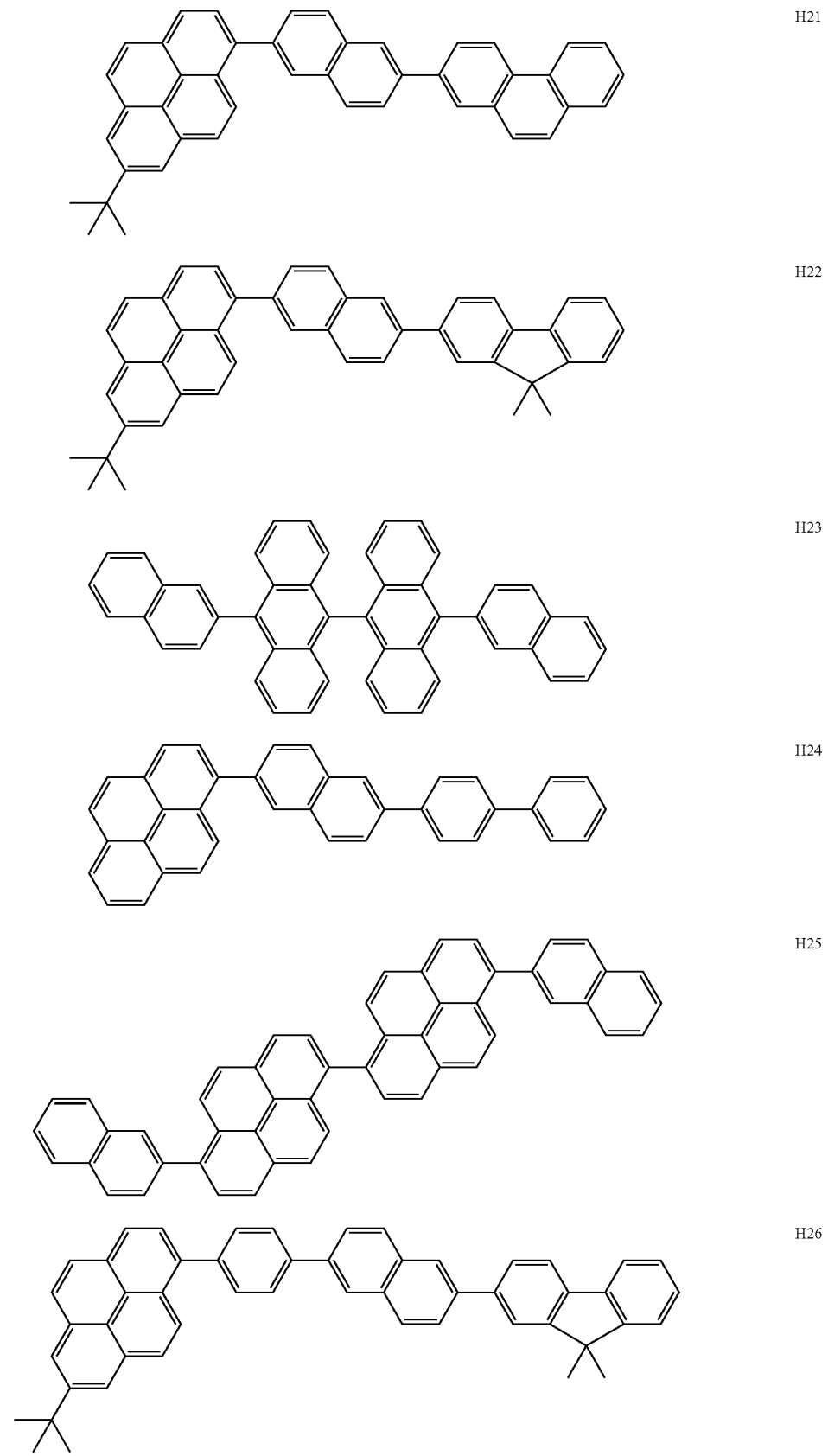
H21
H22
H23
H24
H25
H26

TABLE 3-continued
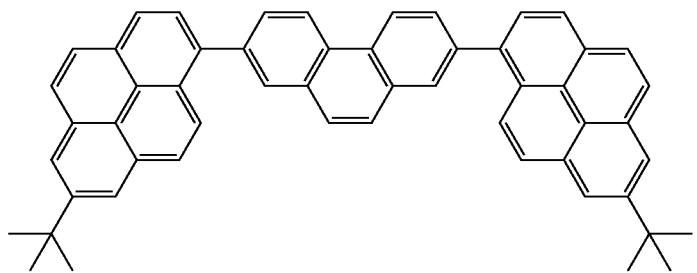 [SMILES: CC(C)(C)c1cc2ccc3ccc(-c4ccc5c(ccc6cc(-c7ccc8ccc9cc(C(C)(C)C)cc%10ccc7c8c9%10)ccc65)c4)c4ccc(c1)c2c34]
H27
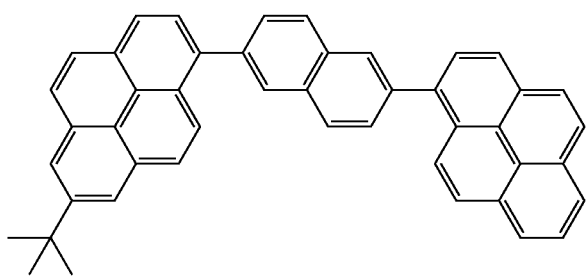 [SMILES: CC(C)(C)c1cc2ccc3ccc(-c4ccc5cc(-c6ccc7ccc8cccc9ccc6c7c89)ccc5c4)c4ccc(c1)c2c34]
H28
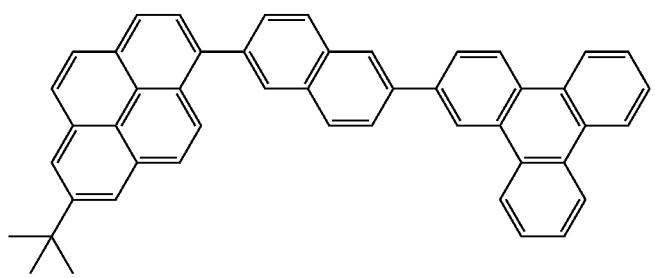 [SMILES: CC(C)(C)c1cc2ccc3ccc(-c4ccc5cc(-c6ccc7c8ccccc8c8ccccc8c7c6)ccc5c4)c4ccc(c1)c2c34]
H29
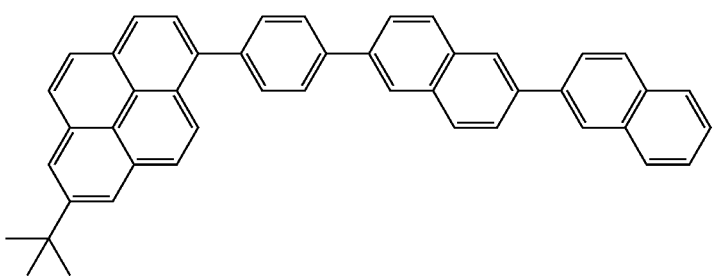 [SMILES: CC(C)(C)c1cc2ccc3ccc(-c4ccc(-c5ccc6cc(-c7ccc8ccccc8c7)ccc6c5)cc4)c4ccc(c1)c2c34]
H30
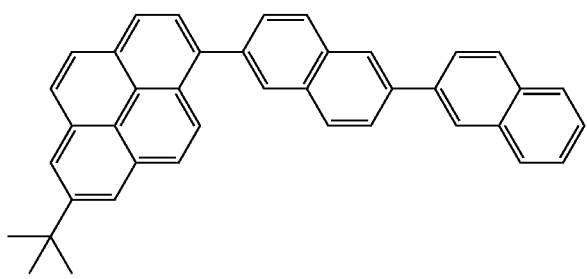 [SMILES: CC(C)(C)c1cc2ccc3ccc(-c4ccc5cc(-c6ccc7ccccc7c6)ccc5c4)c4ccc(c1)c2c34]
H31

TABLE 3-continued

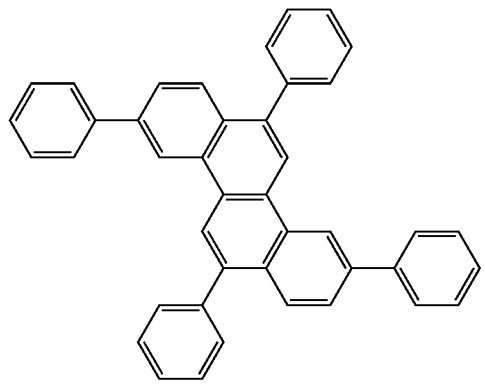 [SMILES: c1ccc(-c2ccc3c(-c4ccccc4)cc4c5cc(-c6ccccc6)ccc5c(-c5ccccc5)cc4c3c2)cc1]

H32

The electron injection/transport material can be adequately selected from materials to which electrons are easily injected from a cathode and which can transport the injected electrons to the light-emitting layer. The material is selected in consideration of, for example, the balance with the hole mobility of the hole injection/transport material. Examples of the materials having electron injection/transport properties include, but are not limited to, oxadiazole derivatives, oxazole derivatives, pyrazine derivatives, triazole derivatives, triazine derivatives, quinoline derivatives, quinoxaline derivatives, phenanthroline derivatives, and organoaluminum complexes.

The material for the anode may be a material having a work function as high as possible. Examples thereof include metal elements such as gold, platinum, silver, copper, nickel, palladium, cobalt, selenium, vanadium, and tungsten; alloys thereof; and metal oxides such as tin oxide, zinc oxide, indium oxide, indium tin oxide (ITO), and indium zinc oxide. Electrically conductive polymers such as polyaniline, polypyrrole, and polythiophene can also be used. These electrode substances may be used alone or in combinations of two or more substances. The anode may have a single-layer structure or a multilayer structure.

On the other hand, the material for the cathode may be a material having a low work function. Examples thereof include metal elements such as alkali metals, e.g., lithium; alkaline earth metals, e.g., calcium; aluminum; titanium; manganese; silver; lead; and chromium. Alloys combining these metal elements can also be used. Examples thereof include magnesium-silver, aluminum-lithium, and aluminum-magnesium. Metal oxides such as indium tin oxide (ITO) can also be used. These electrode substances may be used as alone or in combinations of two or more substances. The cathode may have a single-layer structure or a multilayer structure.

Examples of the substrate used in the organic light-emitting device of the present invention include, but are not particularly limited to, opaque substrates such as a metal substrate and a ceramic substrate, and transparent substrates such as a glass substrate, a quartz substrate, and a plastic sheet. The luminescent color can be controlled by providing a color filter film, a fluorescent color conversion filter film, a dielectric reflecting film, or the like on the substrate.

A protective layer or a sealing layer may be provided on the prepared device in order to prevent the device contacting oxygen, moisture, and the like. Examples of the protective layer include inorganic material films such as a diamond thin film, metal oxide films, and metal nitride films; polymer films such as fluorocarbon resin films, a polyethylene film, silicone resin films, and a polystyrene resin film; and photocurable resin films. The device may be covered with, for example, glass, a gas-impermeable film, or a metal and packaged with an adequate sealing resin.

In the organic light-emitting device of the present invention, a layer containing the organic compound of the present invention and layers composed of other organic compounds are formed by the methods described below. In general, a thin film is formed by a vacuum evaporation method, an ionized vapor deposition method, a sputtering method, a plasma deposition method, or an existing coating method (for example, spin coating, dipping, a cast method, a Langmuir-Blodgett (LB) technique, or an ink jet method) that involves dissolving a compound in an adequate solvent. Among these, when a layer is formed by a vacuum evaporation method, a solution coating method, or the like, crystallization does not readily occur and thus the resulting layer has good stability with time. When a coating method is used to form a film, an adequate binder resin may be used in combination with the compound.

Examples of the binder resin include, but are not limited to, polyvinylcarbazole resins, polycarbonate resins, polyester resins, ABS resins, acrylic resins, polyimide resins, phenolic resins, epoxy resins, silicone resins, and urea resins. These binder resins may be used alone as a homopolymer or a copolymer or used as a mixture of two or more types of resin. Furthermore, existing additives such as a plasticizer, an antioxidant, or an ultraviolet absorber may be optionally used in combination.

The organic light-emitting device of the present invention can be applied to products that require energy saving and high luminance. Application examples thereof include light sources of display apparatuses, illuminating apparatuses, and printers, and backlights for liquid crystal display apparatuses.

When the organic light-emitting device is applied to a display apparatus, a high-visibility, lightweight, flat panel display that realizes energy saving can be obtained. The display apparatus can be used as an image display apparatus such as a personal computer, a television, or an advertizing medium. Alternatively, the display apparatus may be used in a display unit of an image pickup apparatus such as a digital still camera or a digital video camera. Alternatively, the display apparatus may be used in an operation display unit of an electrophotographic image-forming apparatus, namely, a laser beam printer, a copy machine, or the like.

Alternatively, the organic light-emitting device may be used as a light source that is used when a latent image is exposed on a photosensitive member of an electrophotographic image-forming apparatus, namely, a laser beam printer, a copy machine, or the like. A plurality of organic light-emitting devices that can be independently addressed may be arranged into an array (e.g., lines) and desired exposure may be performed on a photosensitive drum to form a latent image. The use of organic light-emitting devices of the present invention can decrease the space that has been previously required for arranging a light source, polygon mirrors, and various optical lenses. When the organic light-emitting device is applied to illuminating apparatuses and the backlights, the effect of energy saving can be expected. The organic light-emitting device of the present invention can also be used as a surface light source.

As described above, the luminescent color can be controlled by providing a color filter film, a fluorescent color conversion filter film, a dielectric reflecting film, or the like on a substrate supporting the organic light-emitting device of the present invention. A thin-film transistor (TFT) may be formed on the substrate and connected to the organic light-emitting device to control the emission/non-emission. Alternatively, a plurality of organic light-emitting devices may be arranged in a matrix shape, that is, arranged in an in-plane direction and used as an illuminating apparatus.

Next, a display apparatus that uses the organic light-emitting device of the present invention will be described. This display apparatus includes the organic light-emitting device of the present invention and a unit configured to supply electrical signals to the organic light-emitting device of the present invention.

The display apparatus of the present invention will now be described with reference to the accompanying drawings by taking an active matrix system as an example.

Figure 2:
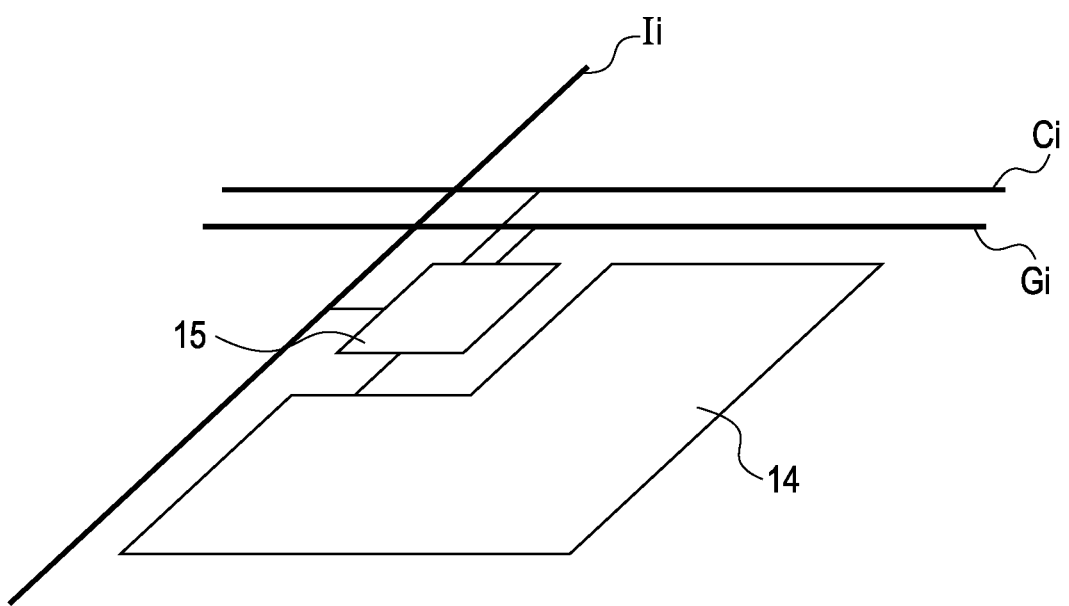
FIG. 2 is a schematic view showing a pixel circuit connected to a pixel and a signal line and current supply line that are connected to the pixel circuit.

FIG. 1 is a schematic view of an example of the structure of a display apparatus according to an embodiment. The display apparatus includes organic light-emitting devices of the present invention and units configured to supply electrical signals to the organic light-emitting devices of the present invention. FIG. 2 is a schematic view showing a pixel circuit connected to a pixel, and a signal line and a current supply line that are connected to the pixel circuit.

The units configured to supply electrical signals to the organic light-emitting devices of the present invention include a scanning signal driver 11, an information signal driver 12, and a current supply source 13 in FIG. 1 and a pixel circuit 15 in FIG. 2.

Referring to a display apparatus 1 shown in FIG. 1, the scanning signal driver 11, the information signal driver 12, and the current supply source 13 are arranged and connected to gate selection lines G, information signal lines I, and current supply lines C, respectively. As shown in FIG. 2, pixel circuits 15 are arranged at intersections between the gate selection lines G and the information signal lines I. One pixel 14 constituted by the organic light-emitting device according to the present invention is provided for each corresponding pixel circuit 15. The pixel 14 is an organic light-emitting device. Accordingly, in the drawing, organic light-emitting devices are illustrated as luminous points. In the drawing, an upper electrode of an organic light-emitting device may be formed as a common upper electrode for other organic light-emitting devices. Alternatively, the upper electrodes of the respective organic light-emitting devices may be separately formed.

The scanning signal driver 11 sequentially selects the gate selection lines G1, G2, G3, . . . and Gn. In synchronization with this, image signals are applied to the pixel circuits 15 from the information signal driver 12 through one of the information signal lines I1, I2, I3, . . . and In.

Figure 3:
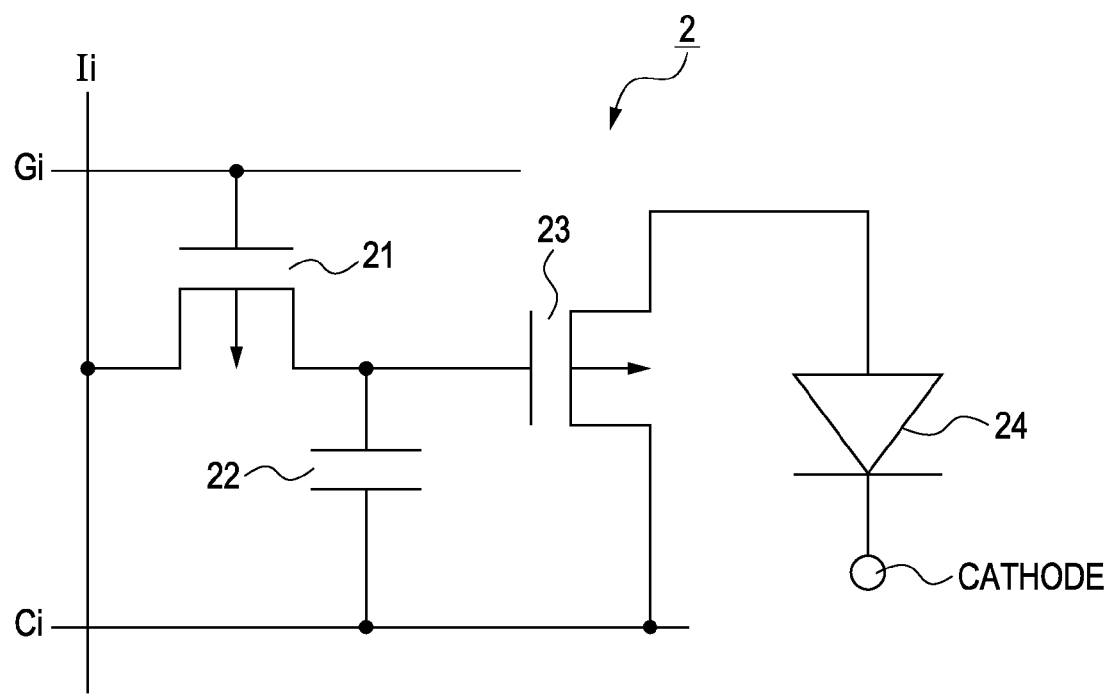
FIG. 3 is a diagram showing the pixel circuit.

Next, operation of the pixels will be described. FIG. 3 is a circuit diagram showing a circuit constituting one pixel arranged in the display apparatus shown in FIG. 1. In FIG. 3, a second thin-film transistor (TFT) 23 controls the current for causing an organic light-emitting device 24 to emit light. In a pixel circuit 2 shown in FIG. 3, when a selection signal is applied to the gate selection line G1, a first thin-film transistor 21 turns to the ON state, and an image signal Ii is supplied to a capacitor ($C_{add}$) 22 to determine a gate voltage of the second thin-film transistor 23. A current is supplied from the current supply line Ci to the organic light-emitting device 24 in accordance with the gate voltage of the second thin-film transistor 23. The gate potential of the second thin-film transistor 23 is retained in the capacitor ($C_{add}$) 22 until the first thin-film transistor 21 is scanned and selected next time. Accordingly, the current continues to be supplied to the organic light-emitting device 24 until the next time scanning is performed. Thus, it is possible to constantly cause the organic light-emitting device 24 to emit light during one frame period.

Although not shown in the drawings, the organic light-emitting device according to the present invention can also be used in a voltage-write display apparatus in which a thin-film transistor controls the voltage between the electrodes of the organic light-emitting device 24.

Figure 4:
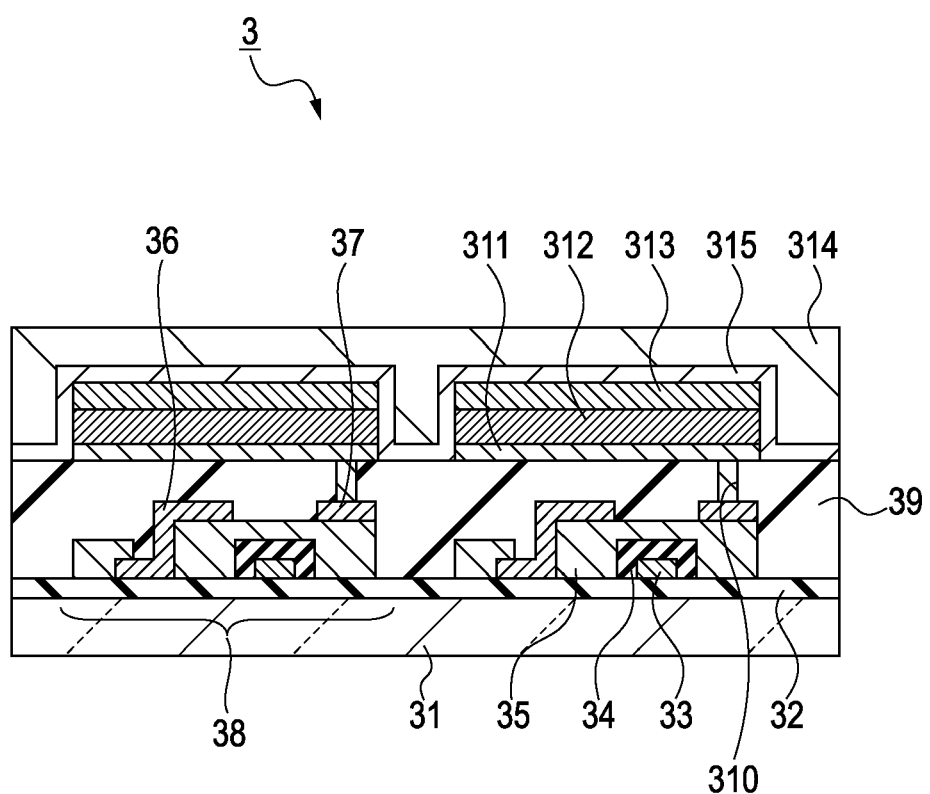
FIG. 4 is a schematic cross-sectional view showing organic light-emitting devices and TFTs disposed under the organic light-emitting devices.

FIG. 4 is a schematic view showing an example of the cross-sectional structure of a TFT substrate used in the display apparatus shown in FIG. 1. The structure will now be described in detail by taking a process of producing the TFT substrate as an example. In producing a display apparatus 3 shown in FIG. 4, first, a moisture-proof film 32 for protecting components (TFTs and an organic layer) to be formed thereon is formed on a substrate 31 composed of glass or the like by coating. Silicon oxide, a composite material of silicon oxide and silicon nitride, or the like is used as the material for the moisture-proof film 32. Next, a gate electrode 33 is formed by depositing a metal such as chromium (Cr) on the moisture-proof film 32 by sputtering, and then patterning the chromium film to have a predetermined circuit shape.

Subsequently, a gate insulating film 34 is formed by depositing silicon oxide or the like by a plasma chemical vapor deposition (CVD) method, a catalytic chemical vapor deposition (cat-CVD) method, or the like, and then patterning the silicon oxide film. Next, a semiconductor layer 35 is formed by depositing a silicon film by the plasma CVD method or the like (and annealing the silicon film at a temperature of 290° C. or higher if necessary), and patterning the silicon film in accordance with a circuit shape.

Furthermore, a drain electrode 36 and a source electrode 37 are formed on the semiconductor layer 35 to form a TFT device 38. Thus, a circuit as shown in FIG. 3 is formed. Next, an insulating film 39 is formed on the TFT devices 38. Subsequently, a contact hole (through-hole) 310 is formed so that a metal anode 311 for an organic light-emitting device is connected to the source electrode 37.

A multilayered or single-layered organic layer 312 and a cathode 313 are sequentially stacked on the anode 311. As a result, the display apparatus 3 is obtained. In order to prevent degradation of the organic light-emitting devices, a first protective layer 314 and a second protective layer 315 may also be provided. By driving the display apparatus including the organic light-emitting devices of the present invention, high-quality images can be stably displayed for a long period of time. Note that the switching device of the above display apparatus is not particularly limited. The display apparatus can be easily applied to a single-crystal silicon substrate, an MIM device, an amorphous-Si (a-Si) device, or the like.

An organic light-emitting display panel can be obtained by sequentially stacking a multilayer or single-layer organic light-emitting layer and a cathode layer on the ITO electrode. By driving the display panel that uses the organic compound of the present invention, high-quality images can be stably displayed for a long period of time.

As for a direction in which the light is output from the device, either one of the bottom emission configuration (configuration in which light is output from the substrate side) or the top emission configuration (configuration in which light is output from the side opposite the substrate) may be used.

EXAMPLES

The present invention will be more specifically described by way of Examples, but the present invention is not limited thereto.

Example 1

Synthesis of Exemplary Compounds A20 and A21

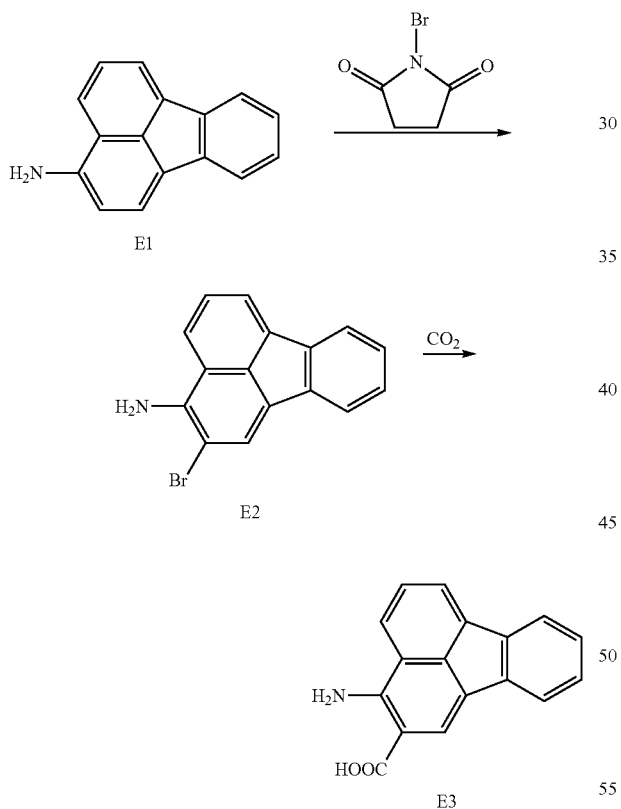

First, 10.5 g (48 mmol) of fluoranthene-3-amine (E1) was mixed in 300 mL of dimethylformamide at 0° C., and 8.2 g (48 mmol) of N-bromosuccinimide was added to the mixture. The temperature of the reaction mixture was returned to the room temperature, and the mixture was stirred for eight hours. The mixture was poured into water, and the precipitate was filtered and then recrystallized with ethanol. After the crystals were filtered, the crystals were washed with heptane, and then dried. As a result, 29 g of a brown solid E2 was obtained (yield: 60%). Subsequently, 10 g (34 mmol) of E2 was charged in a 500-mL round-bottom flask, and the atmosphere in the flask was replaced with argon. Next, 150 mL of methoxycyclopentane was added thereto under the argon atmosphere, and the solution was cooled to −75° C. Next, 64 mL of a 1.6M n-butyllithium solution was added dropwise to the solution. After the dropwise addition, the temperature of the solution was returned to room temperature, and the solution was stirred for one hour. Subsequently, the solution was again cooled to −75° C., and 15 g of finely crushed dry ice was added thereto. The temperature of the solution was gradually returned to room temperature. After the temperature was returned to room temperature, the solution was stirred for eight hours. Subsequently, 1M hydrochloric acid was added to terminate the reaction. Next, extraction was conducted with ethyl acetate, and the organic layer was concentrated to obtain a brownish-red liquid. The liquid was purified by column chromatography (ethyl acetate/heptane=1:3), and recrystallization was then conducted with chloroform/methanol. As a result, 2.5 g (yield: 28%) of E3 was obtained in the form of yellow green crystals.

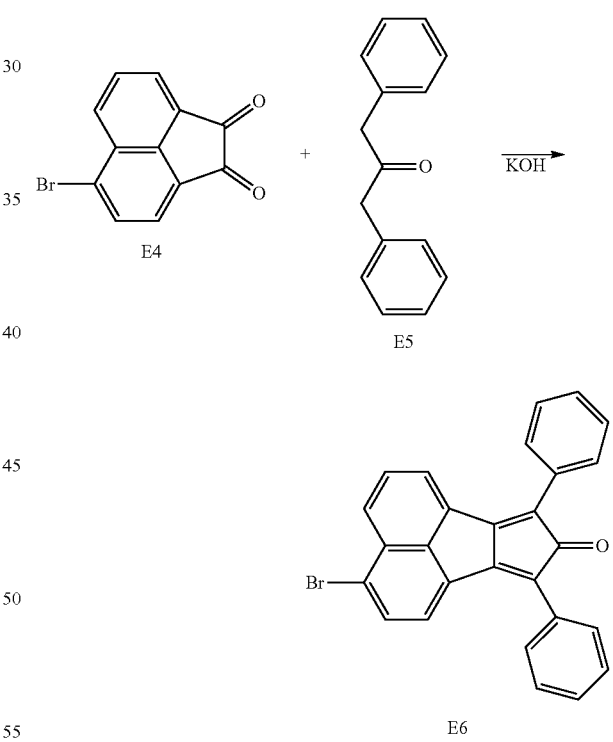

Into 200 mL of ethanol, 13.1 g (50 mmol) of E4 and 10.5 g (50 mmol) of E5 were charged, and the solution was heated to 60° C. Subsequently, 20 mL of a 5M aqueous potassium hydroxide solution was added dropwise to the solution. After the dropwise addition, the reaction mixture was heated to 80° C., stirred for two hours, and then cooled. Subsequently, the precipitate was filtered, washed with water and ethanol, and then dried by heating at 80° C. under a reduced pressure. As a result, 20 g (yield: 92%) of dark green solid E6 was obtained.

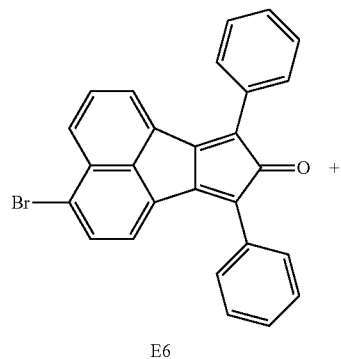

E6

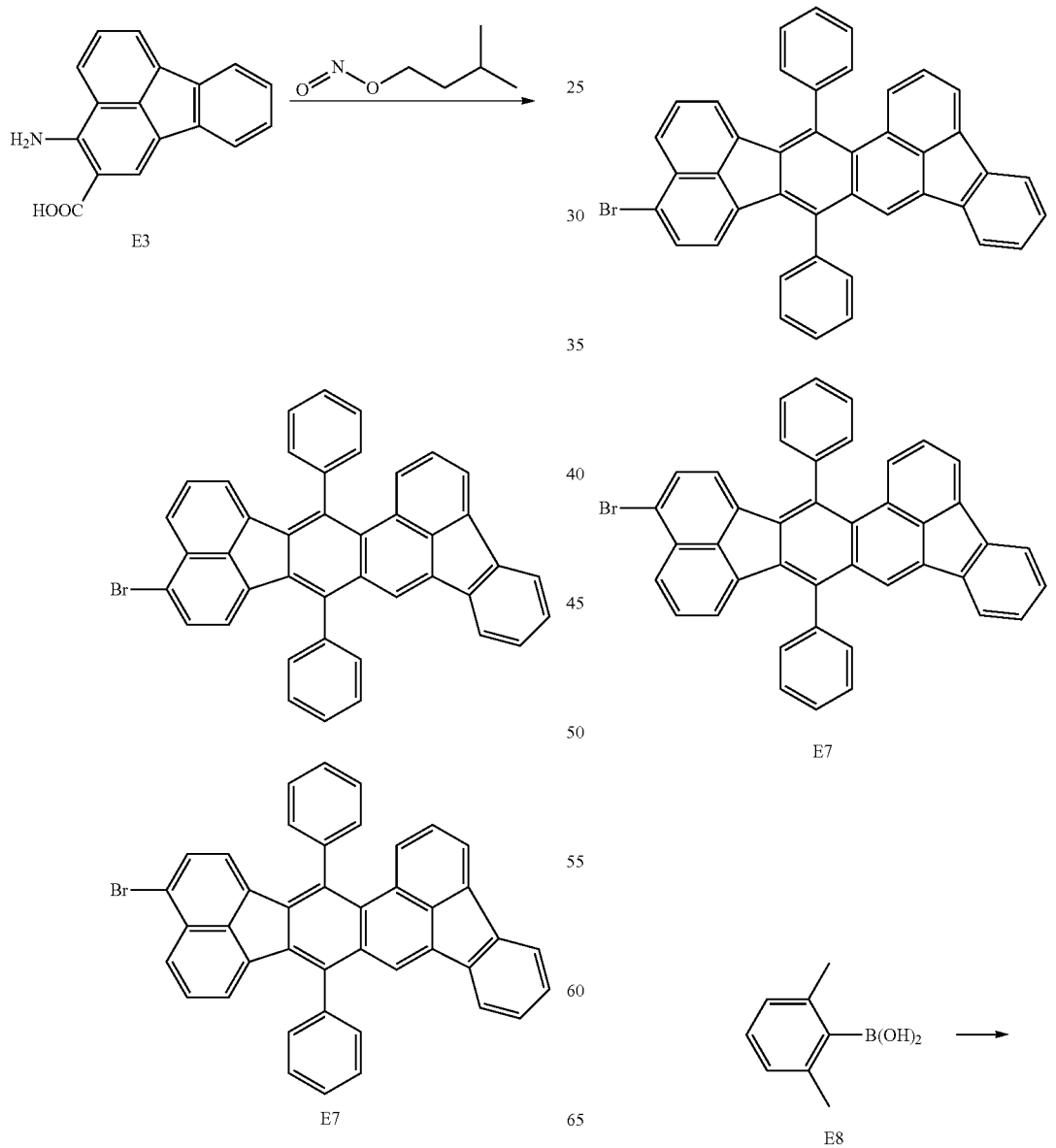

Next, 2.3 g (5 mmol) of E6 and 1.57 g (6 mmol) of E3 were charged in 50 mL of toluene, and the solution was heated to 80° C. Subsequently, 0.82 g (7 mmol) of isoamyl nitrite was gradually added dropwise to the solution, and the reaction mixture was then stirred at 110° C. for three hours. After cooling, the mixture was washed twice with 100 mL of water each time. The organic layer was washed with saturated saline and dried over magnesium sulfate. The solution was filtered, and the filtrate was then concentrated to obtain a brownish-red liquid. The liquid was purified by column chromatography (toluene/heptane=1:1), and recrystallization was conducted with chloroform/methanol. As a result, 2.58 g (yield: 85%) of E7, which was a mixture of isomers, was obtained in the form of yellow crystals.

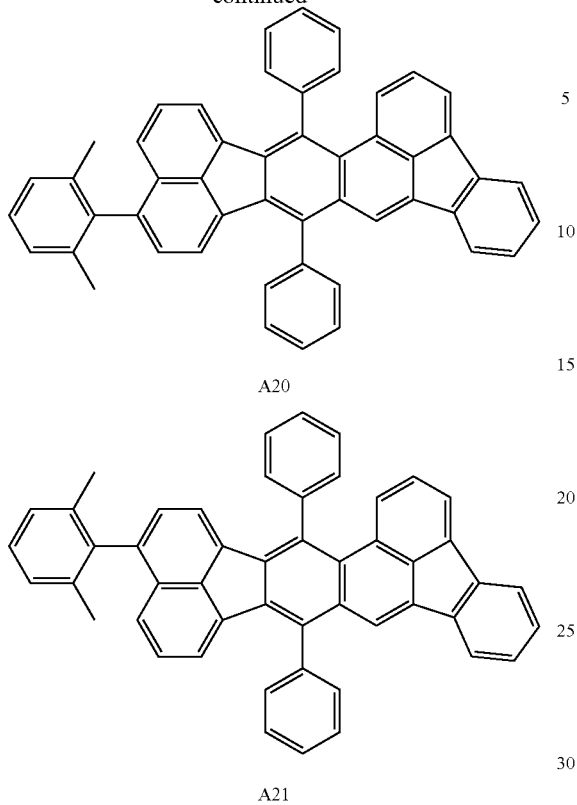

A20

A21

Into a 100-mL round-bottom flask, 1.21 g (2 mmol) of E7, 330 mg (2.2 mmol) of 2,6-dimethylphenylboronic acid (E8), 0.05 g of Pd(PPh$_3$)$_4$, 20 mL of toluene, 10 mL of ethanol, and 20 mL of a 2M aqueous sodium carbonate solution were charged, and the mixture was stirred under nitrogen at 80° C. for eight hours. After the completion of the reaction, the resulting crystals were separated by filtration, and dispersed and washed in water, ethanol, and heptane. The crystals were dissolved in toluene under heating, and the solution was subjected to hot filtration. Recrystallization was conducted with toluene/ethanol. The crystals were dried in a vacuum at 120° C., and purified by sublimation. As a result, 950 mg (yield: 75%) of a mixture of Exemplary Compounds A20 and A21 was obtained in the form of pale yellow crystals. A part of the mixture was further fractionated into A20 and A21 by recrystallization.

The structure of the compound of this 1:1 mixture was confirmed by NMR spectroscopy.

$^1$H NMR (CDCl$_3$, 500 MHz) σ (ppm): 8.20 (s, 2H), 7.88-7.87 (m, 4H), 7.83-7.65 (m, 22H), 7.39-7.05 (m, 20H), 6.60 (d, 1H, J=7.25 Hz), 6.52 (d, 1H, J=3.6 Hz), 6.37 (d, 1H, J=7.25 Hz), 6.28 (t, 1H, J=5.10 Hz), 1.89 (s, 13H).

The emission spectra of toluene solutions of Exemplary Compounds A20 and A21 with a concentration of 1×10$^{-5}$ mol/L were measured using a fluorescence spectrophotometer F-4500 manufactured by Hitachi, Ltd. According to the results of photoluminescence measured at an excitation wavelength of 350 nm, each of the spectra had the maximum intensity at 447 nm.

Example 2

Synthesis of Exemplary Compounds A65 and A66

The reactions and purifications were conducted as in Example 1 except that organic compound E8 used in Example 1 was changed to E9.

[Chem. 10]

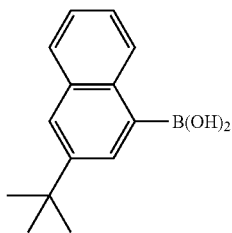

E9

The structure of the compound of a 1:1 mixture was confirmed by NMR spectroscopy.

$^1$H NMR (CDCl$_3$, 500 MHz) σ (ppm): 8.22 (d, 2H, J=6.2 Hz), 7.89-7.65 (m, 30H), 7.53 (d, 2H, J=8.8 Hz), 7.49-7.47 (m, 4H), 7.42-7.30 (m, 12H), 7.20-7.14 (m, 2H), 6.66 (d, 1H, J=7.25 Hz), 6.53 (d, 1H, J=7.25 Hz), 6.43 (d, 1H, J=7.3 Hz), 6.30 (d, 1H, J=7.0 Hz), 1.39 (s, 18H), 1.13 (s, 18H).

The emission spectrum of a toluene solution of the mixture of Exemplary Compounds A65 and A66 with a concentration of 1×10$^{-5}$ mol/L was measured using a fluorescence spectrophotometer F-4500 manufactured by Hitachi, Ltd. According to the result of photoluminescence measured at an excitation wavelength of 350 nm, the spectrum had the maximum intensity at 451 nm.

Example 3

Synthesis of Exemplary Compounds A96 and A97

The reactions and purifications were conducted as in Example 1 except that organic compound E5 used in Example 1 was changed to E10 and organic compound E8 used in Example 1 was changed to E11.

[Chem. 11]

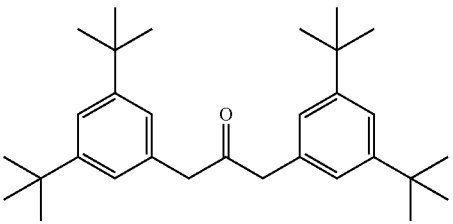

E10

E11

The structure of the compound of a 1:1 mixture was confirmed by NMR spectroscopy.

$^1$H NMR (CDCl$_3$, 500 MHz) σ (ppm): 8.35 (s, 1H), 8.32 (s, 1H), 7.88-7.81 (m, 6H), 7.75 (s, 2H), 7.70 (s, 2H), 7.55 (s, 4H), 7.52-7.51 (m, 4H), 7.39-7.16 (m, 13H), 7.07-7.02 (m, 2H), 6.96 (s, 3H), 6.62 (d, 1H, J=7.2 Hz), 6.52 (d, 1H, J=6.5 Hz), 6.38 (d, 1H, J=7.0 Hz), 6.32 (d, 1H, J=7.0 Hz), 2.36 (s, 6H), 1.87 (s, 12H), 1.44 (t, 36H, J=3.35 Hz), 1.40 (s, 36H).

The emission spectrum of a toluene solution of the mixture of Exemplary Compounds A96 and A97 with a concentration of $1\times10^{-5}$ mol/L was measured using a fluorescence spectrophotometer F-4500 manufactured by Hitachi, Ltd. According to the result of photoluminescence measured at an excitation wavelength of 350 nm, the spectrum had the maximum intensity at 449 nm.

Example 4

Synthesis of Exemplary Compounds A85 and A89

The reactions and purifications were conducted as in Example 1 except that organic compound E8 used in Example 1 was changed to E12.

[Chem. 12]

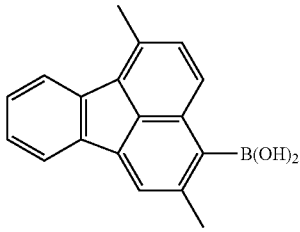

E12

The structure of the compound of a 1:1 mixture was confirmed by NMR spectroscopy.

$^1$H NMR (CDCl$_3$, 500 MHz) σ (ppm): 8.22 (d, 2H, J=6.45 Hz), 7.99-7.97 (m, 4H), 7.92 (s, 2H), 7.88 (d, 4H, J=7.25 Hz), 7.84-7.67 (m, 20H), 7.42-7.24 (m, 24H), 7.18-7.14 (m, 8H), 7.05 (d, 1H, J=7.0 Hz), 6.66 (d, 1H, J=7.15 Hz), 6.52 (d, 1H, J=6.5 Hz), 6.43 (d, 1H, J=7.5 Hz), 6.29 (d, 1H, J=6.6 Hz), 2.83 (s, 6H), 2.24 (s, 6H).

The emission spectrum of a toluene solution of the mixture of Exemplary Compounds A85 and A89 with a concentration of $1\times10^{-5}$ mol/L was measured using a fluorescence spectrophotometer F-4500 manufactured by Hitachi, Ltd. According to the result of photoluminescence measured at an excitation wavelength of 350 nm, the spectrum had the maximum intensity at 451 nm.

Example 5

Synthesis of Exemplary Compounds A26 and A27

The reactions and purifications were conducted as in Example 1 except that organic compound E8 used in Example 1 was changed to E11.

[Chem. 13]

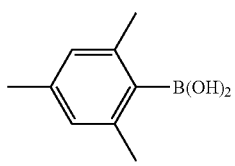

E11

The emission spectrum of a toluene solution of a mixture of Exemplary Compounds A26 and A27 with a concentration of $1\times10^{-5}$ mol/L was measured using a fluorescence spectrophotometer F-4500 manufactured by Hitachi, Ltd. According to the result of photoluminescence measured at an excitation wavelength of 350 nm, the spectrum had the maximum intensity at 445 nm.

Example 6

Synthesis of Exemplary Compounds A93 and A95

The reactions and purifications were conducted as in Example 1 except that organic compound E5 used in Example 1 was changed to E13.

[Chem. 14]

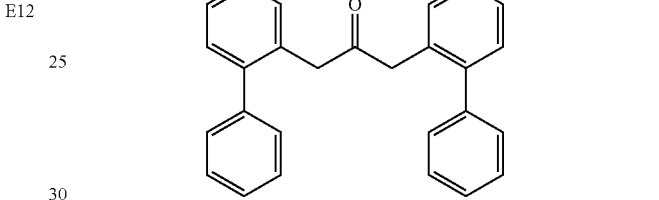

E13

The emission spectrum of a toluene solution of a mixture of Exemplary Compounds A93 and A95 with a concentration of $1\times10^{-5}$ mol/L was measured using a fluorescence spectrophotometer F-4500 manufactured by Hitachi, Ltd. According to the result of photoluminescence measured at an excitation wavelength of 350 nm, the spectrum had the maximum intensity at 449 nm.

Examples 7 to 30

In Examples 7 to 30, the multilayer organic light-emitting devices described in the fifth example (anode/hole injection layer/hole-transporting layer/light-emitting layer/hole.exciton-blocking layer/electron-transporting layer/cathode) were prepared. In each example, first, an ITO film having a thickness of 100 nm was patterned on a glass substrate. On the substrate having the ITO film thereon, organic layers and electrode layers described below were successively deposited by a resistance-heating vacuum evaporation method in a vacuum chamber at a pressure of $10^{-5}$ Pa so that the area of the electrodes facing each other was 3 mm$^2$. When a guest material includes two types of compounds, the guest material is a mixture of structural isomers having substituents at different positions, the mixture having a ratio of about 1:1.

Hole injection layer/Hole-transporting layer (30 nm): G-1

Light-emitting layer (30 nm); Host: G-2, Guest: Exemplary Compound (weight ratio: 5%)

Hole/exciton-blocking layer (10 nm): G-3

Electron-transporting layer (30 nm): G-4

Metal electrode layer 1 (1 nm): LiF

Metal electrode layer 2 (100 nm): Al

[Chem. 15]

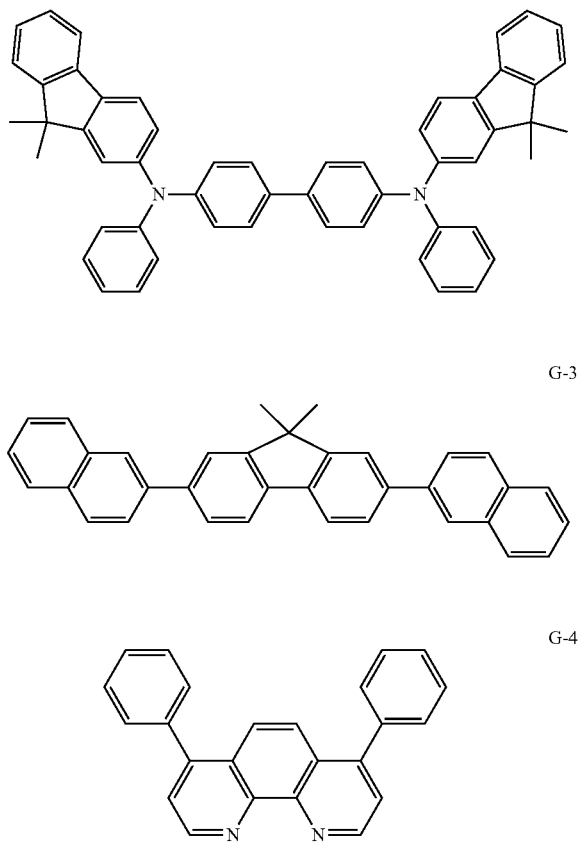

The current-voltage characteristic of each EL device was measured with a pA meter 4140B manufactured by Hewlett-Packard Development Company, and the light-emission luminance thereof was measured with a luminance meter BM7 manufactured by Topcon Corporation. The luminous efficiency and the voltage of Example 7 to Example 30 are shown in Table 4.

TABLE 4

| | Guest | G-2 | Luminous efficiency (cd/A) | Voltage (V) |
|---|---|---|---|---|
| Example 7 | A1 | H12 | 6.5 | 4.2 |
| Example 8 | A1, A2 | H12 | 6.5 | 4.2 |
| Example 9 | A4 | H4 | 6.1 | 4.0 |
| Example 10 | A20 | H21 | 6.4 | 4.2 |
| Example 11 | A20, A21 | H21 | 6.4 | 4.2 |
| Example 12 | A20, A21 | H10 | 5.8 | 4.0 |
| Example 13 | A21 | H21 | 6.4 | 4.2 |
| Example 14 | A26, A27 | H22 | 6.0 | 4.6 |
| Example 15 | A35, A36 | H9 | 5.8 | 5.0 |
| Example 16 | A37 | H15 | 5.8 | 4.7 |
| Example 17 | A44 | H23 | 6.6 | 4.1 |
| Example 18 | A44, A45 | H27 | 5.6 | 5.0 |
| Example 19 | A48, A50 | H8 | 5.5 | 4.8 |
| Example 20 | A51, A52 | H10 | 5.5 | 4.7 |
| Example 21 | A65, A66 | H22 | 6.5 | 4.5 |
| Example 22 | A67, A68 | H27 | 6.0 | 4.3 |
| Example 23 | A85, A89 | H28 | 5.6 | 5.1 |
| Example 24 | A96, A97 | H9 | 5.4 | 5.3 |
| Example 25 | A113, A114 | H10 | 5.8 | 4.7 |
| Example 26 | A118 | H2 | 3.9 | 5.9 |

TABLE 4-continued

| | Guest | G-2 | Luminous efficiency (cd/A) | Voltage (V) |
|---|---|---|---|---|
| Example 27 | B4 | H23 | 6.4 | 4.3 |
| Example 28 | B25 | H28 | 6.3 | 4.0 |
| Example 29 | C5, C8 | H23 | 4.3 | 5.5 |
| Example 30 | C10 | H18 | 4.8 | 6.1 |

Examples 31 to 35

In Examples 31 to 35, the multilayer organic light-emitting devices described in the fifth example (anode/hole injection layer/hole-transporting layer/light-emitting layer/electron-transporting layer/electron injection layer/cathode) were prepared. Organic light-emitting devices having a resonating structure were prepared by a method described below. In each example, first, an aluminum alloy (AlNd) functioning as a reflective anode was deposited on a glass substrate functioning as a support by a sputtering method so as to have a thickness of 100 nm. Furthermore, ITO functioning as a transparent anode was deposited by a sputtering method so as to have a thickness of 80 nm. Next, an element isolation film composed of an acrylic resin and having a thickness of 1.5 μm was formed in a peripheral portion of the anode, and an opening with a radius of 3 mm was formed therein. The substrate was sequentially washed with ultrasonic waves using acetone and isopropyl alcohol (IPA). The substrate was then washed with IPA under boiling, and dried. Furthermore, UV/ozone cleaning was conducted on the surface of the substrate. Furthermore, organic layers described below were successively deposited by a resistance-heating vacuum evaporation method in a vacuum chamber at a pressure of $10^{-5}$ Pa. Subsequently, IZO was deposited as a cathode by a sputtering method to form a transparent electrode having a thickness of 30 nm. After the formation, sealing is performed in a nitrogen atmosphere. Thus, the organic light-emitting devices were prepared.

Hole injection layer (95 nm): G-11
Hole-transporting layer (10 nm): G-12
Light-emitting layer (35 nm); Host: G-13, Guest: Exemplary Compound (weight ratio: 2%)
Electron-transporting layer (10 nm): G-14
Electron injection layer (70 nm): G-15 (weight ratio: 80%), Li (weight ratio: 20%)

[Chem. 16]

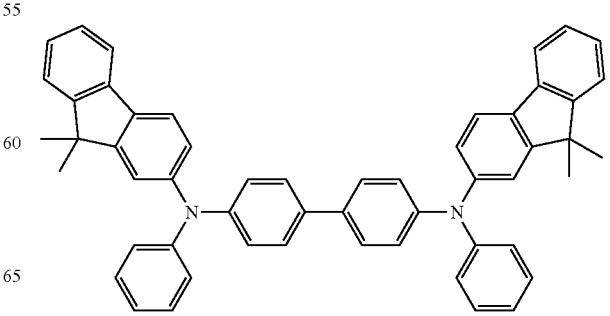

-continued

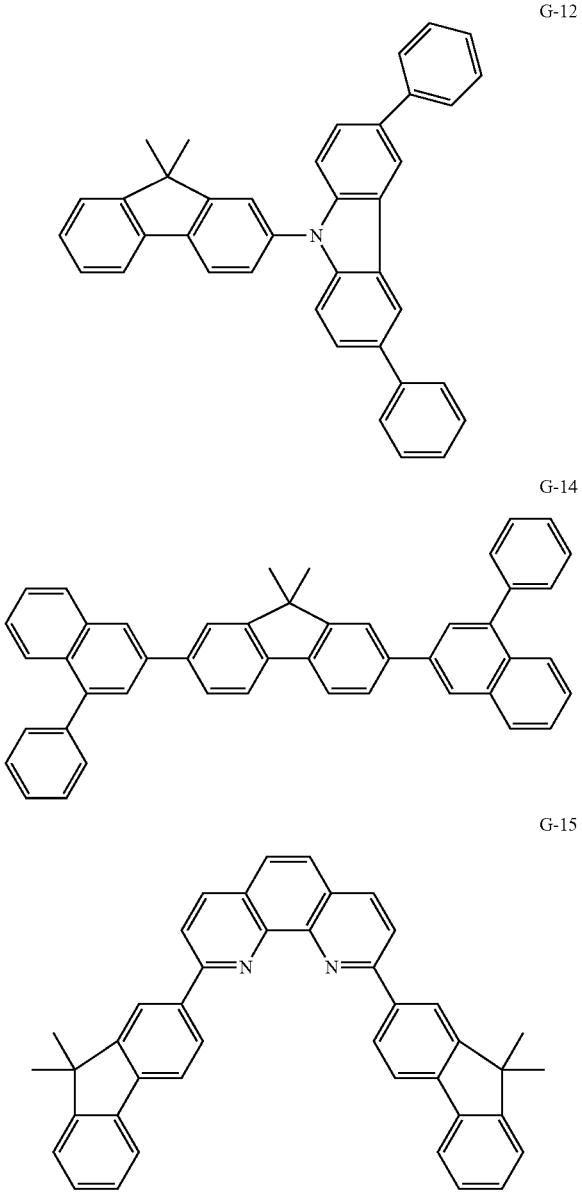

G-12

G-14

G-15

The current-voltage characteristic of each EL device was measured with a pA meter 4140B manufactured by Hewlett-Packard Development Company, and the light-emission luminance thereof was measured with a luminance meter BM7 manufactured by Topcon Corporation. The luminous efficiency and the voltage of Example 31 to Example 35 are shown in Table 5.

TABLE 5

|  | Guest | G-13 | Luminous efficiency (cd/A) | Voltage (V) |
| --- | --- | --- | --- | --- |
| Example 31 | A20, A21 | H7 | 3.0 | 4.1 |
| Example 32 | A38, A39 | H22 | 3.1 | 4.5 |
| Example 33 | A48, A50 | H8 | 3.4 | 4.3 |
| Example 34 | A51, A52 | H10 | 3.4 | 4.6 |
| Example 35 | A93, A95 | H8 | 3.1 | 4.0 |

Example 36

Synthesis of Exemplary Compounds A44 and A45

The reactions and purifications were conducted as in Example 1 except that organic compound E8 used in Example 1 was changed to E14.

[Chem. 17]

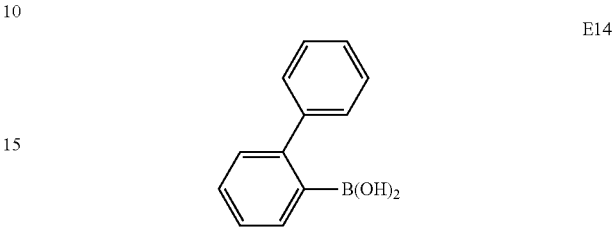

E14

The emission spectrum of a toluene solution of a mixture of Exemplary Compounds A44 and A45 with a concentration of $1\times10^{-5}$ mol/L was measured using a fluorescence spectrophotometer F-4500 manufactured by Hitachi, Ltd. According to the result of photoluminescence measured at an excitation wavelength of 350 nm, the spectrum had the maximum intensity at 450 nm.

Example 37

Synthesis of Exemplary Compounds A147 and A148

The reactions and purifications were conducted as in Example 1 except that organic compound E8 used in Example 1 was changed to E15.

[Chem. 18]

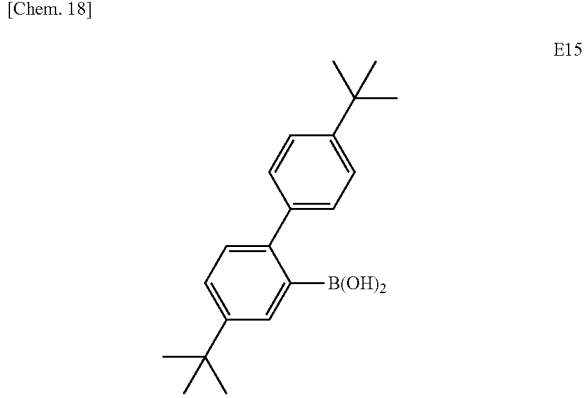

E15

The emission spectrum of a toluene solution of a mixture of Exemplary Compounds A147 and A148 with a concentration of $1\times10^{-5}$ mol/L was measured using a fluorescence spectrophotometer F-4500 manufactured by Hitachi, Ltd. According to the result of photoluminescence measured at an excitation wavelength of 350 nm, the spectrum had the maximum intensity at 451 nm.

Example 38

Synthesis of Exemplary Compounds A35 and A36

The reactions and purifications were conducted as in Example 1 except that organic compound E8 used in Example 1 was changed to E16.

[Chem. 19]

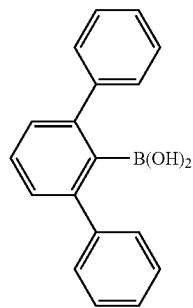

E16

The emission spectrum of a toluene solution of a mixture of Exemplary Compounds A35 and A36 with a concentration of 1×10⁻⁵ mol/L was measured using a fluorescence spectrophotometer F-4500 manufactured by Hitachi, Ltd. According to the result of photoluminescence measured at an excitation wavelength of 350 nm, the spectrum had the maximum intensity at 451 nm.

Example 39

Synthesis of Exemplary Compounds A149 and A150

The reactions and purifications were conducted as in Example 1 except that organic compound E8 used in Example 1 was changed to E17.

[Chem. 20]

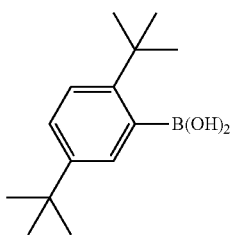

E17

The emission spectrum of a toluene solution of a mixture of Exemplary Compounds A149 and A150 with a concentration of 1×10⁻⁵ mol/L was measured using a fluorescence spectrophotometer F-4500 manufactured by Hitachi, Ltd. According to the result of photoluminescence measured at an excitation wavelength of 350 nm, the spectrum had the maximum intensity at 448 nm.

Example 40

Synthesis of Exemplary Compounds A155 and A156

The reactions and purifications were conducted as in Example 1 except that organic compound E8 used in Example 1 was changed to E18.

[Chem. 21]

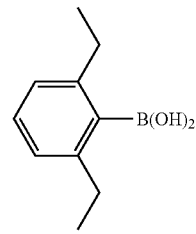

E18

The emission spectrum of a toluene solution of a mixture of Exemplary Compounds A155 and A156 with a concentration of 1×10⁻⁵ mol/L was measured using a fluorescence spectrophotometer F-4500 manufactured by Hitachi, Ltd. According to the result of photoluminescence measured at an excitation wavelength of 350 nm, the spectrum had the maximum intensity at 447 nm.

Example 41

Synthesis of Exemplary Compounds A151 and A152

The reactions and purifications were conducted as in Example 1 except that organic compound E8 used in Example 1 was changed to E19.

[Chem. 22]

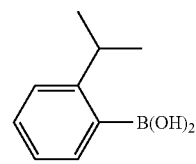

E19

The emission spectrum of a toluene solution of a mixture of Exemplary Compounds A151 and A152 with a concentration of 1×10⁻⁵ mol/L was measured using a fluorescence spectrophotometer F-4500 manufactured by Hitachi, Ltd. According to the result of photoluminescence measured at an excitation wavelength of 350 nm, the spectrum had the maximum intensity at 446 nm.

Example 42

Synthesis of Exemplary Compounds A163 and A164

The reactions and purifications were conducted as in Example 1 except that organic compound E8 used in Example 1 was changed to E20.

[Chem. 23]

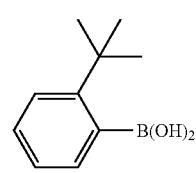

E20

The emission spectrum of a toluene solution of a mixture of Exemplary Compounds A163 and A164 with a concentration of 1×10⁻⁵ mol/L was measured using a fluorescence spectrophotometer F-4500 manufactured by Hitachi, Ltd. According to the result of photoluminescence measured at an excitation wavelength of 350 nm, the spectrum had the maximum intensity at 446 nm.

Example 43

Synthesis of Exemplary Compounds A157 and A158

The reactions and purifications were conducted as in Example 1 except that organic compound E5 used in Example 1 was changed to E10 and organic compound E8 used in Example 1 was changed to E17.

[Chem. 24]

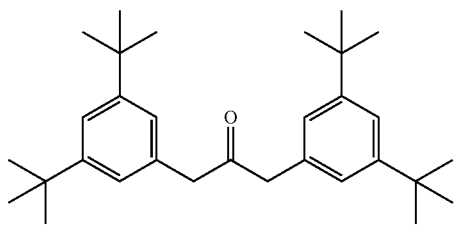

E10

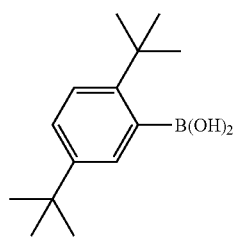

E17

The emission spectrum of a toluene solution of a mixture of Exemplary Compounds A157 and A158 with a concentration of $1\times10^{-5}$ mol/L was measured using a fluorescence spectrophotometer F-4500 manufactured by Hitachi, Ltd. According to the result of photoluminescence measured at an excitation wavelength of 350 nm, the spectrum had the maximum intensity at 447 nm.

Examples 44 to 54

In Examples 44 to 54, the multilayer organic light-emitting devices described in the fifth example (anode/hole injection layer/hole-transporting layer/light-emitting layer/hole•exciton-blocking layer/electron-transporting layer/cathode) were prepared. In each example, first, an ITO film having a thickness of 100 nm was patterned on a glass substrate. On the substrate having the ITO film thereon, organic layers and electrode layers described below were successively deposited by a resistance-heating vacuum evaporation method in a vacuum chamber at a pressure of $10^{-5}$ Pa so that the area of the electrodes facing each other was 3 $mm^2$. When a guest material includes two types of compounds, the guest material is a mixture of structural isomers having substituents at different positions, the mixture having a ratio of about 1:1.
Hole injection layer (20 nm): G-16
Hole-transporting layer (10 nm): G-17
Light-emitting layer (30 nm); Host: G-18, Guest: Exemplary Compound (weight ratio: 5%)
Hole/exciton-blocking layer (10 nm): G-19
Electron-transporting layer (30 nm): G-20
Metal electrode layer 1 (1 nm): LiF
Metal electrode layer 2 (100 nm): Al

[Chem. 25]

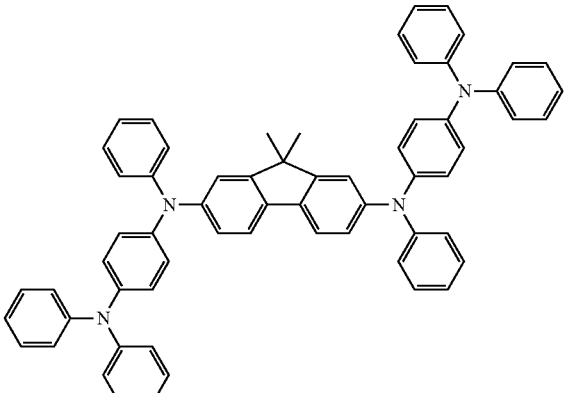

G-16

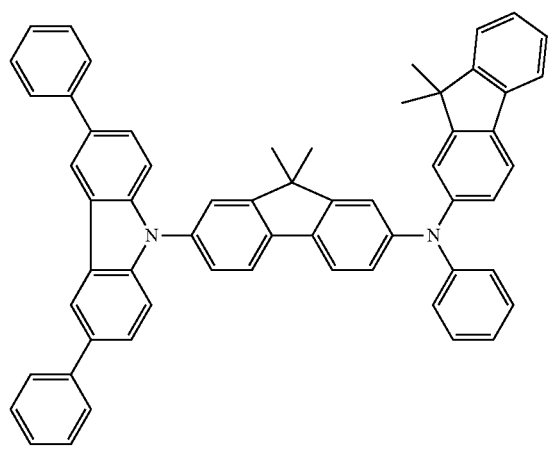

G-17

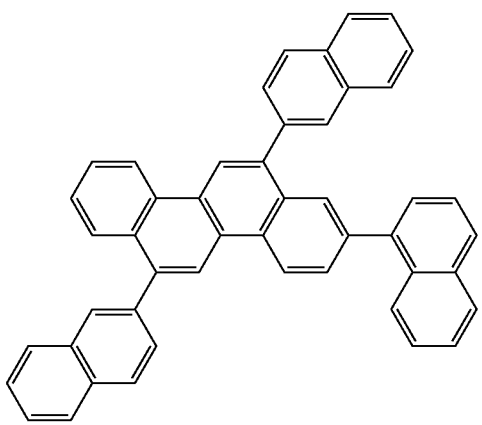

G-19

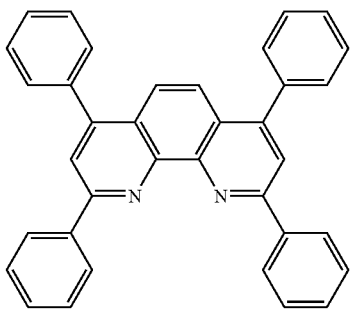

G-20

The current-voltage characteristic of each EL device was measured with a pA meter 4140B manufactured by Hewlett-Packard Development Company, and the light-emission luminance thereof was measured with a luminance meter BM7 manufactured by Topcon Corporation. The luminous efficiency and the voltage of Example 44 to Example 54 are shown in Table 6.

TABLE 6

|  | Guest | G-18 | Luminous efficiency (cd/A) | Voltage (V) |
| --- | --- | --- | --- | --- |
| Example 44 | A20, A21 | H31 | 6.1 | 4.2 |
| Example 45 | A35, A36 | H30 | 6.2 | 4.1 |
| Example 46 | A44, A45 | H10 | 5.8 | 4.0 |
| Example 47 | A44, A45 | H21 | 6.4 | 4.2 |
| Example 48 | A147, A148 | H29 | 6.3 | 4.2 |
| Example 49 | A149, A150 | H31 | 6.5 | 4.1 |
| Example 50 | A155, A156 | H21 | 6.4 | 4.2 |
| Example 51 | A151, A152 | H31 | 6.0 | 4.3 |
| Example 52 | A157, A158 | H8 | 5.1 | 4.0 |
| Example 53 | A163, A164 | H21 | 6.1 | 4.0 |
| Example 54 | A163, A164 | H31 | 6.3 | 4.2 |

RESULTS AND DISCUSSION

The organic compounds according to the present invention are novel compounds which exhibit a high quantum yield and which are suitable for blue-light emission. When the organic compounds according to the present invention are used in organic light-emitting devices, it is possible to make light-emitting devices having good luminescence properties.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-105356, filed Apr. 23, 2009 and No. 2010-015851 filed Jan. 27, 2010, which are hereby incorporated by reference herein in their entirety.

The invention claimed is:

1. An acenaphtho[1,2-k]benzo[e]acephenanthrene derivative represented by general formula (1):

[Chem. 1]

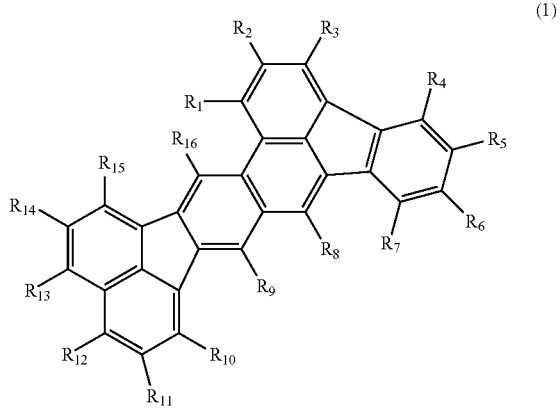

(1)

wherein $R_1$ to $R_{16}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group; and
at least one of $R_1$ to $R_8$ and $R_{10}$ to $R_{15}$ is selected from a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

2. The acenaphtho[1,2-k]benzo[e]acephenanthrene derivative according to claim 1, wherein $R_1$ to $R_{16}$ are each independently selected from a hydrogen atom and a substituted or unsubstituted aryl group.

3. An organic light-emitting device comprising:
a cathode;
an anode; and
an organic compound layer disposed between the anode and the cathode,
wherein the organic compound layer contains the acenaphtho[1,2-k]benzo[e]acephenanthrene derivative according to claim 1.

4. The organic light-emitting device according to claim 3, wherein the organic compound layer is a light-emitting layer.

5. An image display apparatus comprising:
a plurality of pixels, each of which is the organic light-emitting device according to claim 3; and
a unit configured to supply an electrical signal to the organic light-emitting device.

* * * * *